(12) United States Patent
Kozuka et al.

(10) Patent No.: US 10,582,902 B2
(45) Date of Patent: Mar. 10, 2020

(54) CATHETER TIP-END ROTATION ANGLE DETECTION APPARATUS, CATHETER TIP-END ROTATION ANGLE DETECTION METHOD, AND CATHETER TIP-END ROTATION ANGLE DETECTION PROGRAM

(71) Applicant: Panasonic Corporation, Osaka (JP)

(72) Inventors: Kazuki Kozuka, Fukui (JP); Toru Nakada, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 1238 days.

(21) Appl. No.: 14/259,354

(22) Filed: Apr. 23, 2014

(65) Prior Publication Data

US 2014/0236000 A1    Aug. 21, 2014

Related U.S. Application Data

(63) Continuation of application No. PCT/JP2013/004627, filed on Jul. 31, 2013.

(30) Foreign Application Priority Data

Aug. 6, 2012    (JP) .................................. 2012-173859

(51) Int. Cl.
*A61B 6/12*        (2006.01)
*A61B 6/00*        (2006.01)
(Continued)

(52) U.S. Cl.
CPC ............... *A61B 6/12* (2013.01); *A61B 6/461* (2013.01); *A61B 6/467* (2013.01); *A61B 6/485* (2013.01);
(Continued)

(58) Field of Classification Search
CPC ................................................... A61B 8/4245
See application file for complete search history.

(56) References Cited

U.S. PATENT DOCUMENTS

| 2005/0203375 A1* | 9/2005 | Willis | A61B 5/0422 600/407 |
| 2008/0146942 A1* | 6/2008 | Dala-Krishna | A61B 6/12 600/466 |
| 2011/0230758 A1* | 9/2011 | Eichler | A61B 5/06 600/424 |

FOREIGN PATENT DOCUMENTS

| JP | 2009-162920 | 7/2009 |
| JP | 2009-201682 | 9/2009 |

(Continued)

OTHER PUBLICATIONS

International Search Report dated Oct. 1, 2013 in International (PCT) Application No. PCT/JP2013/004627.

(Continued)

*Primary Examiner* — Luther Behringer
(74) *Attorney, Agent, or Firm* — Wenderoth, Lind & Ponack, L.L.P.

(57) ABSTRACT

A catheter tip-end rotation angle detection apparatus includes a catheter rotation angle detecting unit that detects a rotation angle of a catheter in an operator's hand, an image processing unit that extracts a catheter tip-end region from an x-ray fluoroscopic image of a first x-ray fluoroscopic capturing unit, a catheter tip-end rotation angle calculation unit that calculates an offset angle between an operator's hand-side rotation angle and a catheter tip-end rotation angle, from a fluoroscopic image captured at an action time of rotating the catheter by one turn, based on an angle at which a catheter tip-end region becomes a straight line in the image processing unit, and that calculates a catheter tip-end rotation angle based on the offset angle and the operator's (Continued)

hand-side rotation angle, during a catheter manipulation time, and an output unit that outputs the calculated catheter tip-end rotation angle.

12 Claims, 31 Drawing Sheets

(51) Int. Cl.
    *A61B 90/00*     (2016.01)
    *A61M 25/01*     (2006.01)
    *A61M 25/09*     (2006.01)
    *A61B 34/20*     (2016.01)

(52) U.S. Cl.
    CPC .......... *A61B 6/5217* (2013.01); *A61B 6/5235* (2013.01); *A61B 90/37* (2016.02); *A61M 25/0108* (2013.01); *A61M 25/09* (2013.01); *A61B 2034/2065* (2016.02); *A61B 2090/067* (2016.02); *A61B 2090/376* (2016.02); *A61M 2025/09166* (2013.01)

(56) References Cited

FOREIGN PATENT DOCUMENTS

| JP | 2009-279343 | 12/2009 |
|----|-------------|---------|
| JP | 2011-010826 | 1/2011 |

OTHER PUBLICATIONS

"Computervision—Geometry of Eyesight—" by Atsushi Sato, Corona Publishing Co., Ltd., 1999, with partial translation.
International Preliminary Report on Patentability and Written Opinion of the International Searching Authority dated Feb. 19, 2015 in International (PCT) Application No. PCT/JP2013/004627.

* cited by examiner

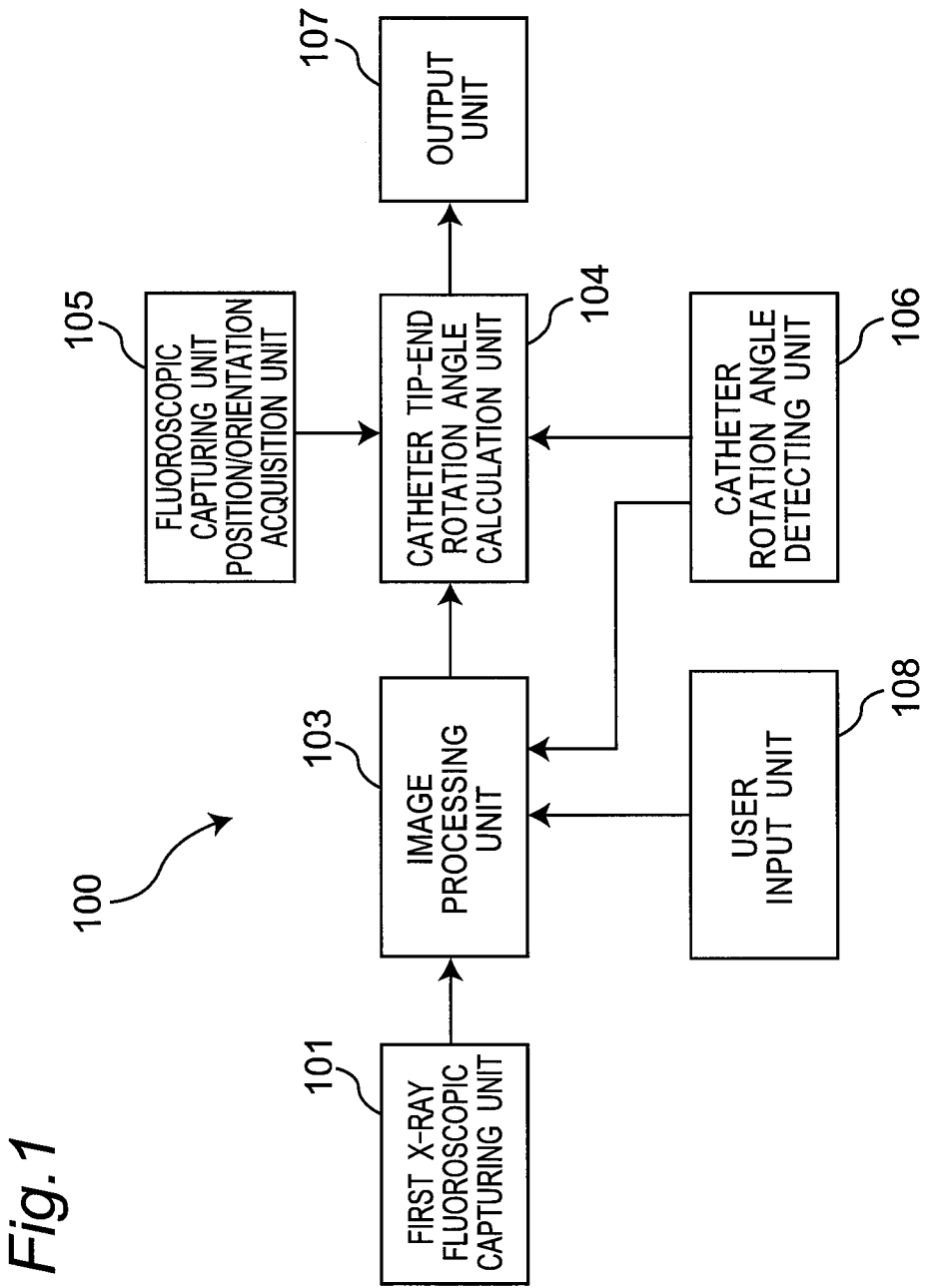

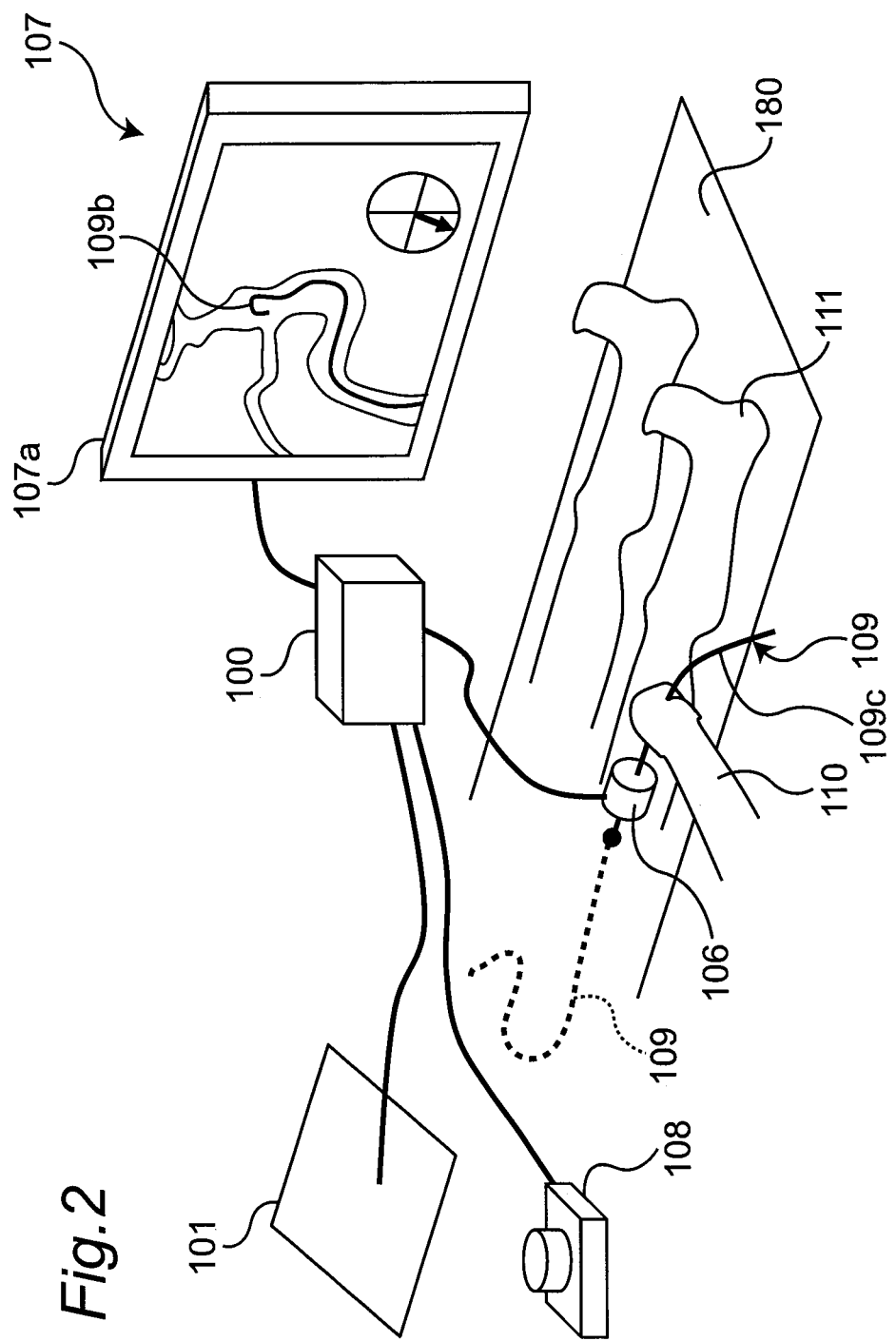

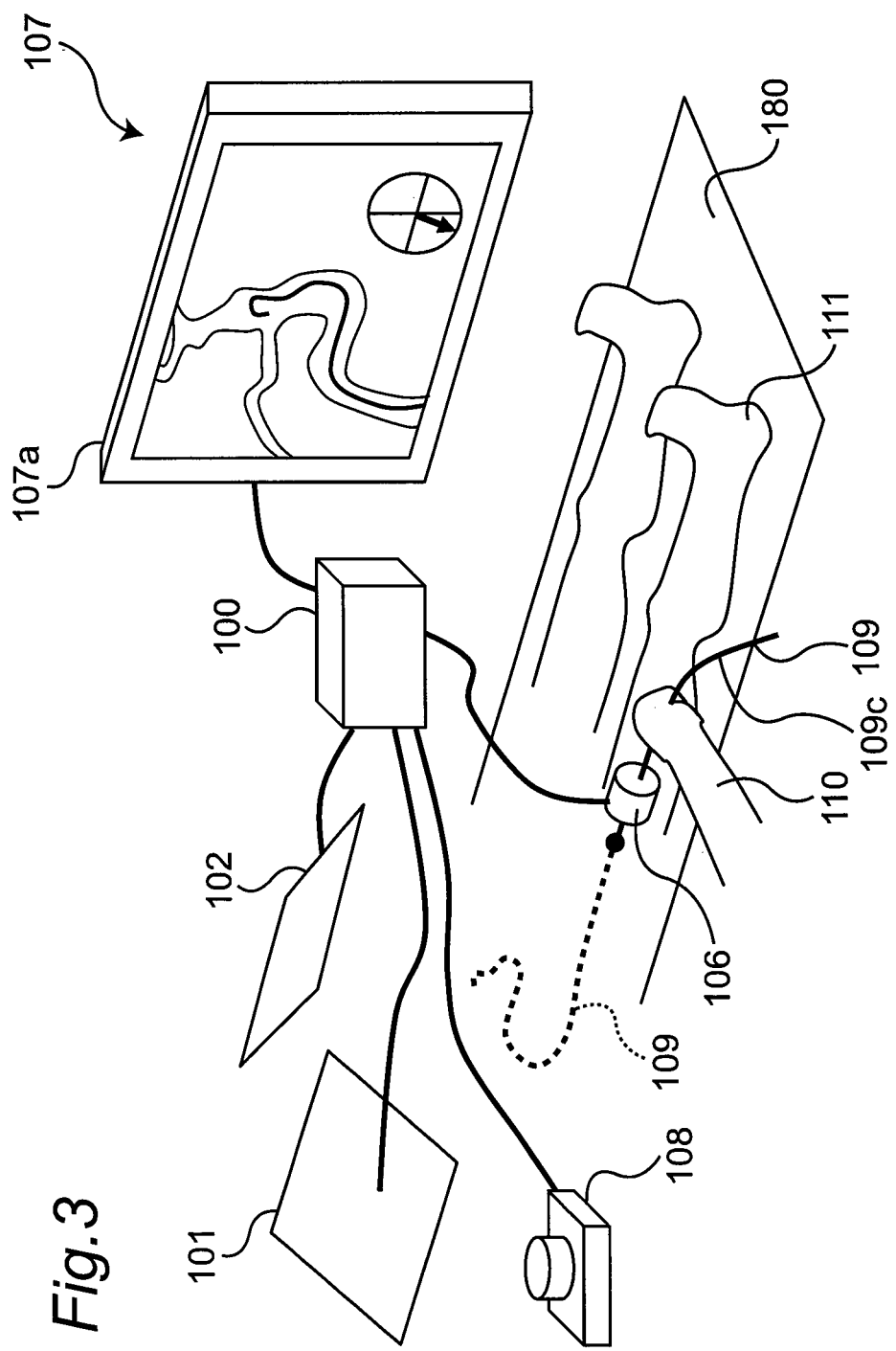

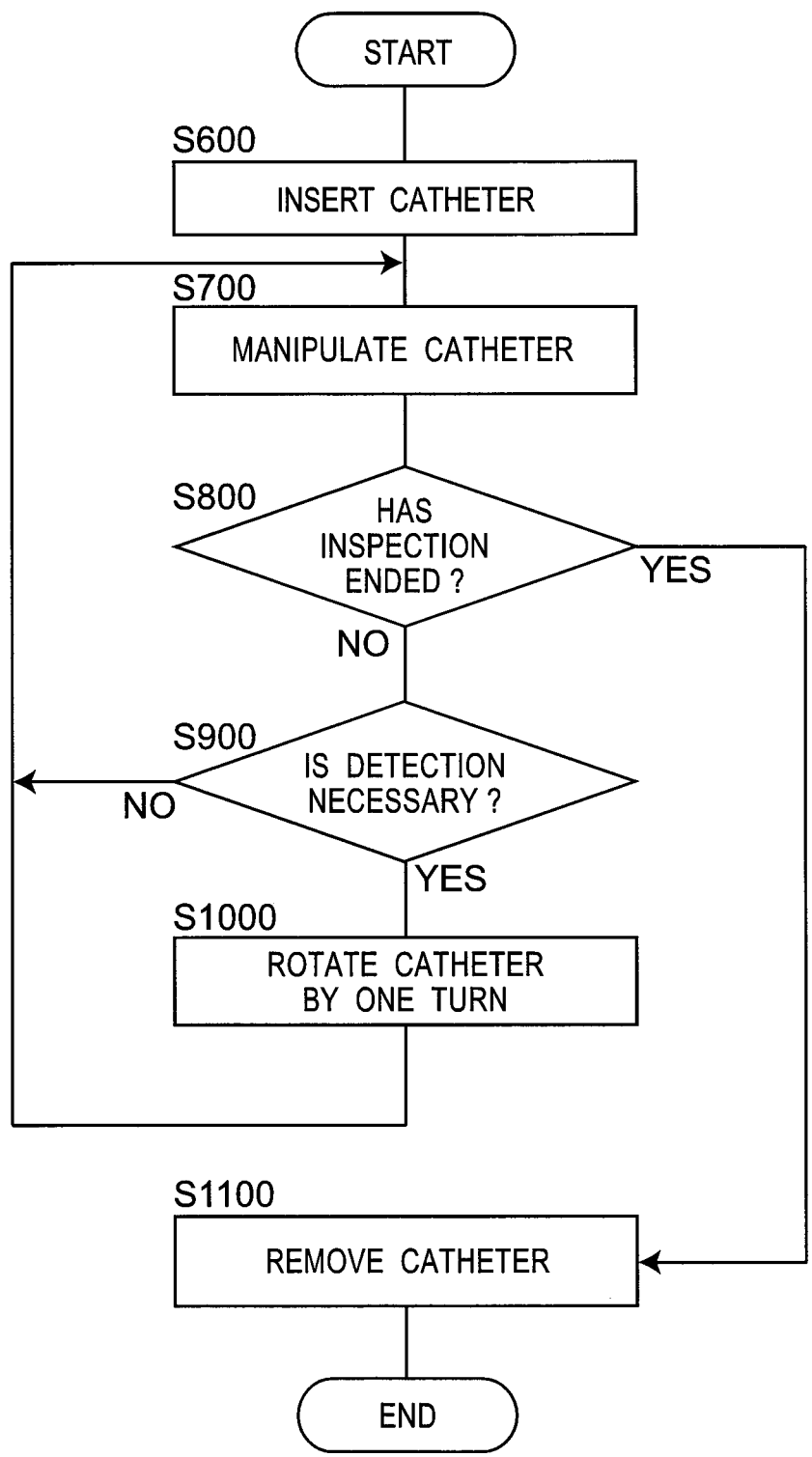

| CATHETER TIP-END IMAGE OF FIRST X-RAY FLUOROSCOPIC CAPTURING UNIT | / |  | / |
|---|---|---|---|
| OPERATOR'S HAND-SIDE ROTATION ANGLE | 0° |  | 180° |

| CATHETER TIP-END IMAGE OF FIRST X-RAY FLUOROSCOPIC CAPTURING UNIT | / | ⌒ | / |
|---|---|---|---|
| OPERATOR'S HAND-SIDE ROTATION ANGLE | 10° | 100° | 190° |

CATHETER TIP-END ROTATION ANGLE DETECTION APPARATUS, CATHETER TIP-END ROTATION ANGLE DETECTION METHOD, AND CATHETER TIP-END ROTATION ANGLE DETECTION PROGRAM

CROSS-REFERENCE TO RELATED APPLICATIONS

This is a continuation application of International Application No. PCT/JP2013/004627, with an international filing date of Jul. 31, 2013, which claims priority of Japanese Patent Application No.: 2012-173859 filed on Aug. 6, 2012, the content of which is incorporated herein by reference.

TECHNICAL FIELD

The technical field relates to a catheter tip-end rotation angle detection apparatus, a catheter tip-end rotation angle detection method, and a catheter tip-end rotation angle detection program, for understanding a catheter tip-end position/orientation at an x-ray image capturing time. More specifically, the technical field relates to a catheter tip-end rotation angle detection apparatus, a catheter tip-end rotation angle detection method, and a catheter tip-end rotation angle detection program for detecting a catheter tip-end rotation angle from values of a rotation angle sensor that is set at a catheter operator's hand, by using two-eye images captured by two x-ray fluoroscopic image capturing units.

BACKGROUND ART

In recent years, due to influences of the aging society and changes in life styles based on westernization of food practice, there are increasing number of diseases attributable to stenosis or blockage of the blood vessel such as ischemic heart disease (angina pectoris, myocardial infarction), cerebrovascular disease, or arteriosclerosis obliterans. As an examination for checking stenosis or blockage of the blood vessel, there is catheter contrast radiography. In the catheter contrast radiography, a contrast medium as an x-ray non-transmission substance is used to diagnose a lesion of the blood vessel by continuously capturing images of a state of the blood vessel or a blood flow state. Specifically, the catheter operator thrusts a needle into the femoral artery (vein) near the hip joint or the arterial (vein) of the arm, and inserts a tube having a diameter of a few millimeters called catheter into the blood vessel. A method of capturing an image of a target blood vessel by inserting a catheter tip-end to the target blood vessel and injecting a contrast medium into a specific blood vessel is carried out in general. Therefore, in the catheter contrast radiography, in order to insert the catheter into the target blood vessel, at a blood branch point, it is necessary to match the direction (rotation angle) of the catheter tip-end with a branch direction of the target blood vessel.

However, because the catheter operator manipulates the catheter by watching a two-dimensional fluoroscopic image, the catheter operator cannot determine information of a depth. Therefore, there is a problem in that the catheter operator cannot understand an accurate direction of the catheter tip-end, cannot enter the catheter into the target blood vessel, and takes time in contrast radiography. In the x-ray fluoroscopy, it is unavoidable to shorten the time taken for contrast radiography, to reduce the amount of radiation to a patient. To shorten the time taken for contrast radiography by a smooth catheter manipulation and surgery, it is important to detect an accurate direction of the catheter tip-end.

As a conventional method of detecting the direction of the catheter tip-end, there is a method of using a rotation sensor that is set on a catheter operator's hand side (for example, refer to Patent Literature 1). FIG. 33 shows a conventional catheter manipulation detection device described in Patent Literature 1. In FIG. 33, a catheter rotation angle detecting unit 1106 detects an angle of the catheter that is rotated by the operator. A catheter tip-end rotation angle deciding unit acquires a rotation angle of the catheter rotation angle detecting unit 1106, and outputs the rotation angle directly to a display unit 1107 as a catheter tip-end rotation angle.

On the other hand, as a method of detecting a tip-end rotation angle of a surgical tool from an image, there is a method in which a marker of continuous pattern is provided in an endoscope, and the direction of the endoscope is detected from an image-captured image of the endoscope and a marker image (for example, refer to Patent Literature 2). Further, there is a method in which, by providing a heteromorphic convex portion that does not transmit an electromagnetic wave in the catheter, the heteromorphic convex portion is confirmed by an X-ray device or the like (for example, refer to Patent Literature 3).

CITATION LIST

Patent Literature

[Patent Literature 1] Japanese Unexamined Patent Publication No. 2009-162920
[Patent Literature 2] Japanese Unexamined Patent Publication No. 2009-201682
[Patent Literature 3] Japanese Unexamined Patent Publication No. 2011-10826

SUMMARY OF THE INVENTION

However, according to the configuration in Patent Literature 1, an angle that can be measured by the catheter rotation angle detecting unit is a rotation angle of a sensor at a catheter operator's hand. Therefore, when a catheter tip-end rotation angle at a catheter insertion time and current catheter tip-end rotation angle are different as is the case with a blood vessel of a complex shape, a standard (direction of 0 degrees) of the catheter tip-end rotation angle is not clear. Therefore, the angle that can be acquired by the catheter rotation angle detecting unit does not correspond to the catheter, and there has been a problem in that even when the value of the sensor is output as it is, the catheter operator cannot understand the direction of the catheter. On the other hand, according to the method of detecting a tip-end rotation angle of a surgical device from the image, it is necessary to set a marker in the surgical device. However Patent Literature 2 is for capturing an image by visible light, and the image of the marker set on the surface of the catheter is captured by transmission of the light in the time of x-ray fluoroscopic capturing. Therefore, front and back surfaces of the catheter cannot be distinguished from each other when observed through an image-capturing device, and there is a problem in that the direction cannot be detected from the marker image. In the case of detecting the direction of the catheter without a marker of the catheter, there are considered a method of matching the direction of the catheter with a three-dimensional shape model of the catheter tip-end after extracting a catheter region from a fluoroscopic image, and a method of detecting the direction of the catheter tip-end by restoring a three-dimensional shape and by calculating an orientation of the catheter tip-end. However, according to the method of matching the direction of the catheter with a three-dimensional shape model of the catheter, a searching range of position/orientation of the model is enormously large, and it is difficult to understand in real time an accurate direction of the catheter. On the other hand, according to the method of restoring a three-dimensional shape, it is not possible to extract an accurate corresponding point without a marker from two-eye fluoroscopic images of the catheter. Therefore, it is not possible to acquire an accurate three-dimensional shape, and it is difficult to detect in high precision a catheter tip-end rotation angle.

One non-limiting and exemplary embodiment provides a catheter tip-end rotation angle detection apparatus, a catheter tip-end rotation angle detection method, and a catheter tip-end rotation angle detection program for detecting a catheter tip-end direction (tip-end rotation angle), without setting special markers in the catheter in an environment that the direction (tip-end rotation angle) at a catheter insertion time and the direction (tip-end rotation angle) of the catheter at a detection time are different.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature: A catheter tip-end rotation angle detection apparatus that detects a rotation angle around an axis of a bent portion of a catheter, the catheter having the bent portion at a tip-end that is bent in a hook shape relative to a straight-line shaped base, as a catheter tip-end region, and being inserted into a body lumen, the catheter tip-end rotation angle detection apparatus comprising:

a catheter rotation angle detecting unit that detects an operator's hand-side rotation angle of the catheter in a hand of an operator;

an image processing unit that extracts the catheter tip-end region from an x-ray fluoroscopic image of a first x-ray fluoroscopic capturing unit that captures an x-ray fluoroscopic image by irradiating a radioactive ray to an image-capture target portion of a subject;

a catheter tip-end rotation angle calculation unit that performs a catheter tip-end rotation angle calculation process in which an offset angle between the operator's hand-side rotation angle detected by the catheter rotation angle detecting unit and a rotation angle of the catheter tip-end is calculated from an x-ray fluoroscopic image captured at a time of an action of rotating the catheter by one turn by the operator, based on respective angles of the bent portion and the base of the catheter in a state that the bent portion and the base are superposed and in a state that the bent portion and the base are deviated in the image processing unit and, during a catheter manipulation after ending the action of rotating the catheter by the one turn, the catheter tip-end rotation angle is calculated based on the offset angle and the operator's hand-side rotation angle; and an output unit that outputs the catheter tip-end rotation angle calculated by the catheter tip-end rotation angle calculation unit.

These general and specific aspects may be implemented using a system, a method, and a computer program, and any combination of systems, methods, and computer programs.

According to the above aspects of the present disclosure, it is possible to understand the rotation angle (direction) of the catheter tip-end even in a body lumen such as a blood vessel of a complex shape, and it is possible to perform a smooth catheter manipulation.

BRIEF DESCRIPTION OF THE DRAWINGS

These and other aspects and features of the present disclosure will become clear from the following description taken in conjunction with the embodiments thereof with reference to the accompanying drawings, in which:

FIG. 1 is a configuration view of functional blocks of a catheter tip-end rotation angle detection apparatus according to a first embodiment of the present invention;

FIG. 2 is a view showing a utilization form of the catheter tip-end rotation angle detection apparatus according to the first embodiment;

FIG. 3 is a view showing a utilization form of a catheter tip-end rotation angle detection apparatus according to a modification example of the first embodiment;

FIG. 5 is a view showing an operator workflow of a catheter tip-end rotation angle detection;

DETAILED DESCRIPTION

Figure 4A:
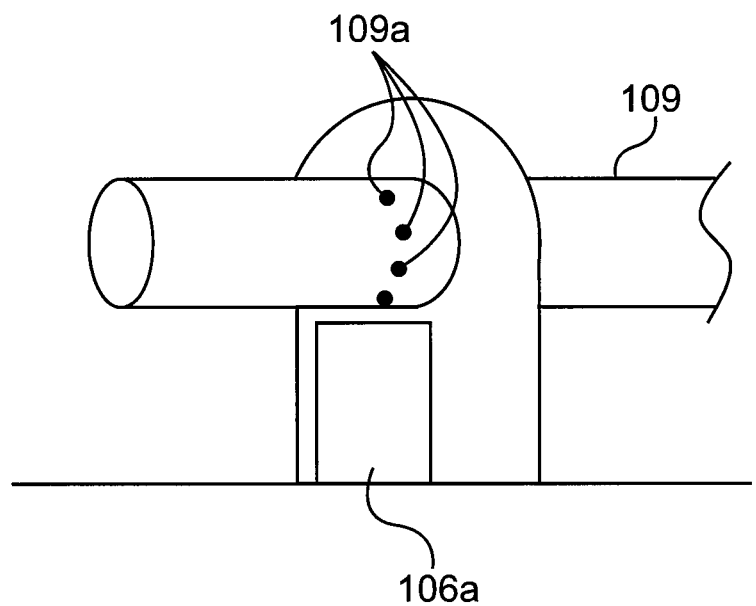
FIG. 4A is an explanatory view of an example of a catheter rotation angle detecting unit.

Examples of the disclosed technique are as follows.

1st aspect: A catheter tip-end rotation angle detection apparatus that detects a rotation angle around an axis of a bent portion of a catheter, the catheter having the bent portion at a tip-end that is bent in a hook shape relative to a straight-line shaped base, as a catheter tip-end region, and being inserted into a body lumen, the catheter tip-end rotation angle detection apparatus comprising:

a catheter rotation angle detecting unit that detects an operator's hand-side rotation angle of the catheter in a hand of an operator;

an image processing unit that extracts the catheter tip-end region from an x-ray fluoroscopic image of a first x-ray fluoroscopic capturing unit that captures an x-ray fluoroscopic image by irradiating a radioactive ray to an image-capture target portion of a subject;

a catheter tip-end rotation angle calculation unit that performs a catheter tip-end rotation angle calculation process in which an offset angle between the operator's hand-side rotation angle detected by the catheter rotation angle detecting unit and a rotation angle of the catheter tip-end is calculated from an x-ray fluoroscopic image captured at a time of an action of rotating the catheter by one turn by the operator, based on respective angles of the bent portion and the base of the catheter in a state that the bent portion and the base are superposed and in a state that the bent portion and the base are deviated in the image processing unit and, during a catheter manipulation after ending the action of rotating the catheter by the one turn, the catheter tip-end rotation angle is calculated based on the offset angle and the operator's hand-side rotation angle; and an output unit that outputs the catheter tip-end rotation angle calculated by the catheter tip-end rotation angle calculation unit.

According to the 1st aspect, it is possible to understand the rotation angle (direction) of the catheter tip-end even in the body lumen such as a blood vessel of a complex shape, and it is possible to perform a smooth catheter manipulation.

2nd aspect: The catheter tip-end rotation angle detection apparatus according to the 1st aspect, comprising:

a user input unit to which a start of the catheter tip-end rotation angle calculation process by the catheter tip-end rotation angle calculation unit is input, wherein after the operator inputs the start of the catheter tip-end rotation angle calculation process to the user input unit, the catheter tip-end rotation angle calculation unit starts the catheter tip-end rotation angle calculation process.

According to the 2nd aspect, at a user input time, the user can understand the rotation angle (direction) of the catheter tip-end even in the body lumen such as a blood vessel of a complex shape, and the user can perform a smooth catheter manipulation.

3rd aspect: The catheter tip-end rotation angle detection apparatus according to the 1st aspect, comprising:

a capturing unit position/orientation acquisition unit that acquires position/orientation of the first x-ray fluoroscopic capturing unit and a second x-ray fluoroscopic capturing unit that captures an x-ray fluoroscopic image at a position different from a position of the first x-ray fluoroscopic capturing unit, when the first x-ray fluoroscopic capturing unit and the second x-ray fluoroscopic capturing unit capture x-ray fluoroscopic images, wherein the image processing unit extracts the catheter tip-end region from the respective x-ray fluoroscopic images of the first x-ray fluoroscopic capturing unit and the second x-ray fluoroscopic capturing unit.

4th aspect: The catheter tip-end rotation angle detection apparatus according to the 1st aspect, further comprising:

a catheter insertion amount detecting unit that detects an insertion amount of the catheter into the body lumen; and a detection condition deciding unit that, deciding whether the insertion amount of the catheter detected by the catheter insertion amount detecting unit changes, decides that the catheter tip-end rotation angle calculation unit performs the catheter tip-end rotation angle calculation process when the detection condition deciding unit decides that the insertion amount of the catheter does not change, and decides that the catheter tip-end rotation angle calculation unit does not perform the catheter tip-end rotation angle calculation process when the detection condition deciding unit decides that the insertion amount of the catheter changes.

According to the 4th aspect, even when the user does not perform a detection start input, the user can detect an accurate catheter tip-end rotation angle by only manipulating the catheter. Therefore, the user can perform a further smooth catheter manipulation and surgery by not performing the detection start input.

5th aspect: The catheter tip-end rotation angle detection apparatus according to the 1st aspect, further comprising:

a guide-wire insertion amount detecting unit that detects an insertion amount of a guide wire inserted into the body lumen, the guide wire having a bent portion at a tip-end which is bent in a hook shape relative to a straight-line shaped base, as a guide-wire tip-end region, movable in the catheter and inserted into the body lumen;

a guide-wire rotation angle calculation unit that detects a wire operator's hand-side rotation angle of the guide wire in an operator's hand; and a guide-wire tip-end rotation angle calculation unit that performs a guide-wire tip-end rotation angle calculation process in which an offset angle between the wire operator's hand-side rotation angle detected by the guide-wire rotation angle detecting unit and a rotation angle of the guide-wire tip-end is calculated from an x-ray fluoroscopic image captured at a time of an action of rotating the guide wire by one turn by the operator, based on respective angles of the bent portion and the base of the guide wire in a state that the bent portion and the base are superposed and in a state that the bent portion and the base of the guide wire are deviated in the image processing unit, and during a guide-wire manipulation after ending the action of rotating the guide wire by one turn, the guide-wire tip-end rotation angle is calculated based on the offset angle and the operator's hand-side rotation angle, wherein the image processing unit extracts a guide-wire tip-end region from the x-ray fluoroscopic image of the first x-ray fluoroscopic capturing unit, the catheter tip-end rotation angle detection apparatus further comprises:

a detection target switching unit that, by comparing the insertion amount of the guide wire detected by the guide-wire insertion amount detecting unit, the insertion amount of the catheter detected by the catheter insertion amount detecting unit, and a length of the catheter tip-end region, outputs a result of the image processing unit to the catheter tip-end rotation angle calculation unit by setting the catheter as a detection target when the insertion amount of the catheter is larger than a sum of the insertion amount of the guide wire and the length of the catheter tip-end region, and outputs a result of the image processing unit to the guide-wire tip-end rotation angle calculation unit by setting the guide wire as a detection target when the insertion amount of the catheter is smaller than a sum of the insertion amount of the guide wire and the length of the catheter tip-end region.

According to the 5th aspect, it is possible to detect tip-end rotation angles of the catheter and the guide wire respectively. Therefore, during the manipulation of the guide wire for making the catheter reach an affected part, or at the catheter manipulation time of directing a contrast medium to a target blood vessel, for example, the user can perform a smooth manipulation and surgery.

6th aspect: The catheter tip-end rotation angle detection apparatus according to the 3rd aspect, further comprising:

a detection condition deciding unit that decides that the bent portion of the catheter is extended in a straight-line shape when the catheter tip-end rotation angle calculation unit decides that the catheter tip-end region acquired from the respective x-ray fluoroscopic images of the first x-ray fluoroscopic capturing unit and the second x-ray fluoroscopic capturing unit is simultaneously in the superposed state, and decides that the catheter tip-end rotation angle calculation unit does not perform the catheter tip-end rotation angle calculation process.

According to the 6th aspect, a detection process can be omitted when the catheter is in a straight line state. Therefore, a surgery time can be shortened.

7th aspect: The catheter tip-end rotation angle detection apparatus according to the 1st aspect, wherein the output unit is a display unit that displays in a plane by a two-dimensional vector the catheter tip-end rotation angle calculated by the catheter tip-end rotation angle calculation unit.

According to the 7th aspect, because the operator can visually understand the catheter tip-end rotation angle (direction), the operator can perform a further smooth catheter manipulation.

8th aspect: The catheter tip-end rotation angle detection apparatus according to the 1st aspect, further comprising:

a catheter coordinate determination unit that calculates a catheter coordinate system, and a catheter tip-end rotation angle in a three-dimensional space from a catheter tip-end rotation angle calculated by the catheter tip-end rotation angle calculation unit, wherein the output unit has a three-dimensional shape model of the catheter, orientation-converts the three-dimensional shape model into the catheter tip-end rotation angle calculated by the catheter coordinate determination unit, and three-dimensionally displays an orientation-converted result.

According to the 8th aspect, even when a catheter rotation axis has an inclination at which it is difficult to understand by two-dimensional display, the operator can intuitively understand the catheter tip-end rotation angle (direction). Therefore, the operator can perform a further smooth catheter manipulation.

9th aspect: The catheter tip-end rotation angle detection apparatus according to the 8th aspect, wherein the output unit is a display unit that re-projects a catheter tip-end rotation angle in a vector looked at from an image-capture viewpoint of an x-ray fluoroscopic capturing unit, based on a catheter tip-end rotation angle in a three-dimensional space acquired by the catheter tip-end rotation angle calculation unit and image capture parameters acquired by the fluoroscopic capturing unit position/orientation acquisition unit, and that superposes and displays a catheter tip-end rotation angle at the image-capture viewpoint of the x-ray fluoroscopic capturing unit and a fluoroscopic image.

According to the 9th aspect, because a three-dimensional direction of the catheter can be displayed in superposition with the catheter during fluoroscopy, movement of a visual line can be reduced as compared with the case of displaying a three-dimensional model, and a further smooth catheter manipulation is possible.

10th aspect: A catheter tip-end rotation angle detection method for detecting a rotation angle around an axis of a bent portion of a catheter, the catheter having the bent portion at a tip-end that is bent in a hook shape relative to a straight-line shaped base, as a catheter tip-end region, and being inserted into a body lumen, the catheter tip-end rotation angle detection method comprising:

detecting by a catheter rotation angle detecting unit an operator's hand-side rotation angle of the catheter in a hand of an operator;

extracting by an image processing unit the catheter tip-end region from an x-ray fluoroscopic image of a first x-ray fluoroscopic capturing unit that captures an x-ray fluoroscopic image by irradiating a radioactive ray to an image-capture target portion of a subject;

performing a catheter tip-end rotation angle calculation process by a catheter tip-end rotation angle calculation unit, by calculating an offset angle between the operator's hand-side rotation angle detected by the catheter rotation angle detecting unit and a rotation angle of the catheter tip-end, from an x-ray fluoroscopic image captured at a time of an action of rotating the catheter by one turn by the operator, based on respective angles of the bent portion and the base of the catheter in a state that the bent portion and the base are superposed and in a state that the bent portion and the base are deviated in the image processing unit and, during a catheter manipulation after ending the action of rotating the catheter by the one turn, calculating the catheter tip-end rotation angle based on the offset angle and the operator's hand-side rotation angle; and outputting by an output unit the catheter tip-end rotation angle calculated by the catheter tip-end rotation angle calculation unit.

According to the 10th aspect, it is possible to understand the rotation angle (direction) of the catheter tip-end even in the body lumen such as a blood vessel of a complex shape, and it is possible to perform a smooth catheter manipulation.

11th aspect: A catheter tip-end rotation angle detection program for detecting a rotation angle around an axis of a bent portion of a catheter, the catheter having the bent portion at a tip-end that is bent in a hook shape relative to a straight-line shaped base, as a catheter tip-end region, and being inserted into a body lumen, the catheter tip-end rotation angle detection program makes a computer function as:

a catheter rotation angle detecting unit that detects an operator's hand-side rotation angle of the catheter in a hand of an operator;

an image processing unit that extracts the catheter tip-end region from an x-ray fluoroscopic image of a first x-ray fluoroscopic capturing unit that captures an x-ray fluoroscopic image by irradiating a radioactive ray to an image-capture target portion of a subject;

a catheter tip-end rotation angle calculation unit that performs a catheter tip-end rotation angle calculation process in which an offset angle between the operator's hand-side rotation angle detected by the catheter rotation angle detecting unit and a rotation angle of the catheter tip-end is calculated from an x-ray fluoroscopic image captured at a time of an action of rotating the catheter by one turn by the operator, based on respective angles of the bent portion and the base of the catheter in a state that the bent portion and the base are superposed and in a state that the bent portion and the base are deviated in the image processing unit and, during a catheter manipulation after ending the action of rotating the catheter by the one turn, the catheter tip-end rotation angle is calculated based on the offset angle and the operator's hand-side rotation angle; and an output unit that outputs the catheter tip-end rotation angle calculated by the catheter tip-end rotation angle calculation unit.

According to the 11th aspect, it is possible to understand the rotation angle (direction) of the catheter tip-end even in the body lumen such as a blood vessel of a complex shape, and it is possible to perform a smooth catheter manipulation.

Embodiments of the present invention are described below with reference to the drawings.

(First Embodiment)

FIG. 1 is a block diagram of a catheter tip-end rotation angle detection apparatus 100 according to a first embodiment of the present invention.

(Overall Configuration)

When a catheter 109 is started to be inserted into a body lumen such as a blood vessel, a rotation angle of the catheter 109 in the operator's hand detected by a catheter rotation angle detecting unit 106 and an actual catheter tip-end rotation angle are the same. However, during a period while the catheter 109 is inserted into the body lumen, that is, during a catheter manipulation, a difference occurs between the operator's hand-side rotation angle and the actual catheter tip-end rotation angle, due to a twist of the catheter 109. This difference is regarded as an offset and corrected. For this purpose, the catheter tip-end rotation angle detection apparatus 100 calculates an offset angle from the image of the catheter 109 that is rotated by one turn, based on input from a catheter operator (user) 110 as a start point.

The catheter tip-end rotation angle detection apparatus 100 includes a user input unit 108, a fluoroscopic capturing unit position/orientation acquisition unit 105, the catheter rotation angle detecting unit 106, an image processing unit 103, a catheter tip-end rotation angle calculation unit 104, and an output unit 107.

The user input unit 108 is a device by which the catheter operator 110 performs a start input of a catheter tip-end rotation angle calculation process.

The fluoroscopic capturing unit position/orientation acquisition unit 10 acquires the position and orientation of an image-capturing device of a first x-ray generating unit 101a described later of a first x-ray fluoroscopic capturing unit 101 when the first x-ray fluoroscopic capturing unit 101 has captured an x-ray fluoroscopic image. The first x-ray fluoroscopic capturing unit 101 is configured by the first x-ray generating unit 101a of the first x-ray fluoroscopic capturing unit 101 and a first x-ray detecting unit 101b that detects an x-ray generated by the first x-ray generating unit 101a, that are arranged to sandwich an image-capture target portion of a subject 111 such as a patient from above and below. The first x-ray detecting unit 101b is connected to the first x-ray generating unit 101a. A radiant ray (for example, an x-ray) is irradiated from the first x-ray generating unit 101a to the capture target portion of the patient 111 on a bed 180, and the first x-ray detecting unit 101b detects an x-ray image that is transmitted through the patient 111.

The catheter rotation angle detecting unit 106 detects an operator's hand-side rotation angle around the axis of the catheter 109 at a predetermined time interval, and stores the detected operator's hand-side rotation angle in an internal storage unit. At this time, to acquire a rotation angle related to the image, the operator's hand-side rotation angle is detected at the predetermined time interval by a synchronization signal.

The image processing unit 103 extracts a catheter tip-end region 109b from the x-ray fluoroscopic image of the first x-ray fluoroscopic capturing unit 101.

At the time of a catheter tip-end rotation angle calculation process, the catheter tip-end rotation angle calculation unit 104 calculates an offset angle between the operator's hand-side rotation angle and the catheter tip-end rotation angle, based on an angle at which the catheter tip-end becomes a straight line in the image processing unit 103, from the fluoroscopic image captured when the catheter operator 110 performs action to rotate the catheter 109 by one turn. After ending the detection process, during the catheter manipulation, the catheter tip-end rotation angle calculation unit 104 calculates the catheter tip-end rotation angle based on the offset angle and the operator's hand-side rotation angle.

As shown in FIGS. 2 and 3, the catheter 109 has a tip-end bent portion (that is, the catheter tip-end region) 109b that is bent in a hook shape relative to a base 109c in a straight line shape. The catheter tip-end rotation angle means a rotation angle around the axis of the bent portion (the catheter tip-end region) 109b of the tip-end of the catheter 109. The operator's hand-side rotation angle of the catheter means a rotation angle around the base in the straight line shape, that is, around the axis of a portion of the catheter at an operator's hand side. Further, a straight line referred to concerning whether the catheter tip-end region 109b is a straight line to be described later means a state that, from the x-ray fluoroscopic image captured when the catheter operator 110 manipulates the catheter 109 to rotate by one turn, a superposed state of the bent portion 109b and the base 109c of the catheter 109 is in a straight line or in substantially a straight line in the image processing unit 103.

The output unit 107 presents the catheter tip-end rotation angle (rotation angle) calculated by the catheter tip-end rotation angle calculation unit 104, to the catheter operator 110.

(Configuration of Each Block)

Each block is described in further detail.

(The User Input Unit 108)

The user input unit 108 is a device by which the user (catheter operator) performs a start input of a catheter tip-end rotation angle calculation process. For example, the user input unit 108 is a keyboard or a push button. A button or the like may be also used to urge to input a start of the catheter tip-end rotation angle calculation process. When the user input unit 108 receives an input to start the catheter tip-end rotation angle calculation process, a catheter tip-end rotation angle calculation process start command is output from the user input unit 108 to the image processing unit 103.

(The fluoroscopic capturing unit position/orientation acquisition unit 105)

The fluoroscopic capturing unit position/orientation acquisition unit 105 acquires the parameters when the first x-ray fluoroscopic capturing unit 101 has captured an x-ray fluoroscopic image, and outputs the acquired parameters to the catheter tip-end rotation angle calculation unit 104.

Image capture parameters to be handled by the fluoroscopic capturing unit position/orientation acquisition unit 105 include a camera parameter (or referred to as an internal parameter) of the first x-ray fluoroscopic capturing unit 101, and position/orientation information (or referred to as an external parameter) of the first x-ray fluoroscopic capturing unit 101 at the time of image-capturing by the first x-ray fluoroscopic capturing 101. The internal parameter has information of a focal distance and the like of an image-capturing lens of the first x-ray fluoroscopic capturing unit 101, and is expressed by Equation (1).

$$A = \begin{bmatrix} fk_u & fk_s & u_0 \\ 0 & fk_v & v_0 \\ 0 & 0 & 1 \end{bmatrix} \quad (1)$$

Here, f represents a focal distance of the capturing lens of the first x-ray fluoroscopic capturing unit 101, $k_u$ represents a scale factor of a u-direction (horizontal direction), $k_v$ represents a scale factor of a v direction (vertical direction), $k_s$ represents a shear factor, and $(u_0, v_0)$ represents image center coordinates.

On the other hand, position/orientation (external parameter) M has information of a rotation matrix R and a translation matrix T as shown by Equation (2).

$$M = \begin{bmatrix} R & T \\ 0^T & 1 \end{bmatrix} \quad (2)$$

Here, the rotation matrix R is as follows.

$$R = \begin{bmatrix} 1 & 0 & 0 \\ 0 & \cos\theta_x & -\sin\theta_x \\ 0 & \sin\theta_x & \cos\theta_x \end{bmatrix} \begin{bmatrix} \cos\theta_y & 0 & \sin\theta_y \\ 0 & 1 & 0 \\ -\sin\theta_y & 0 & \cos\theta_y \end{bmatrix} \begin{bmatrix} \cos\theta_z & -\sin\theta_z & 0 \\ \sin\theta_z & \cos\theta_z & 0 \\ 0 & 0 & 1 \end{bmatrix} \quad (3)$$

In addition, the translation matrix T is as follows.

$$T = \begin{bmatrix} T_x \\ T_y \\ T_z \end{bmatrix} \quad (4)$$

Here, $\theta_x$ represents a rotation angle around an x-axis, $\theta_y$ represents a rotation angle around a y-axis, $\theta z$ represents a rotation angle around a z-axis, $T_x$ represents a translation of an x-axis direction, $T_y$ represents a translation of a y-axis direction, and $T_z$ represents a translation of a z-axis direction.

Further, a fluoroscopic projection matrix P obtained by transforming the internal parameter, the external parameter, or a combination of the internal parameter and the external parameter in Equation (5) is output from the fluoroscopic capturing unit position/orientation acquisition unit 105 to the catheter tip-end rotation angle calculation unit 104.

$$P = AP_f M \quad (5)$$

where $$P_f = \begin{bmatrix} 1 & 0 & 0 & 0 \\ 0 & 1 & 0 & 0 \\ 0 & 0 & 1 & 0 \end{bmatrix} \quad (6)$$

(The Catheter Rotation Angle Detecting Unit 106)

Figure 4B:
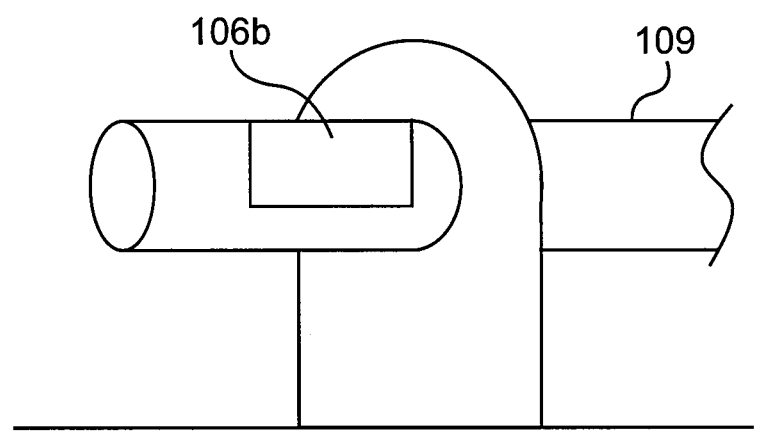
FIG. 4B is an explanatory view of another example of a catheter rotation angle detecting unit.
Figure 8:
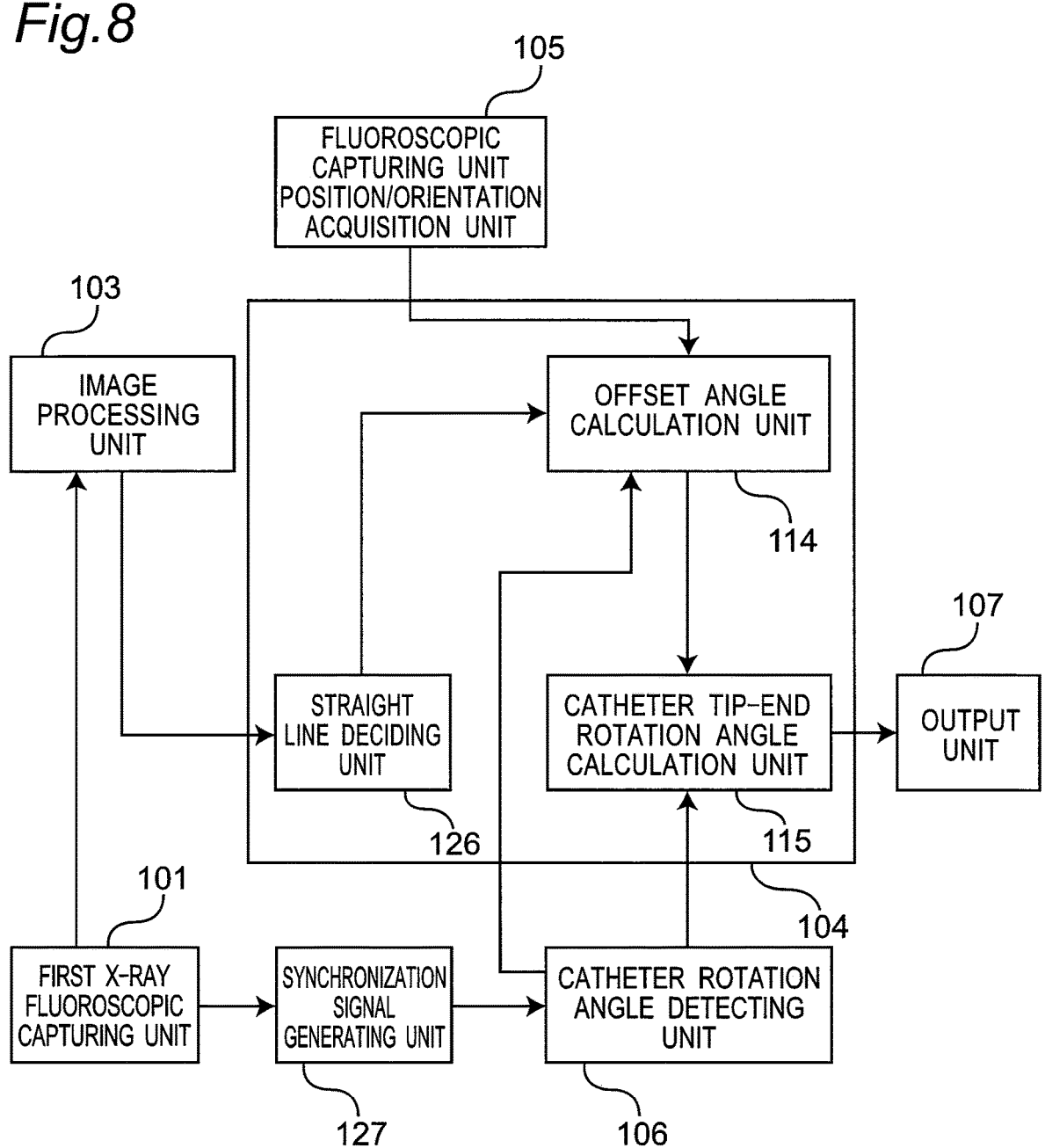
FIG. 8 is a detailed functional block diagram of a catheter tip-end rotation angle calculation unit.

The catheter rotation angle detecting unit 106 is a device that detects a rotation angle of the catheter in the catheter operator's hand (operator's hand-side rotation angle) As a method of detecting a catheter rotation angle by the catheter rotation angle detecting unit 106, a rotation angle may be detected at each predetermined interval, for example. As another example, the catheter rotation angle detecting unit 106 may receive a synchronization signal from a synchronization signal generating unit 127 shown in FIG. 8, and measure an angle synchronized with the fluoroscopic image captured by the first x-ray fluoroscopic capturing unit 101. The synchronization signal generating unit 127 generates a synchronization signal corresponding to the fluoroscopic image captured by the first x-ray fluoroscopic capturing unit 101, and outputs the generated synchronization signal to the catheter rotation angle detecting unit 106, as shown in FIG. 8. The catheter rotation angle detecting unit 106 may apply patterns 109*a* to the catheter 109, and measure a rotation angle by capturing the patterns 109*a* with a camera 106*a*, as shown in FIG. 4A, for example. As another example of the catheter rotation angle detecting unit 106, a rotation angle may be measured by using a rotation angle sensor like a rotary encoder 106*b*, as shown in FIG. 4B.

(The Image Processing Unit 103)

The image processing unit 103 receives the catheter tip-end rotation angle calculation process start command from the user input unit 108, receives the detected rotation angle of the catheter in the catheter operator's hand from the catheter rotation angle detecting unit 106, and acquires the x-ray fluoroscopic image from the first x-ray fluoroscopic capturing unit 101. The image processing unit 103 extracts the catheter tip-end region 109*b* from the x-ray fluoroscopic image, based on the catheter rotation angle and the x-ray fluoroscopic image, and outputs the extraction result to the catheter tip-end rotation angle calculation unit 104.

The catheter tip-end region 109*b* is a bent region at the tip-end of the catheter 109, and refers to a region of a few centimeters of the tip-end of the catheter 109, although the size of the region varies depending on a surgery site and is different among the catheters for a coronary bypass, for an internal thoracic artery graft, and for others. For the catheter tip-end region 109*b*, an image of the catheter tip-end region 109*b* before inserting the catheter may be stored in advance in the storage unit incorporated in the image processing unit 103, and the catheter tip-end region 109*b* may be extracted from a difference image between the stored image and the image at current time (detection time). Alternatively, the catheter tip-end region 109*b* may be extracted by performing a process of extracting a line region from an image like a line emphasis filter.

(The Catheter Tip-End Rotation Angle Calculation Unit 104)

The catheter tip-end rotation angle calculation unit 104 receives the extraction result of the catheter tip-end region 109*b* from the image processing unit 103, receives the image capture parameters of the first x-ray fluoroscopic capturing unit 101 from the fluoroscopic capturing unit position/orientation acquisition unit 105, and receives the operator's hand-side rotation angle from the catheter rotation angle detecting unit 106. The catheter tip-end rotation angle calculation unit 104 decides whether the catheter tip-end region 109*b* is a straight line, based on the extraction result of the catheter tip-end region 109*b*, the image capture parameters, and the operator's hand-side rotation angle. When the catheter tip-end rotation angle calculation unit 104 has decided that the catheter tip-end region 109*b* is a straight line, the catheter tip-end rotation angle calculation unit 104 calculates a catheter rotation axis and a catheter coordinate system, from the catheter tip-end region 109*b* and the image capture parameters. At the same time, the catheter tip-end rotation angle calculation unit 104 calculates an offset angle between a catheter tip-end rotation angle at this time and the operator's hand-side rotation angle based on the catheter tip-end rotation angle. After calculating the offset angle, the catheter tip-end rotation angle calculation unit 104 calculates the catheter tip-end rotation angle, from the offset angle and the operator's hand-side rotation angle, and outputs a result of the calculation to the output unit 107.

The catheter tip-end rotation angle calculation unit 104 includes a straight line deciding unit 126, an offset angle calculation unit 114, and a catheter tip-end rotation angle calculation unit 115. A process of the catheter tip-end rotation angle calculation unit 104 is described in detail below with reference to the block diagram in FIG. 1.

(The Straight Line Deciding Unit 126)

The straight line deciding unit 126 receives the extraction result of the catheter tip-end region 109*b* from the image processing unit 103. The straight line deciding unit 126 decides whether the catheter tip-end region 109*b* is a straight line, based on the extraction result of the catheter tip-end region 109*b*. The straight line deciding unit 126 outputs a decision result of whether the catheter tip-end region 109*b* is a straight line and the extraction result of the catheter tip-end region 109*b*, to the offset angle calculation unit 114. For the decision about whether the catheter tip-end region 109*b* is a straight line, a pattern matching method can be used. For example, a shape of a state that the catheter tip-end region 109*b* is a straight line or is substantially a straight line is stored in advance in the storage unit incorporated in the straight line deciding unit 126. Then, it is decided whether the catheter tip-end region 109*b* is a straight line, by pattern matching.

(The Offset Angle Calculation Unit 114)

The offset angle calculation unit 114 calculates an offset angle between the rotation angle of the catheter rotation angle detecting unit 106 and the catheter tip-end rotation angle, based on the straight line decision result and the operator's hand-side rotation angle. The offset angle calculation unit 114 receives the straight line decision result from the straight line deciding unit 126, and receives the operator's hand-side rotation angle from the catheter rotation angle detecting unit 106. When the decision result is a straight line, the offset angle calculation unit 114 calculates the offset angle by using a value of the catheter rotation angle detecting unit 106 as the offset angle, and outputs the offset angle to the catheter tip-end rotation angle calculation unit 115.

(The Catheter Tip-End Rotation Angle Calculation Unit 115)

The catheter tip-end rotation angle calculation unit 115 calculates a catheter tip-end rotation angle, based on the offset angle and the operator's hand-side rotation angle. The catheter tip-end rotation angle calculation unit 115 receives the offset angle from the offset angle calculation unit 114, and receives the operator's hand-side rotation angle from the catheter rotation angle detecting unit 106.

When the operator's hand-side rotation angle acquired from the catheter rotation angle detecting unit 106 has changed from a rotation angle at the last detection time, the catheter tip-end rotation angle calculation unit 115 calculates a catheter tip-end rotation angle at current time (detection time), from the operator's hand-side rotation angle and the offset angle, and outputs a calculation result to the output unit 107.

(The Output Unit 107)

The output unit 107 is a device that presents a catheter tip-end rotation angle to the catheter operator 110, based on the catheter tip-end rotation angle from the catheter tip-end rotation angle calculation unit 115. The output unit 107 corresponds to a display unit such as a television and a display.

(A Utilization Form of the Catheter Tip-End Rotation Angle Detection Apparatus)

FIG. 2 shows a configuration and a utilization scene of the catheter tip-end rotation angle detection apparatus 100 according to the first embodiment. FIG. 3 shows a configuration and a utilization scene of the catheter tip-end rotation angle detection apparatus 100 according to a modification example of the first embodiment. FIG. 2 and FIG. 3 are different in that whether only one first x-ray fluoroscopic capturing unit 101 is used for capturing or two x-ray fluoroscopic capturing units including the first x-ray fluoroscopic capturing unit 101 and a second x-ray fluoroscopic capturing unit 102 are used for capturing. A case of using both the first x-ray fluoroscopic capturing unit 101 and the second x-ray fluoroscopic capturing unit 102 can be used for three-dimensional display as described later.

The catheter tip-end rotation angle detection apparatus 100 includes the user input unit 108, the catheter rotation angle detecting unit 106, and the output unit 107. The catheter tip-end rotation angle detection apparatus 100 starts a detection process when the operator has performed a start input to the user input unit 108. FIGS. 2 and 3 exemplify a case that the user input unit 108 is a push button. After the operator pushes the push button to perform a start input to the user input unit 108, the catheter operator 110 manipulates the catheter 109 to rotate by one turn around the axis of the catheter 109. The first x-ray fluoroscopic capturing unit 101 captures a fluoroscopic image at this time, and the catheter tip-end rotation angle calculation unit 104 detects the offset angle, based on a rotation angle of the catheter rotation angle detecting unit 106 at the operator's hand. The second x-ray fluoroscopic capturing unit 102 has a structure similar to that of the first x-ray fluoroscopic capturing unit 101, and only arrangement of the second x-ray fluoroscopic capturing unit 102 is different from that of the first x-ray fluoroscopic capturing unit 101. That is, the second x-ray fluoroscopic capturing unit 102 is configured by a second x-ray generating unit 102a of the second x-ray fluoroscopic capturing unit 102 and a second x-ray detecting unit 102b that detects an x-ray generated by the second x-ray generating unit 102a, that are arranged to sandwich an image-capture target portion of the patient 111 from above and below. The second x-ray detecting unit 102b is connected to the second x-ray generating unit 102a. A radiant ray (for example, an x-ray) is irradiated from the second x-ray generating unit 102a in a direction different from that of the first x-ray generating unit 101a to the capture target portion of the patient 111 on the bed 180, and the second x-ray detecting unit 102b detects an x-ray image that is transmitted from the second x-ray generating unit 102a through the patient 111.

After the offset angle detection process, the catheter tip-end rotation angle calculation unit 104 calculates the catheter tip-end rotation angle, based on the offset angle and the operator's hand-side rotation angle. The output unit 107 (a display, for example) displays the calculation result from the catheter tip-end rotation angle calculation unit 104. FIGS. 2 and 3 exemplify a case that a display 107a two-dimensionally displays the catheter tip-end rotation angle (an angle is referred to by an arrow direction from a center of a cross in a circle at a right lower part on the screen of the display 107a in FIGS. 2 and 3). In this case, an example that an operator direction is downward and that an angle relative to the rotation axis is presented as a two-dimensional vector is shown. Based on this, the operator can understand the direction of the catheter tip-end from the fluoroscopic image that is projected as a two-dimensional image.

(A Process Flow of the Catheter Tip-End Rotation Angle Detection Apparatus (First Embodiment))

A procedure of an operator workflow of the catheter tip-end rotation angle calculation process is described with reference to a flowchart in FIG. 5.

First, step S600 is a step in which the catheter operator 110 inserts the catheter 109 into a body lumen such as a blood vessel of the patient 111. In this step, the catheter rotation angle detecting unit 106 calculates at a predetermined time interval an operator's hand-side rotation angle at a catheter manipulation time, based on an angle at a catheter insertion time, and stores the calculated angle into the internal storage unit of the catheter rotation angle detecting unit 106.

Next, in step S700, the catheter operator 110 performs a catheter manipulation of inserting the catheter 109 into a specific blood vessel. By using the catheter 109, the catheter operator 110 injects a contrast medium into the specific blood vessel and checks for the disease attributable to stenosis or blockage of the blood vessel. At the time of checking for the disease, contrast radiography and the like of an inspection target blood vessel is also performed.

Next, step S800 is a step in which the catheter operator 110 decides whether the inspection has ended. When the contrast radiography of the inspection target blood vessel has not ended, it is decided that the inspection has not ended, and the process proceeds to step S900. When the contrast radiography of the inspection target blood vessel has ended, it is decided that the inspection has ended, and the process proceeds to step S1100.

Step S900 is a step in which the catheter operator 110 decides whether detection of a catheter tip-end rotation angle is necessary. When the catheter operator 110 decides that detection of a catheter tip-end rotation angle is necessary, the process proceeds to step S1000. At this time, as a specified operation in the first embodiment, the catheter operator 110 performs a start input of detecting the catheter tip-end rotation angle, by pushing the push button as an example of the user input unit 108. When the catheter operator 110 decides that detection of a catheter tip-end rotation angle is not necessary, the process returns to step S700.

In step S1000, the catheter operator 110 manipulates the catheter 109 to rotate by one turn around the axis of the catheter 109. The catheter tip-end rotation angle detection apparatus 100 detects the catheter tip-end rotation angle, through the image processing by the image processing unit 103 and the calculation of the catheter tip-end rotation angle by the catheter tip-end rotation angle calculation unit 104 (see the catheter tip-end rotation angle calculation process in FIG. 6), from the fluoroscopic image captured by the first x-ray fluoroscopic capturing unit 101 at the time of a one-turn manipulation by the catheter operator 110 and from the operator's hand-side rotation angle detected by the catheter rotation angle detecting unit 106. After the catheter tip-end rotation angle detection, the process returns to step S700 of performing a catheter manipulation.

Step S1100 is a step of removing the catheter 109 from the blood vessel. The catheter operator 110 removes the catheter 109 from the blood vessel, and the catheter contrast radiography ends.

(An Overall Process Flow)

Figure 6:
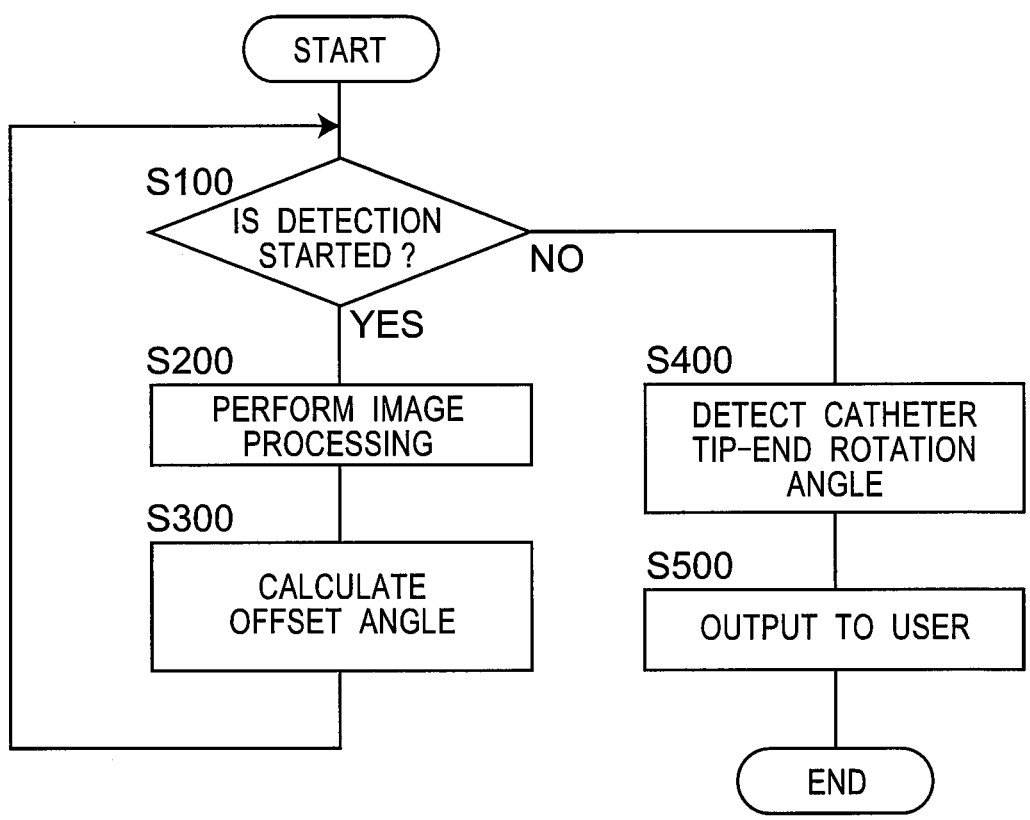
FIG. 6 is a view showing an overall process flow of a catheter tip-end rotation angle detection.

A procedure of an overall process of the catheter tip-end rotation angle calculation process performed in step S1000 by the catheter tip-end rotation angle detection apparatus 100 is described by using the flowchart in FIG. 6

First, step S100 is a step of deciding whether the detection is started. Specifically, when the image processing unit 103 decides that there is a detection start input to the user input unit 108, the overall process flow proceeds to step S200 in which the image processing unit 103 extracts the catheter tip-end region 109b. In the first embodiment, the image processing unit 103 decides that the catheter operator 110 has pushed the push button as an example of the user input unit 108, so that the image processing unit 103 decides that there is a detection start input of the catheter tip-end rotation angle. When the image processing unit 103 decides that there is not a detection start input to the user input unit 108, in the overall process flow, the image processing unit 103 refers to an offset angle detected before, and the process proceeds to step S400 of detecting the catheter tip-end rotation angle. In the first embodiment, when the image processing unit 103 decides that the catheter operator 110 has not pushed the push button as an example of the user input unit 108, the image processing unit 103 decides that there is not a detection start input of the catheter tip-end rotation angle. That the image processing unit 103 refers to the offset angle detected before and detects the catheter tip-end rotation angle means that the offset angle detected in the past is used as it is until a correction process is performed anew. The image processing unit 103 refers to the offset angle detected before and to detect the catheter tip-end rotation angle, and afterward, updates the catheter tip-end rotation angle. When there is no offset angle detected in the past, it is assumed that the operator's hand-side rotation angle and the catheter tip-end rotation angle are the same (offset angle=0 degrees). That there is an offset angle detected before means that when a correction process has been performed at a plurality of times, at a second time or later, there is an offset angle detected before.

In step S200, the image processing unit 103 extracts the catheter tip-end region 109b from the x-ray fluoroscopic image of the first x-ray fluoroscopic capturing unit 101. Specifically, the image processing unit 103 extracts the catheter tip-end region 109b from the x-ray fluoroscopic image acquired by the image processing unit 103 from the first x-ray fluoroscopic capturing unit 101. As a method of extracting the catheter tip-end region 109b from the x-ray fluoroscopic image by the image processing unit 103, there can be used the pattern matching method. A shape of the catheter tip-end region 109b is stored in advance in the storage unit incorporated in the image processing unit 103. Then, the catheter tip-end region 109b is extracted by pattern matching. Thereafter, the overall process flow proceeds to step S300.

Next, in step S300, the catheter tip-end rotation angle calculation unit 104 calculates the offset angle between the operator's hand-side rotation angle and the catheter tip-end rotation angle, based on a result of the catheter tip-end region 109b extracted by the image processing unit 103. After ending the process in step S300, the overall process flow returns to step S100.

In step S400, the catheter tip-end rotation angle calculation unit 104 detects the catheter tip-end rotation angle, based on the offset angle calculated in step S300.

Next, in step S500, the catheter tip-end rotation angle calculation unit 104 acquires the catheter coordinates calculated in step S300 (specifically, step S308 described later) and a catheter tip-end rotation angle calculated in step S400 (specifically step S403 described later), and displays the acquired result for the catheter operator 110 in the output unit 107. Then, the overall process flow ends.

Detailed processes in main steps are described below.

(The Process in Step S200)

Figure 7:
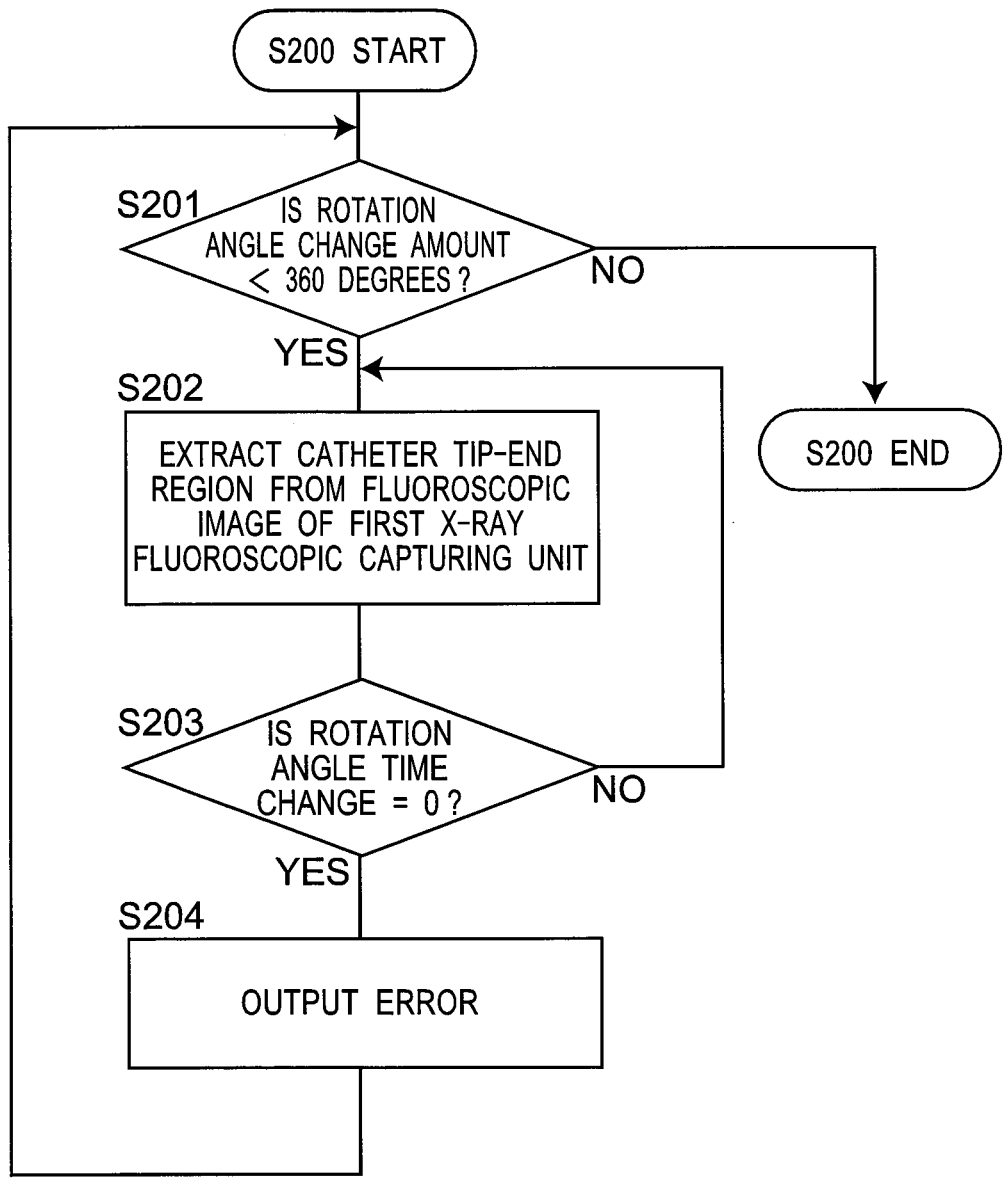
FIG. 7 is a view showing a process flow of an image processing S200.

The process in step S200 is described in detail with reference to a flowchart in FIG. 7. The process in step S200 is a process in which the image processing unit 103 extracts the catheter tip-end region 109b from the x-ray fluoroscopic image of the first x-ray fluoroscopic capturing unit 101. FIG. 7 shows the process at each time of a synchronization signal.

First, step S201 is a step in which the image processing unit 103 decides whether a change amount of the operator's hand-side rotation angle is less than 360 degrees after the detection start input. That is, step S201 is a step in which the image processing unit 103 decides whether the catheter operator 110 has rotated the catheter 109 by one turn around the axis of the catheter 109 in the preceding step S100. When the image processing unit 103 decides that the catheter 109 has rotated by less than one turn around the axis of the catheter 109, that is, a change amount of a rotation angle of the catheter 109 is less than 360 degrees, the process proceeds to step S202. When the image processing unit 103 decides that the catheter 109 has rotated by one turn or more than one turn around the axis of the catheter 109, that is, a change amount of a rotation angle of the catheter 109 is equal to or more than 360 degrees, the image processing unit 103 does not perform the extraction process of the catheter tip-end region 109b, and ends the process in step S200. In this way, when the catheter has rotated by 360 degrees or more, this means that the process of the image processing unit ends by assuming that the user has manipulated the catheter to rotate by one turn.

In step S202, the image processing unit 103 extracts the catheter tip-end region 109b from the fluoroscopic image of the first x-ray fluoroscopic capturing unit 101, by the pattern matching method or the like.

Next, in step S203, the image processing unit 103 decides whether there is a time change of a rotation angle. When the image processing unit 103 decides that there is a rotation angle change amount by a certain predetermined amount or more during a predetermined time, the process proceeds to step S202. When the image processing unit 103 decides that there is not a rotation angle change amount by a certain amount or more during a predetermined time, the image processing unit 103 decides that the catheter operator 110 has ended the manipulation without rotating the catheter 109 by 360 degrees, and the process proceeds to step S204. Therefore, an error display is performed in step S204 depending on whether the catheter operator 110 has rotated the catheter 109 by 360 degrees in step S203, or an error display is performed in step S204 on the way of rotation when it is decided in step S203 that there is no rotation angle time change during a predetermined time.

In step S204, the error output is performed to alarm the catheter operator 110 so that the catheter operator 110 manipulates the catheter to rotate by 360 degrees or more. The error output in this case means that an alarm of, for example, "Please rotate by one turn or more" is displayed or an alarm lamp is lit.

(The Process in Step S300)

An offset angle calculation process in step S300 is described in detail with reference to a flowchart in FIG. 9. The process in step S300 is a process in which the catheter tip-end rotation angle calculation unit 104 calculates the offset angle between the operator's hand-side rotation angle and the catheter tip-end rotation angle.

First, step S301 is a step in which the straight line deciding unit 126 decides linearity of the catheter tip-end region 109b extracted from the fluoroscopic image of the first x-ray fluoroscopic capturing unit 101 in step S202. When the straight line deciding unit 126 decides that the catheter tip-end region 109 is a straight line, the offset angle calculation process proceeds to step S309. When the straight line deciding unit 126 decides that the catheter tip-end region 109 is not a straight line, a subsequent offset angle calculation process is not performed. That is, when the image cannot be decided as a straight line, the offset angle cannot be calculated, and therefore, the subsequent offset angle calculation process is not performed. The reason is that because when the input image is the same, a linearity detection cannot be performed even when an offset angle is detected again in a predetermined time. An error output may be performed again to urge the user to perform a rotation manipulation again.

Next, in step S309, the catheter rotation angle detecting unit 106 calculates the operator's hand-side rotation angle when linearity of the catheter tip-end region 109b is decided in step S301. Thereafter, the offset angle calculation process proceeds to step S311.

Next, in step S311, the offset angle calculation unit 114 calculates the offset angle between the operator's hand-side rotation angle calculated in step S309 and the catheter tip-end rotation angle, based on the information of a correspondence relation between the image and the operator's hand-side rotation angle. FIGS. 10A and 10B are views showing outlines of the offset value calculation. FIG. 10A shows a correspondence table between an image and an operator's hand-side rotation angle stored in the storage unit incorporated in the offset angle calculation unit 114. As shown in FIG. 10A, a relation between an image and an operator's hand-side rotation angle is related to 0 degrees and 180 degrees. When the catheter has been rotated by one turn, the catheter rotation angle detecting unit 106 calculates the operator's hand-side rotation angle when linearity is decided in step S309. Therefore, the offset angle calculation unit 114 obtains a correspondence relation between an image and an operator's hand-side rotation angle at current time (detection time) as shown in FIG. 10B. The offset angle is a difference value between an operator's hand-side rotation angle that is related in advance and the operator's hand-side rotation angle currently acquired. In the case of FIG. 10B, the offset angle is 10 degrees.

In this case, to relate the image with the operator's hand-side rotation angle, a rotation direction of the catheter 109 is necessary. The catheter tip-end rotation angle detection apparatus 100 may instruct the rotation direction to the catheter operator 110, or the rotation direction may be detected from the image. For example, to detect the rotation direction from the image, the offset angle calculation unit 114 extracts difference regions of the image at a plurality of times, and the offset angle calculation unit 114 calculates a moved direction of the tip-end region 109b of the catheter 109.

After the offset angle is calculated in this way, the offset angle calculation process ends.

(The Process in Step S400)

The process in step S400 is described in detail with reference to a flowchart in FIG. 11. The process in step S400 is a process in which the catheter tip-end rotation angle calculation unit 104 calculates the catheter tip-end rotation angle. Thereafter, the catheter tip-end rotation angle calculation process proceeds to step S401.

First, in step S401, the catheter tip-end rotation angle calculation unit 115 acquires the operator's hand-side rotation angle detected by the catheter rotation angle detecting unit 106. Thereafter, the catheter tip-end rotation angle calculation process proceeds to step S402.

Next, in step S402, the catheter tip-end rotation angle calculation unit 115 acquires the offset angle between the operator's hand-side rotation angle and the catheter tip-end rotation angle calculated in step S311, from the offset angle calculation unit 114. Thereafter, the catheter tip-end rotation angle calculation process proceeds to step S403.

Next, in step S403, the catheter tip-end rotation angle calculation unit 115 calculates the catheter tip-end rotation angle corresponding to the operator's hand-side rotation angle at current time (detection time), from the operator's hand-side rotation angle and the offset angle acquired in step S401 and step S402, respectively. Thereafter, the catheter tip-end rotation angle calculation process ends.

(An Effect of the First Embodiment)

According to the catheter tip-end rotation angle detection apparatus 100 in the first embodiment, the catheter operator 110 can detect a catheter tip-end rotation angle by rotating the catheter 109 by only one turn, without setting a special marker in the catheter 109, in an environment that the direction of the catheter at the insertion time and the catheter tip-end rotation angle at current time (detection time) are different. Therefore, the user can smoothly perform a catheter manipulation and surgery.

(Second Embodiment)

In the first embodiment, the method of detecting an angle of a catheter tip-end is described. According to this method, the catheter tip-end rotation angle at current time (detection time) can be presented. Therefore, the catheter operator 110 can perform surgery while understanding the tip-end angle. However, according to the present two-eye capturing device (biplane fluoroscopic capturing unit), an image captured with a large angle difference is presented directly to the catheter operator 110. Therefore, there is a problem in that because the catheter operator 110 cannot easily understand a spatial positional relation, it takes time to manipulate the catheter.

Accordingly, for the catheter operator 110 to intuitively manipulate the catheter, it is preferable that a catheter tip-end rotation angle (direction) is presented three-dimensionally. In a second embodiment, an operation of a catheter tip-end rotation angle detection apparatus 100B that enables a catheter coordinate determination unit 113 to three-dimensionally present a catheter tip-end rotation angle (direction) is described.

Figure 12:
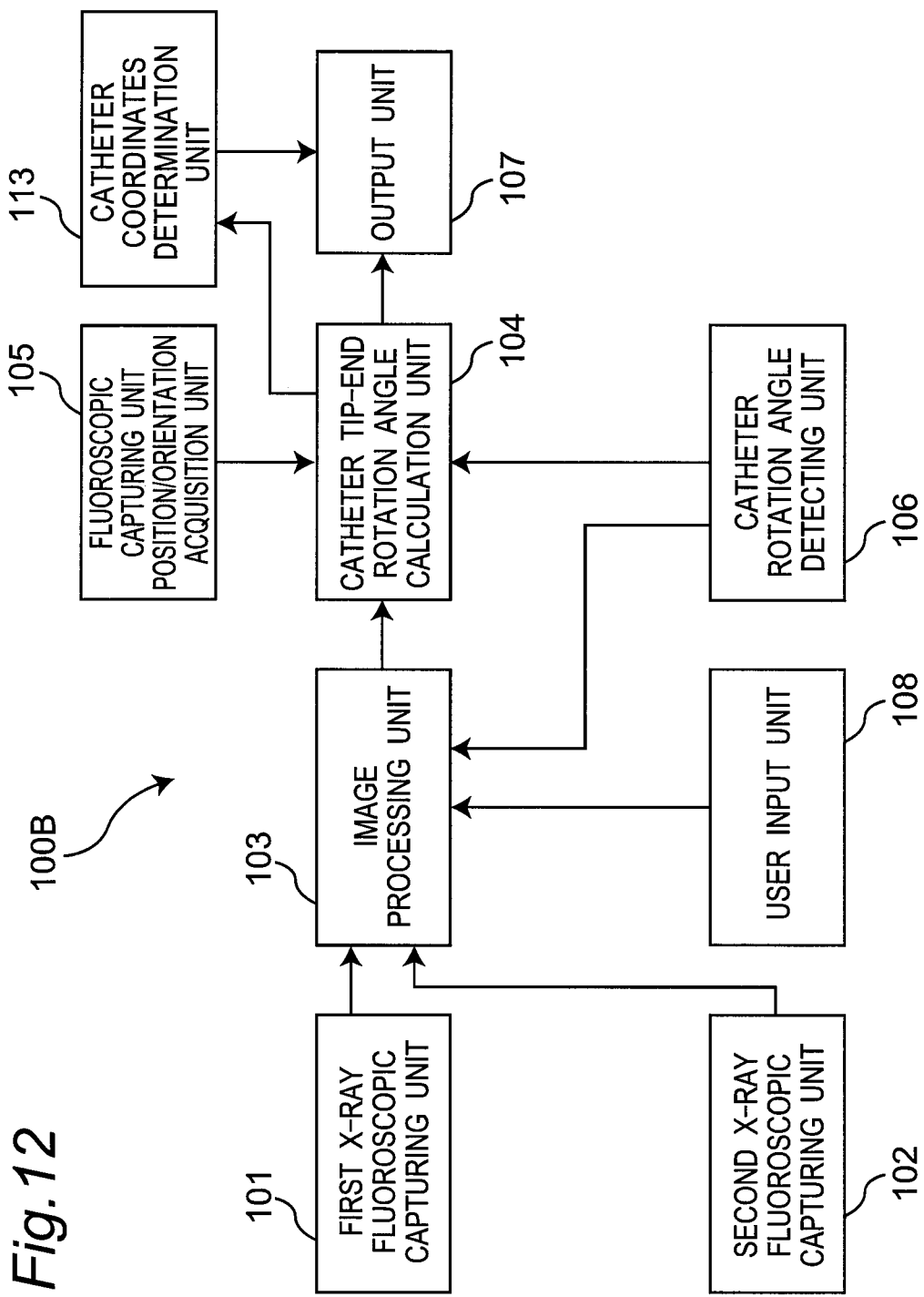
FIG. 12 is a configuration view of functional blocks of a catheter tip-end rotation angle detection apparatus according to a second embodiment of the present invention.

FIG. 12 shows a block diagram of the catheter tip-end rotation angle detection apparatus 100B according to the second embodiment. Descriptions of constituent elements that are the same as those of the first embodiment are omitted. Hereinafter, operations of units relating to the second embodiment of the present invention are described.

The catheter tip-end rotation angle detection apparatus 100B according to the second embodiment includes the catheter coordinate determination unit 113 in addition to the constituent elements of the first embodiment.

Each block is described in detail below.

(The Catheter Coordinate Determination Unit 113)

Figure 13:
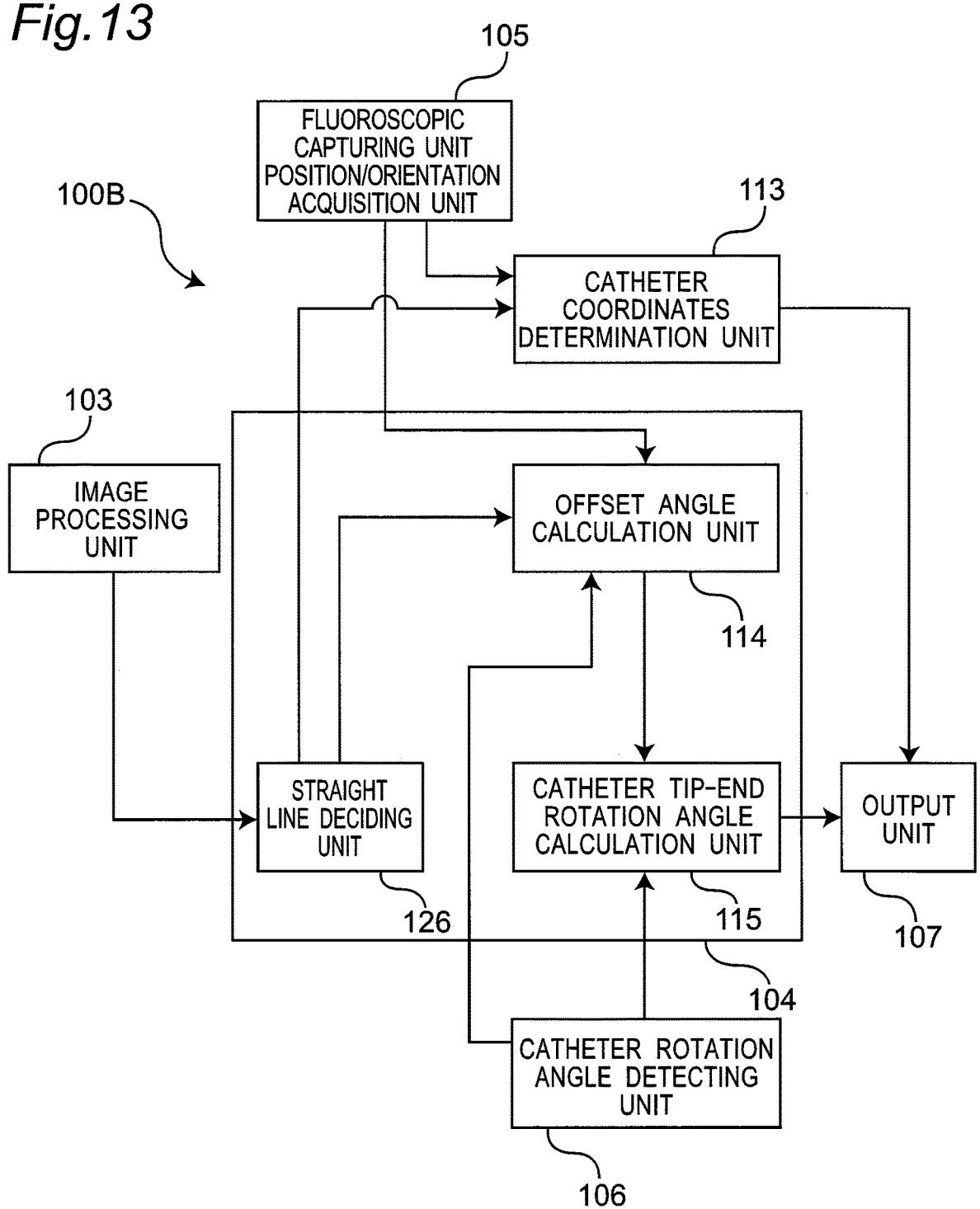
FIG. 13 is a view showing a detailed configuration of a catheter tip-end rotation angle detecting unit of the catheter tip-end rotation angle detection apparatus in FIG. 12.

The catheter coordinate determination unit 113 is described with reference to FIG. 13. The catheter coordinate determination unit 113 calculates a catheter coordinate system serving as a standard of a catheter tip-end rotation angle, based on a straight line decision result, the catheter tip-end region 109b, and image capture parameters. The catheter coordinate determination unit 113 receives the straight line decision result and an extraction result of the catheter tip-end region 109b from the straight line deciding unit 126, and receives the image capture parameters of the first x-ray fluoroscopic capturing unit 101 from the fluoroscopic capturing unit position/orientation acquisition unit 105. When the straight line deciding unit 126 decides that the catheter tip-end region 109b is a straight line, the catheter coordinate determination unit 113 calculates the catheter coordinate system, from the straight line region and the image capture parameters of two fluoroscopic images.

Figure 14A:
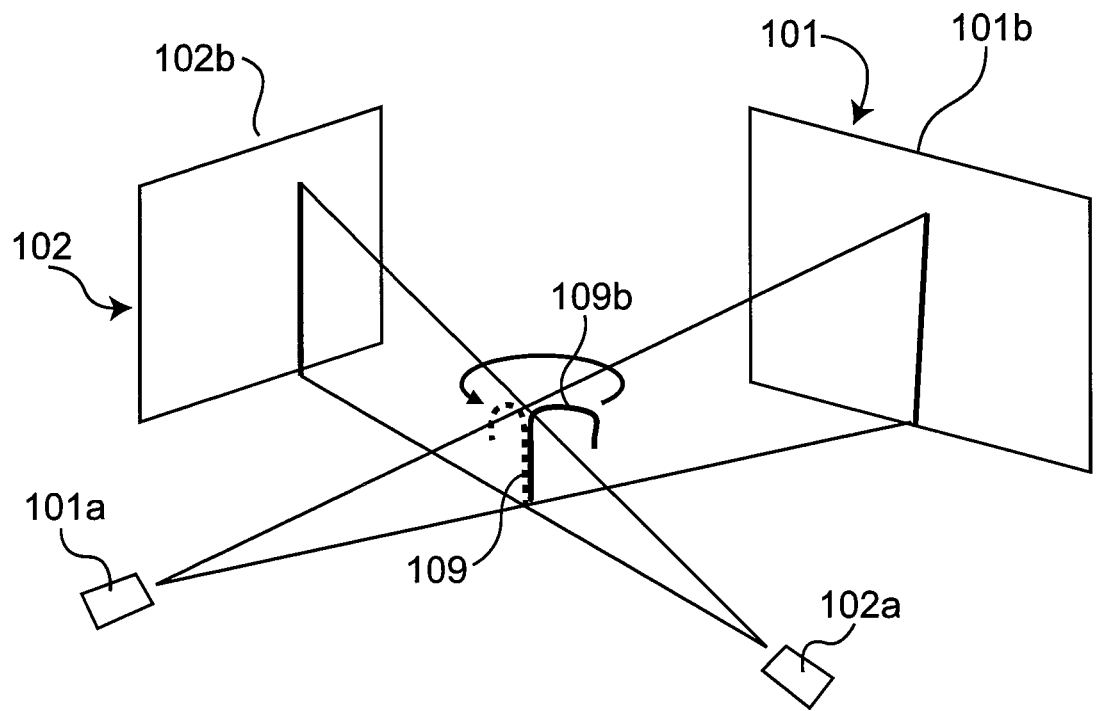
FIG. 14A is a relational view between the catheter and an x-ray fluoroscopic capturing unit at a catheter coordinate calculation time.
Figure 14B:
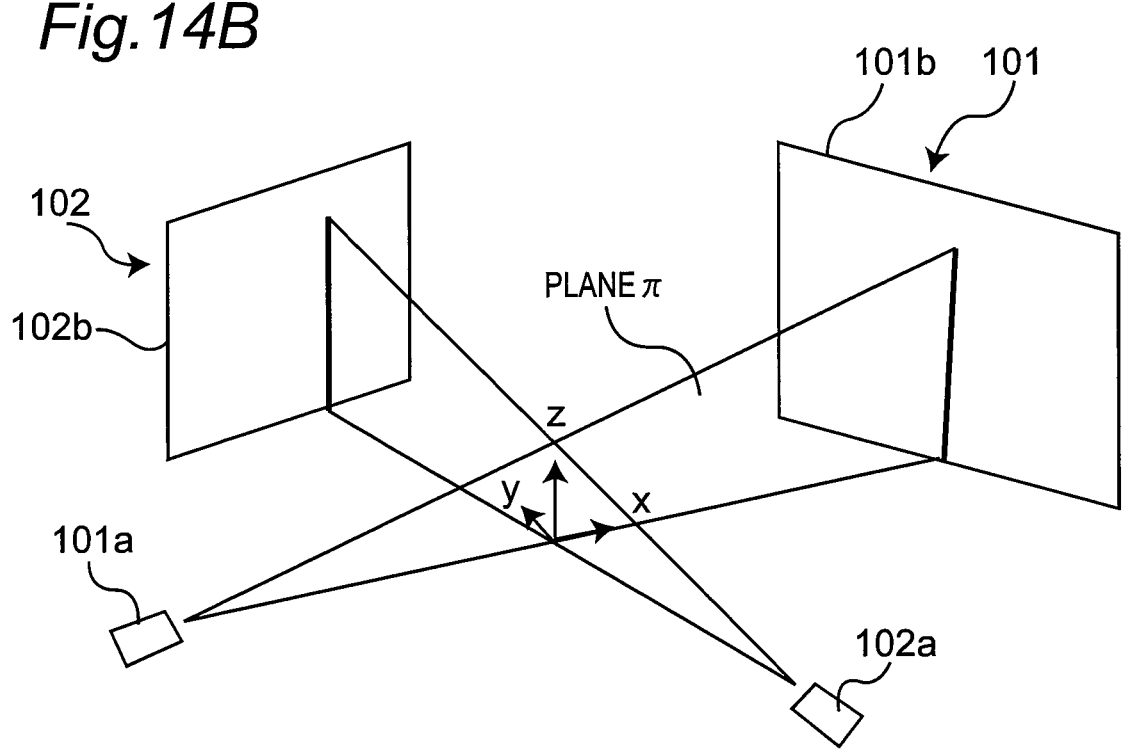
FIG. 14B is a relational view between the catheter and the x-ray fluoroscopic capturing unit at the catheter coordinate calculation time.

A method of calculating the coordinate system by the catheter coordinate determination unit 113 is described with reference to FIGS. 14A and 14B. In this case, a method of calculating the coordinate system using the first x-ray fluoroscopic capturing unit 101 as a start point is described. In the catheter coordinate system, the x-axis is defined as a standard of the direction of the catheter tip-end, and the z-axis is defined as a rotation axis of the catheter tip-end. FIG. 14A shows a positional relation between the catheter 109 and the fluoroscopic capturing units 101 and 102, when the catheter 109 appears to be a straight line in the fluoroscopic image. FIG. 14B shows a catheter coordinate schematic view. As shown in FIG. 14A, it can be understood that when the catheter 109 rotates around the axis, the catheter 109 is observed as a straight line in the fluoroscopic image when the catheter 109 is directed to a detection direction of each of the x-ray detecting units 101b and 102b of the fluoroscopic capturing units 101 and 102, respectively. At this time, to calculate the catheter coordinate system, first, the catheter coordinate determination unit 113 performs three-dimensional shape restoration, by using the catheter tip-end region 109b that is decided as a straight line in the fluoroscopic images obtained by the first x-ray fluoroscopic capturing unit 101 and the second x-ray fluoroscopic capturing unit 102, and the image capture parameters of the x-ray fluoroscopic capturing unit 101. The catheter coordinate determination unit 113 defines the catheter coordinate system, based on a three-dimensional straight line acquired this time. Because the acquired three-dimensional straight line corresponds to the rotation axis of the catheter 109, a three-dimensional shape restoration result of the straight line is assumed as the z-axis, as shown in FIG. 14B. Because the x-axis is the standard of the rotation angle (direction) of the catheter 109, the catheter coordinate determination unit 113 calculates the x-axis on a plane it that connects between the fluoroscopic image and an image-capture position (x-ray generating unit 101a) of the first x-ray fluoroscopic capturing unit 101 and also as a normal line with the z-axis. The catheter coordinate determination unit 113 calculates the y-axis as a normal line with the z-axis and with the x-axis. As described above, the catheter coordinate determination unit 113 can calculate the coordinate system of the catheter 109, from the straight line of the catheter tip-end region 109b and the image capture parameters. The catheter coordinate determination unit 113 outputs the calculated catheter coordinate system to the output unit 107, and also outputs the straight line decision result of the catheter tip-end region 109b to the offset angle calculation unit 114.

(The Output Unit 107)

The output unit 107 receives the catheter tip-end rotation angle from the catheter tip-end rotation angle calculation unit 115, and receives the catheter coordinates from the catheter coordinate determination unit 113. The output unit 107 three-dimensionally presents the catheter tip-end rotation angle, in addition to the display method of the first embodiment, to the catheter operator 110, by using the catheter tip-end rotation angle and the catheter coordinates.

Figure 32A:
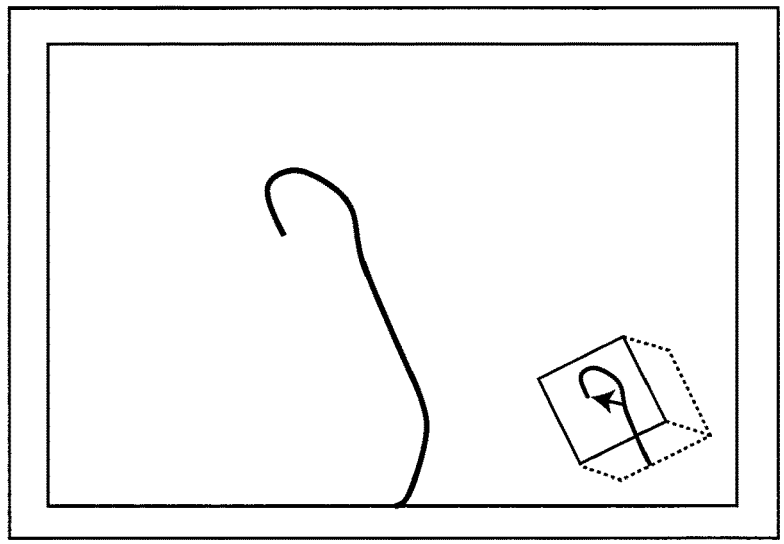
FIG. 32A is an explanatory view of a superposition display of the catheter or the guide wire and a three-dimensional shape model thereof.
Figure 32B:
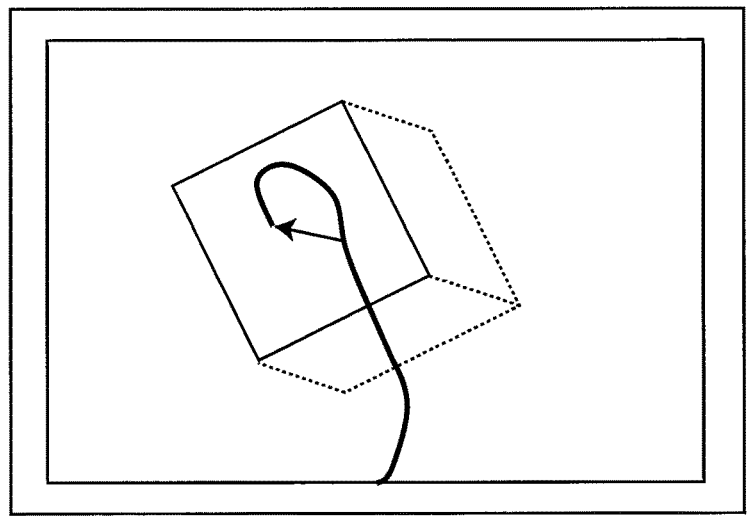
FIG. 32B is an explanatory view of a superposition display of the catheter or the guide wire and a three-dimensional shape model thereof.
Figure 33:
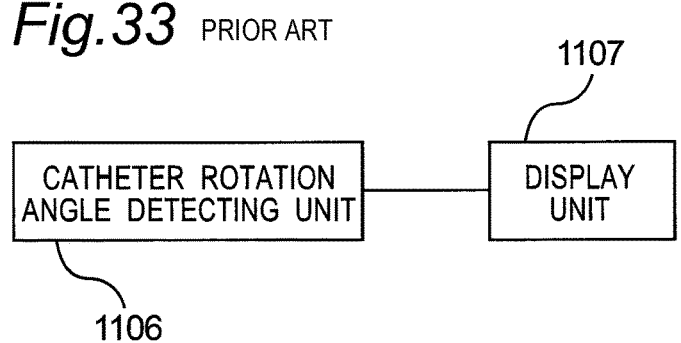
FIG. 33 is a view showing a configuration of a functional block of a conventional catheter action detection device.

The output unit 107 may three-dimensionally display the catheter tip-end rotation angle as shown in FIG. 32A and FIG. 32B, from the catheter tip-end rotation angle received from the catheter tip-end rotation angle calculation unit 115 and a position/orientation conversion matrix to a world coordinate system of the catheter tip-end coordinate system. FIG. 32A shows an example of a three-dimensional display of the catheter (or a guide wire) at a right lower part, and FIG. 32B shows an example of a three-dimensional display superposed with the tip-end of the catheter (or a guide wire). The catheter coordinate determination unit 113 determines a position/orientation conversion matrix to the world coordinate system of the catheter tip-end coordinate system, and outputs the position/orientation conversion matrix to the output unit 107.

The output unit 107 may be configured by a display unit that displays the catheter tip-end rotation angle in superposition with the fluoroscopic image, from the catheter tip-end rotation angle received from the catheter tip-end rotation angle calculation unit 115, the position/orientation conversion matrix to a world coordinate system of a catheter tip-end coordinate system, and the position/orientation of the fluoroscopic capturing unit.

(A Process Flow at a Catheter Coordinate Determination Time)

Figure 15:
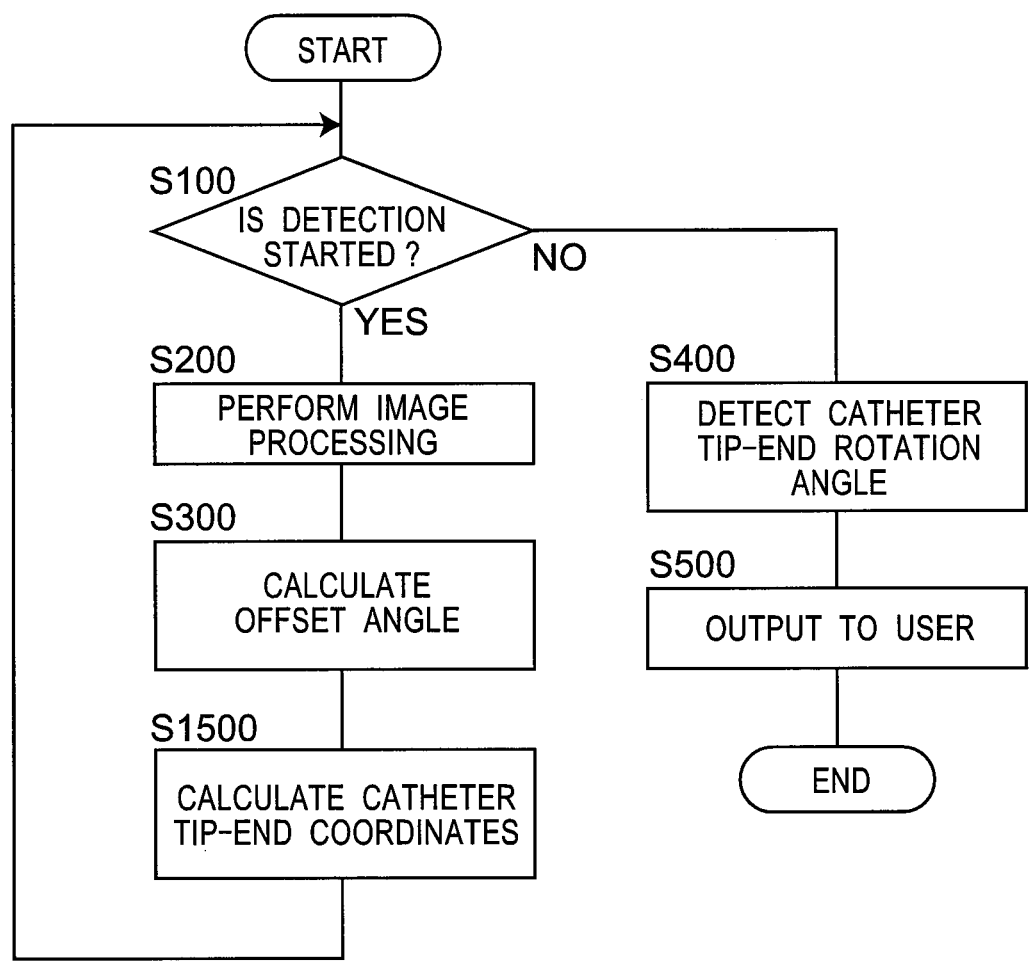
FIG. 15 is a view showing an overall process flow of a catheter tip-end rotation angle detection.
Figure 16:
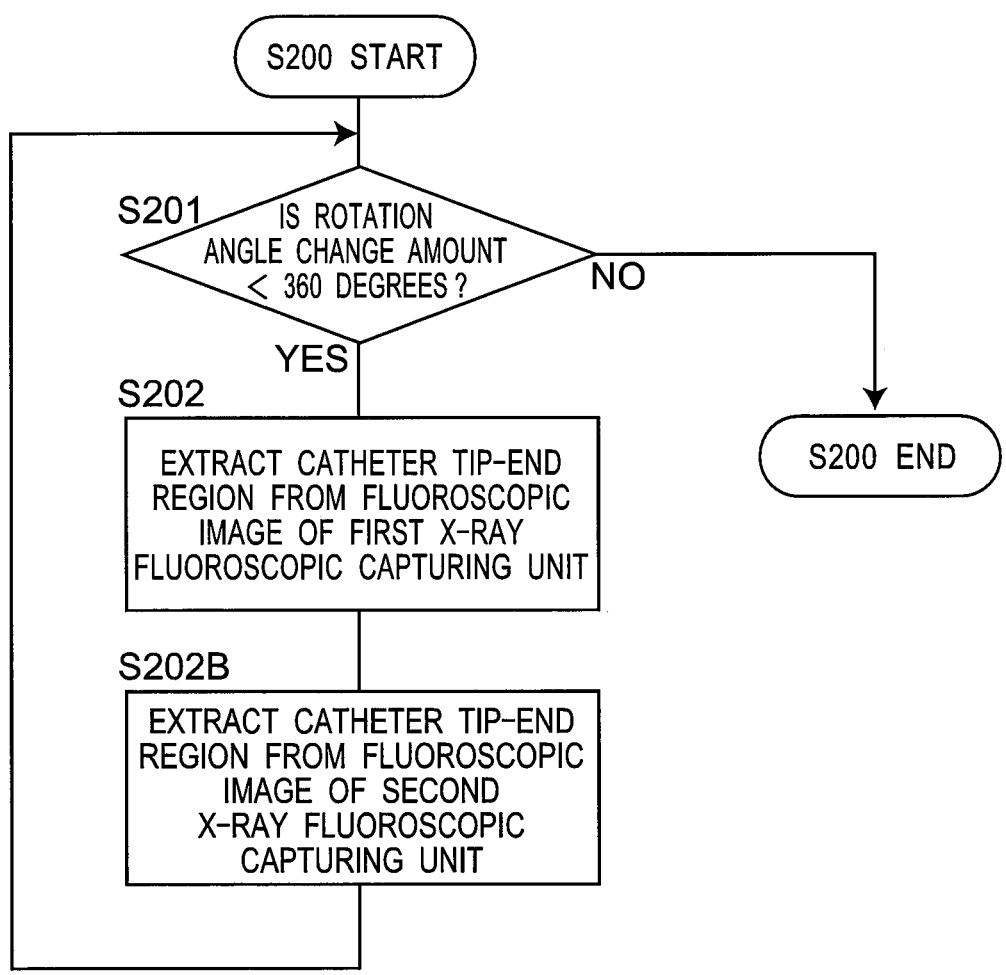
FIG. 16 is a view showing a process flow of the image processing S200.
Figure 17:
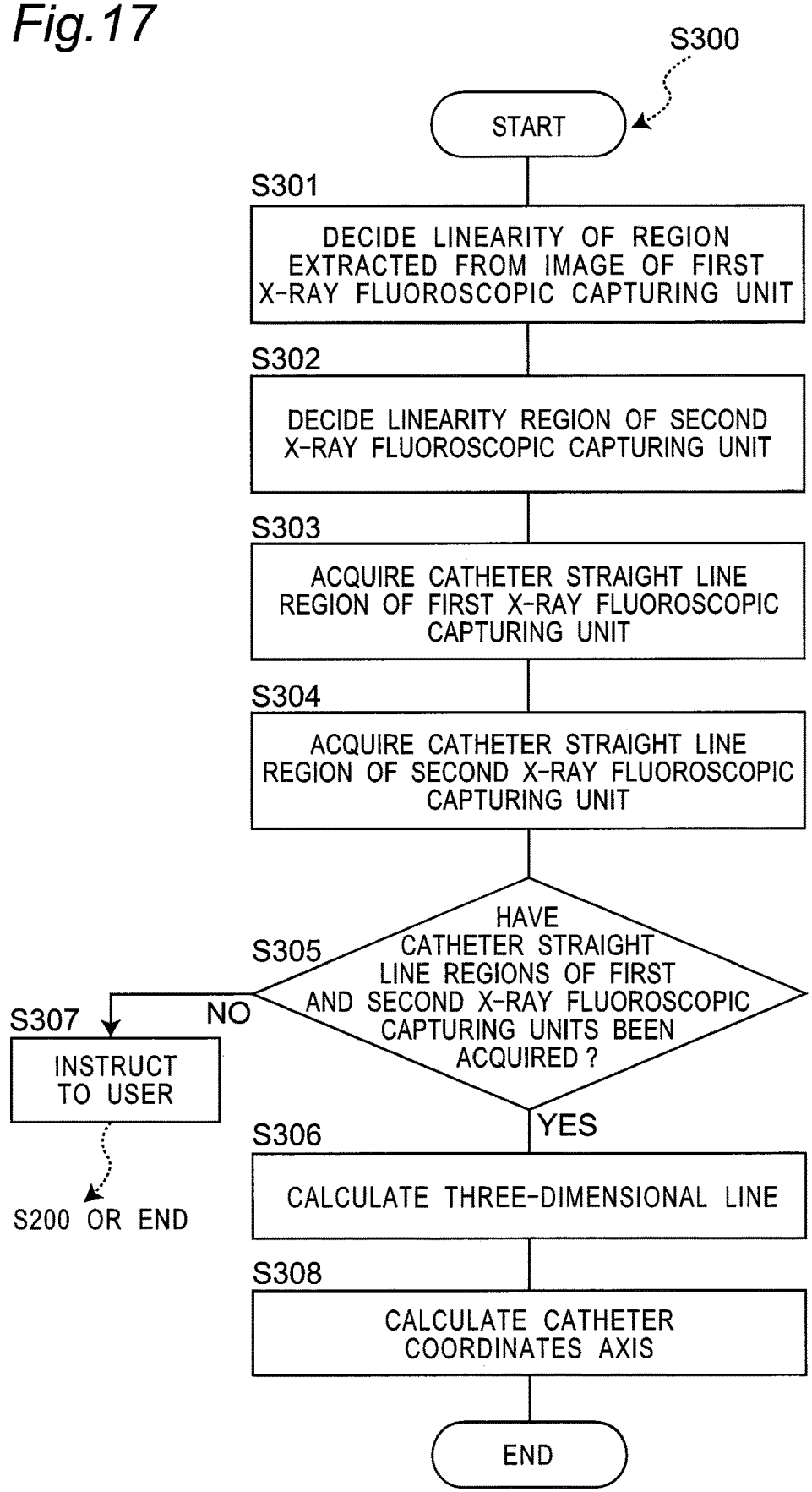
FIG. 17 is a view showing a process flow of a straight line deciding unit and a catheter coordinate deciding unit.

A process flow when the catheter coordinate determination unit 113 makes a catheter coordinate determination is described below with reference to flowcharts in FIG. 15 to FIG. 17. Descriptions of constituent elements that are the same as those of the first embodiment are omitted.

First, an overall process flow of the catheter tip-end rotation angle calculation process when a catheter tip-end coordinate calculation is added is described with reference to FIG. 15.

In step S100, a process that is the same as the process in step S100 of the first embodiment is performed.

In step S200, the image processing unit 103 extracts two catheter tip-end regions 109b from two x-ray fluoroscopic images acquired from two x-ray image capturing devices of the first x-ray fluoroscopic capturing unit 101 and the second x-ray fluoroscopic capturing unit 102. Thereafter, the overall process proceeds to step S300.

Next, in step S300, a process that is the same as that in step S300 of the first embodiment is performed, to each of the extracted two catheter tip-end regions 109b. Thereafter, the overall process proceeds to step S1500.

Next, in step S1500, the catheter coordinate determination unit 113 calculates catheter tip-end coordinates. Details are described later. Thereafter, the overall process returns to step S100.

In steps S400 and S500, processes that are the same as the processes in step S400 and S500 of the first embodiment are performed.

(The Process in Step S200)

The process in step S200 is described in detail with reference to a flowchart in FIG. 16.

First, in step S201, a process that is the same as the process in step S201 of the first embodiment is performed.

In step S202, the first x-ray fluoroscopic capturing unit 101 performs a process that is the same as the process in step S202 of the first embodiment.

Next, in step S202B, the image processing unit 103 extracts the catheter tip-end region 109b from the fluoroscopic image of the second x-ray fluoroscopic capturing unit 102, by a method of pattern matching or the like. Thereafter, the process in step S200 returns to step S201. When a rotation angle is less than 360 degrees, an error output may be performed like in step S204.

(The Process in Step S1500)

A catheter tip-end coordinate calculation process in step S1500 is described in detail with reference to a flowchart in FIG. 17.

In step S301, a process that is the same as the process in step S301 of the first embodiment is performed.

Next, step S302 is a step in which the straight line deciding unit 126 decides linearity of the catheter tip-end region 109b extracted from the fluoroscopic image of the second x-ray fluoroscopic capturing unit 102 extracted in step S203. When the straight line deciding unit 126 decides that the catheter tip-end region 109b is a straight line, the offset angle calculation process proceeds to step S303. When the straight line deciding unit 126 decides that the catheter tip-end region 109b is not a straight line, a subsequent offset angle calculation process is not performed.

Next, in step S303, the catheter coordinate determination unit 113 acquires the catheter tip-end region 109b that is decided as a straight line in step S301.

Next, in step S304, the catheter coordinate determination unit 113 acquires the catheter tip-end region 109b that is decided as a straight line in step S302.

Next, step S305 is a step in which the catheter coordinate determination unit 113 decides whether a straight line has been acquired in step S303, and also decides whether a straight line has been acquired in step S304. When the catheter coordinate determination unit 113 decides that the catheter tip-end regions (straight lines) 109b have been acquired from both the first x-ray fluoroscopic capturing unit 101 and the second x-ray fluoroscopic capturing unit 102, the catheter tip-end coordinate calculation process proceeds to step S306. When the catheter coordinate determination unit 113 decides that the catheter tip-end regions (straight lines) 109b have not been acquired from both the first x-ray fluoroscopic capturing unit 101 and the second x-ray fluoroscopic capturing unit 102 (including a case that the catheter coordinate determination unit 113 decides that the catheter tip-end region (straight line) 109b has been acquired from one of the first x-ray fluoroscopic capturing unit 101 and the second x-ray fluoroscopic capturing unit 102), the catheter tip-end coordinate calculation process proceeds to step S307.

In step S307, the output unit 107 displays to the catheter operator 110 that the catheter tip-end regions (straight lines) 109b have not been acquired from both the first x-ray fluoroscopic capturing unit 101 and the second x-ray fluoroscopic capturing unit 102. Thereafter, the process proceeds to step S200, or the catheter tip-end coordinate calculation process ends.

Figure 18A:
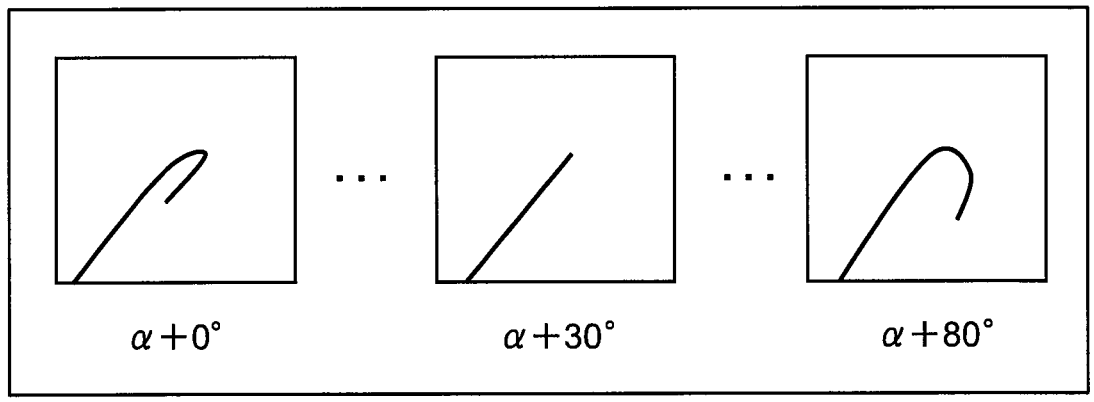
FIG. 18A is an explanatory view of a method of restoring a catheter rotation axis, and shows a catheter tip-end image of a first x-ray fluoroscopic capturing unit.
Figure 18B:
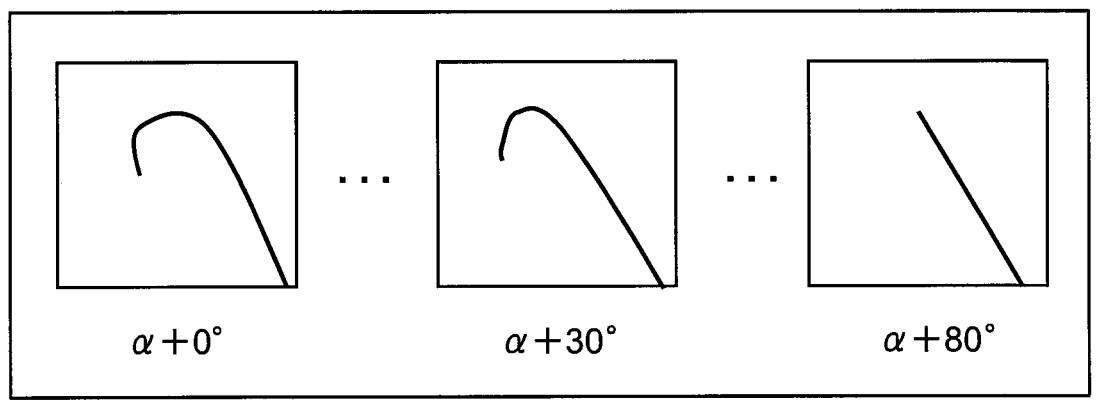
FIG. 18B is an explanatory view of the method of restoring a catheter rotation axis, and shows a catheter tip-end image of a second x-ray fluoroscopic capturing unit.
Figure 19:
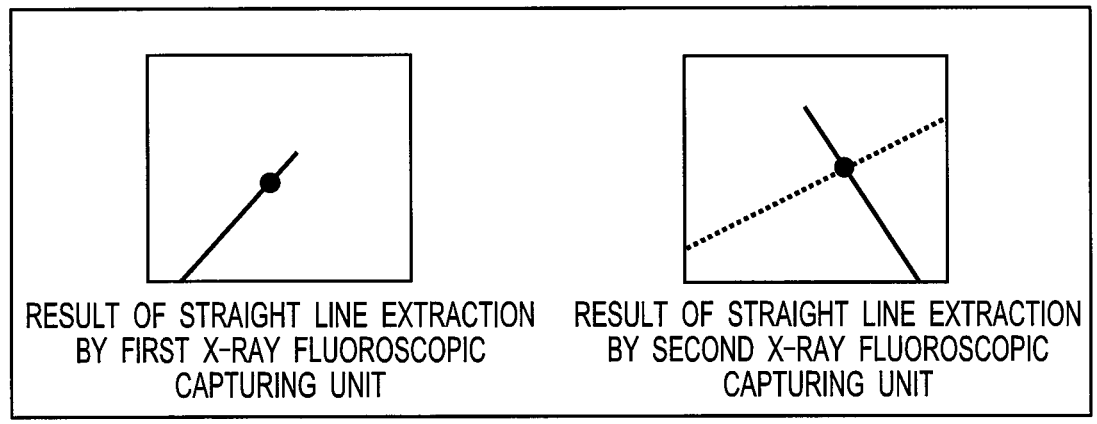
FIG. 19 is an explanatory view of the method of restoring a catheter rotation axis, and shows a correspondence relation decision from a straight line extraction result.

Step S306 is a step in which the catheter coordinate determination unit 113 performs three-dimensional shape restoration by using straight line regions acquired in step S303 and step S304, respectively, and the catheter coordinate determination unit 113 calculates a three-dimensional straight line. After step S306, the process proceeds to step S308. A method of calculating a three-dimensional straight line is described with reference to FIG. 18A to FIG. 19. FIG. 18A and FIG. 18B show respectively catheter tip-end images of the first x-ray fluoroscopic capturing unit 101 and the second x-ray fluoroscopic capturing unit 102 when the catheter 109 is rotated by one turn. In the drawings, α represents an operator's hand-side rotation angle. As shown in FIG. 18A and FIG. 18B, because the first x-ray fluoroscopic capturing unit 101 and the second x-ray fluoroscopic capturing unit 102 are set to different angles, normally, the catheter tip-ends do not simultaneously appear to be straight lines. Normally, in the three dimensional restoration, the coordinate determination unit 113 restores a three-dimensional shape from two or more images captured at the same time. However, in the second embodiment, the catheter coordinate determination unit 113 extracts a correspondence relation from images at different times in which the catheter 109 is observed as straight line, and calculates a three-dimensional straight line, as shown in FIG. 19.

First, a method of extracting a correspondence relation from images of different times by the catheter coordinate determination unit 113 is described. In this case, an example of a case that the catheter coordinate determination unit 113 extracts the correspondence by using an epipolar line is described.

Calculation of an epipolar line based on the image of the first x-ray fluoroscopic capturing unit 101 is described. For details of the method of extracting the correspondence relation, it is suggested that Non-Patent Literature ("Computervision—geometry of eyesight—" by Atsushi Sato, Corona Publishing Co., Ltd. An outline is described below. The following calculations are all performed by the catheter coordinate determination unit 113.

First, to extract a corresponding point between a plurality of images, a fundamental matrix F is calculated that indicates a geometric relation between a plurality of images from image capture parameters (projection matrices of the first x-ray fluoroscopic capturing unit 101 and the second x-ray fluoroscopic capturing unit 102) by using Equation (7).

$$F=[P'C]_x P'P^- \qquad (7)$$

Here, P represents a projection matrix of the first x-ray fluoroscopic capturing unit 101, P' represents a projection matrix of the second x-ray fluoroscopic capturing unit 102, and C represents an image-capturing viewpoint (zero space of P) of the first x-ray fluoroscopic capturing unit 101).

By using Equation (8), an epipolar line (see a dotted line in FIG. 19) that corresponds to a point on a straight line extracted from the fluoroscopic image of the first x-ray fluoroscopic capturing unit 101 is calculated.

$$l'=Fm \qquad (8)$$

Here, F represents a fundamental matrix, l' represents an epipolar line of the second x-ray fluoroscopic capturing unit 102 that corresponds to a point m in the fluoroscopic image of the first x-ray fluoroscopic capturing unit 101, and m represents the point in the fluoroscopic image of the first x-ray fluoroscopic capturing unit 101.

In this case, the epipolar line indicates an existence range in the second x-ray fluoroscopic capturing unit 102. Therefore, by calculating an intersection between the epipolar line and the extracted straight line, a corresponding point between the first x-ray fluoroscopic capturing unit 101 and the second x-ray fluoroscopic capturing unit 102 can be calculated. Between the image capture parameters (projection matrices of the first x-ray fluoroscopic capturing unit 101 and the second x-ray fluoroscopic capturing unit 102) and the corresponding point of the first x-ray fluoroscopic capturing unit 101 and the second x-ray fluoroscopic capturing unit 102, a projection formula as expressed by Equation (9) is established. Therefore, when the projection formula of the first x-ray fluoroscopic capturing unit 101 and the second x-ray fluoroscopic capturing unit 102 is summarized for three-dimensional point X, the projection formula can be transformed as Equation (13).

$$\lambda \begin{bmatrix} u \\ v \\ 1 \end{bmatrix} = \begin{bmatrix} p_{11} & p_{12} & p_{13} & p_{14} \\ p_{21} & p_{22} & p_{23} & p_{24} \\ p_{31} & p_{32} & p_{33} & p_{34} \end{bmatrix} \begin{bmatrix} X \\ Y \\ Z \\ 1 \end{bmatrix} \quad (9)$$

The projection matrix P of the first x-ray fluoroscopic capturing unit 101 is as follows.

$$P = \begin{bmatrix} p_{11} & p_{12} & p_{13} & p_{14} \\ p_{21} & p_{22} & p_{23} & p_{24} \\ p_{31} & p_{32} & p_{33} & p_{34} \end{bmatrix} \quad (10)$$

Here, m represents the point in the fluoroscopic image of the first x-ray fluoroscopic capturing unit 101.

$$m = [u, v, 1]^T \quad (11)$$

The point X in the three-dimensional space is as follows.

$$X = [X, Y, Z, 1]^T \quad (12)$$

Here, $\lambda$ is a real number that indicates constant multiplication uncertainty.

$$\begin{bmatrix} p_{31}u - p_{11} & p_{32}u - p_{12} & p_{33}u - p_{13} \\ p_{31}v - p_{21} & p_{32}v - p_{22} & p_{33}v - p_{23} \\ p'_{31}u' - p'_{11} & p'_{32}u' - p'_{12} & p'_{33}u' - p'_{13} \\ p'_{31}v' - p'_{21} & p'_{32}v' - p'_{22} & p'_{33}v' - p'_{23} \end{bmatrix} \begin{bmatrix} X \\ Y \\ Z \end{bmatrix} = \begin{bmatrix} p_{14} - p_{34}u \\ p_{24} - p_{34}v \\ p'_{14} - p'_{34}u' \\ p'_{24} - p'_{34}v' \end{bmatrix} \quad (13)$$

This is expressed as follows.

$$MX = b \quad (14)$$

Therefore, by using Equation (15) that is obtained by transforming Equation (13), a three-dimensional point can be restored from the image capture parameters (projection matrices of the first x-ray fluoroscopic capturing unit 101 and the second x-ray fluoroscopic capturing unit 102) and the corresponding point between the first x-ray fluoroscopic capturing unit 101 and the second x-ray fluoroscopic capturing unit 102.

$$X = M^+ b \quad (15)$$

$M^+$ is a generalized inverse matrix of M.

By performing this process on a plurality of points on the straight line extracted from the fluoroscopic image of the first x-ray fluoroscopic capturing unit 101, a three-dimensional straight line can be calculated.

Next, step S308 is a step in which the catheter coordinate is calculated from the three-dimensional straight line calculated in step S306 and from the image capture parameters of the first x-ray fluoroscopic capturing unit 101 and the second x-ray fluoroscopic capturing unit 102. A method of determining the coordinates is as described in "(The catheter coordinate determination unit 113)". Thereafter, the catheter tip-end coordinate calculation process ends.

In the second embodiment, the catheter coordinate determination unit 113 performs three-dimensional reconfiguration of the three-dimensional straight line from the images of the first x-ray fluoroscopic capturing unit 101 and the second x-ray fluoroscopic capturing unit 102. Therefore, the first x-ray fluoroscopic capturing unit 101 and the second x-ray fluoroscopic capturing unit 102 must not be set at the same position.

The three-dimensional reconfiguration can be stably calculated when a distance (base line length) between the first x-ray fluoroscopic capturing unit 101 and the second x-ray fluoroscopic capturing unit 102 is longer. Therefore, a distance between the first x-ray fluoroscopic capturing unit 101 and the second x-ray fluoroscopic capturing unit 102 is equal to or larger than 10 cm, for example.

(An Effect of the Second Embodiment)

According to the catheter tip-end rotation angle detection apparatus 100B in the second embodiment, the catheter operator 110 can detect a catheter tip-end rotation angle (direction), by displaying the detected rotation angle in a display or the like. Therefore, the catheter operator 110 can understand correspondence between the manipulation of the catheter operator 110 and a spatial rotational movement direction of the catheter 109 at current time (detection time) Therefore, the user can smoothly perform a catheter manipulation and surgery.

(Third Embodiment)

the first embodiment, the catheter tip-end rotation angle detection is described for the case that the catheter operator 110 performs a detection start input to the user input unit 108 and intentionally causes the catheter 110 to be rotated by one turn. However, during a catheter manipulation, the catheter operator 110 frequently manipulates the catheter 109 to rotate. Therefore, there occurs a situation that the catheter 109 appears to be a straight line in the fluoroscopic image. Therefore, in a third embodiment, there is described an operation of a catheter tip-end rotation angle detection apparatus 100C that can detect a catheter tip-end rotation angle when the catheter operator 110 does not intentionally perform a detection start input.

Figure 20:
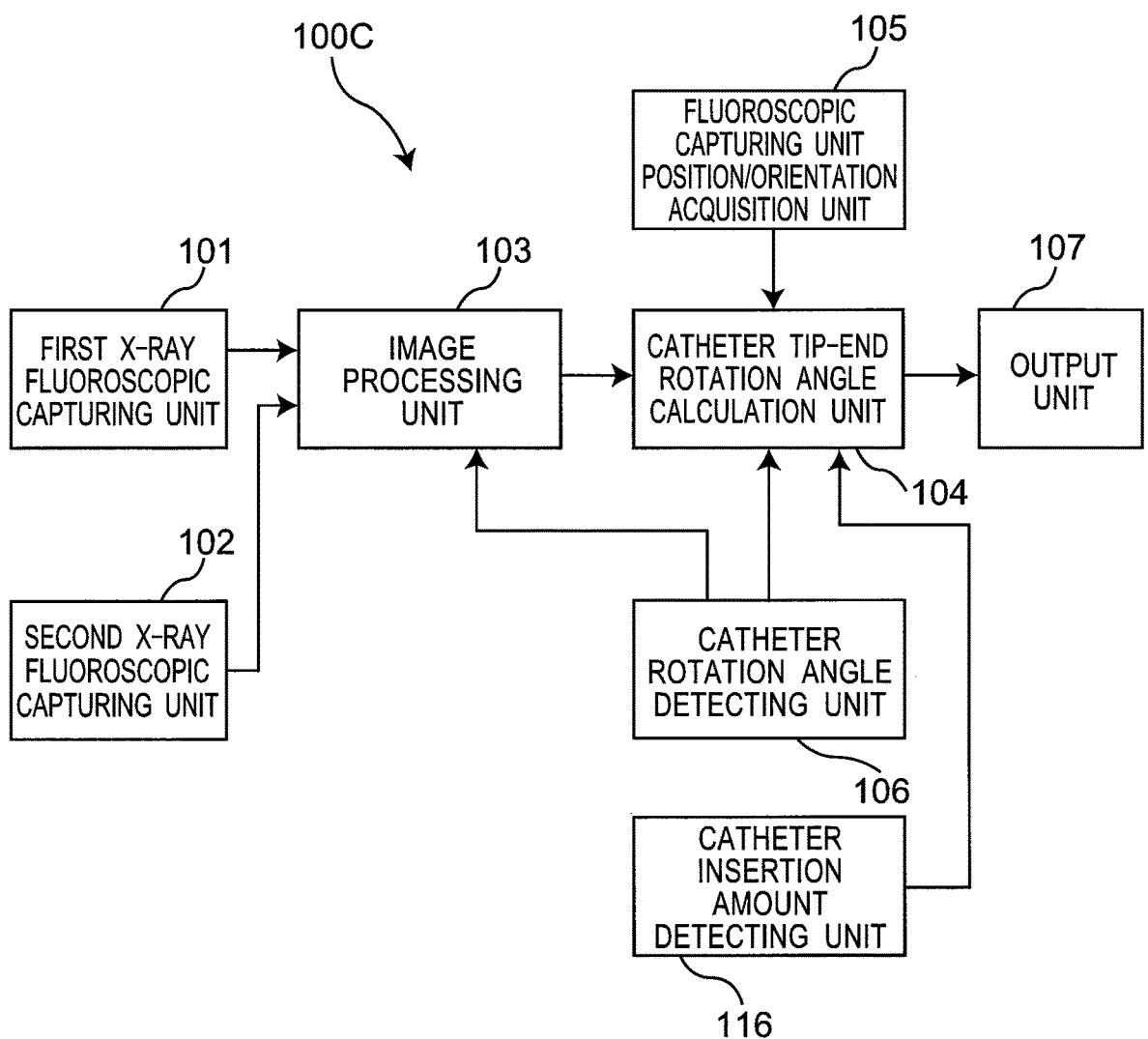
FIG. 20 is a configuration view of functional blocks of a catheter tip-end rotation angle detection apparatus according to a third embodiment of the present invention.

FIG. 20 shows a block diagram of the catheter tip-end rotation angle detection apparatus 100C according to the third embodiment of the present invention. Descriptions of constituent elements that are the same as those of the first embodiment are omitted. Hereinafter, operations of units relating to the third embodiment of the present invention are described.

The catheter tip-end rotation angle detection apparatus 100C according to the third embodiment includes a catheter insertion amount detecting unit 116 and a detection condition deciding unit 117, in addition to the constituent elements of the first embodiment. The catheter insertion amount detecting unit 116 calculates an offset angle from an image in which an insertion amount does not change (catheter coordinates do not change).

The catheter insertion amount detecting unit 116 detects a catheter insertion amount of the catheter 109 into a body lumen such as a blood vessel.

The detection condition deciding unit 117 decides whether to perform a catheter detection process, based on the image capture parameters of the fluoroscopic capturing unit position/orientation acquisition unit 105 and a detection value (insertion amount) of the catheter insertion amount detecting unit 116.

Each block is described in detail below.

(The Catheter Insertion Amount Detecting Unit 116)

Figure 34A:
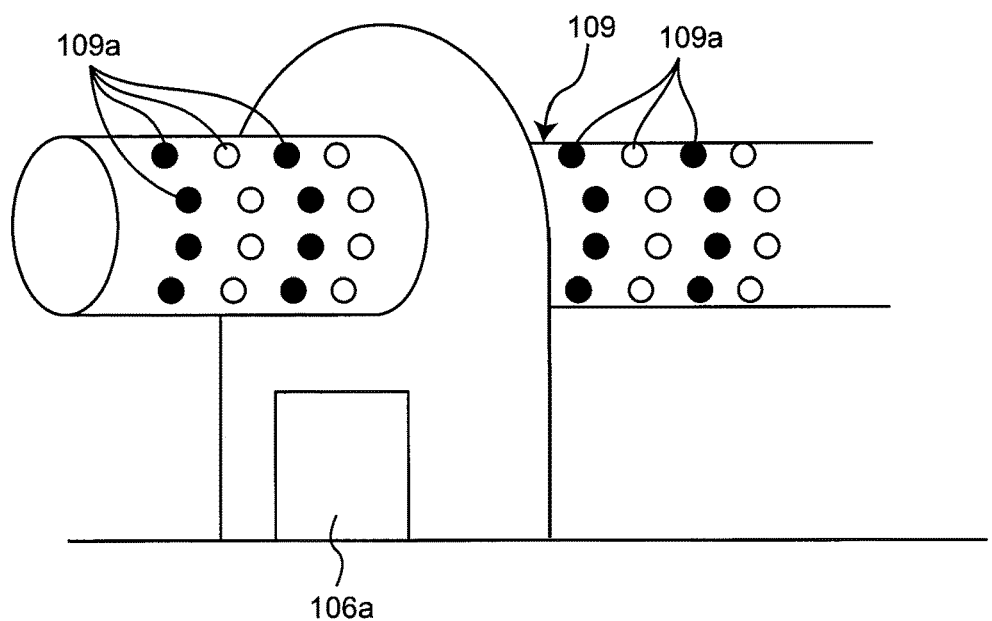
FIG. 34A is an explanatory view showing an example of a catheter insertion amount detecting unit.
Figure 34B:
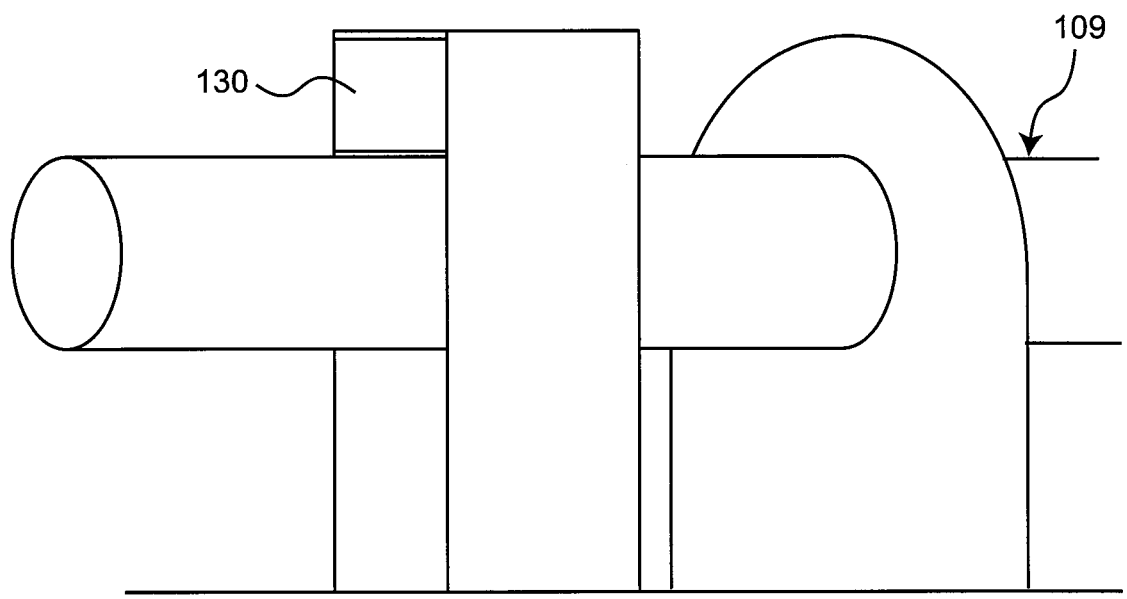
FIG. 34B is an explanatory view showing another example of a catheter insertion amount detecting unit.

The catheter insertion amount detecting unit 116 is a device that detects an insertion amount of the catheter in the catheter operator's hand. The catheter insertion amount detecting unit 116 detects an insertion amount, and outputs the detected insertion amount to the catheter tip-end rotation angle calculation unit 104. The catheter insertion amount detecting unit 116 continues detecting an insertion amount from an inspection start to an inspection end. The catheter insertion amount detecting unit 116 may apply continuous patterns 109a to around the axis of the catheter 109, capture the continuous patterns 109a with a camera 106a, and measure the insertion amount, as shown in FIG. 34A, for example. As a separate example of the catheter insertion amount detecting unit 116, an insertion amount maybe measured, by using a sensor 130 that directly measures an insertion amount by contacting the sensor 130 to the catheter 109, as shown in FIG. 34B.

(The Detection Condition Deciding Unit 117)

Figure 21:
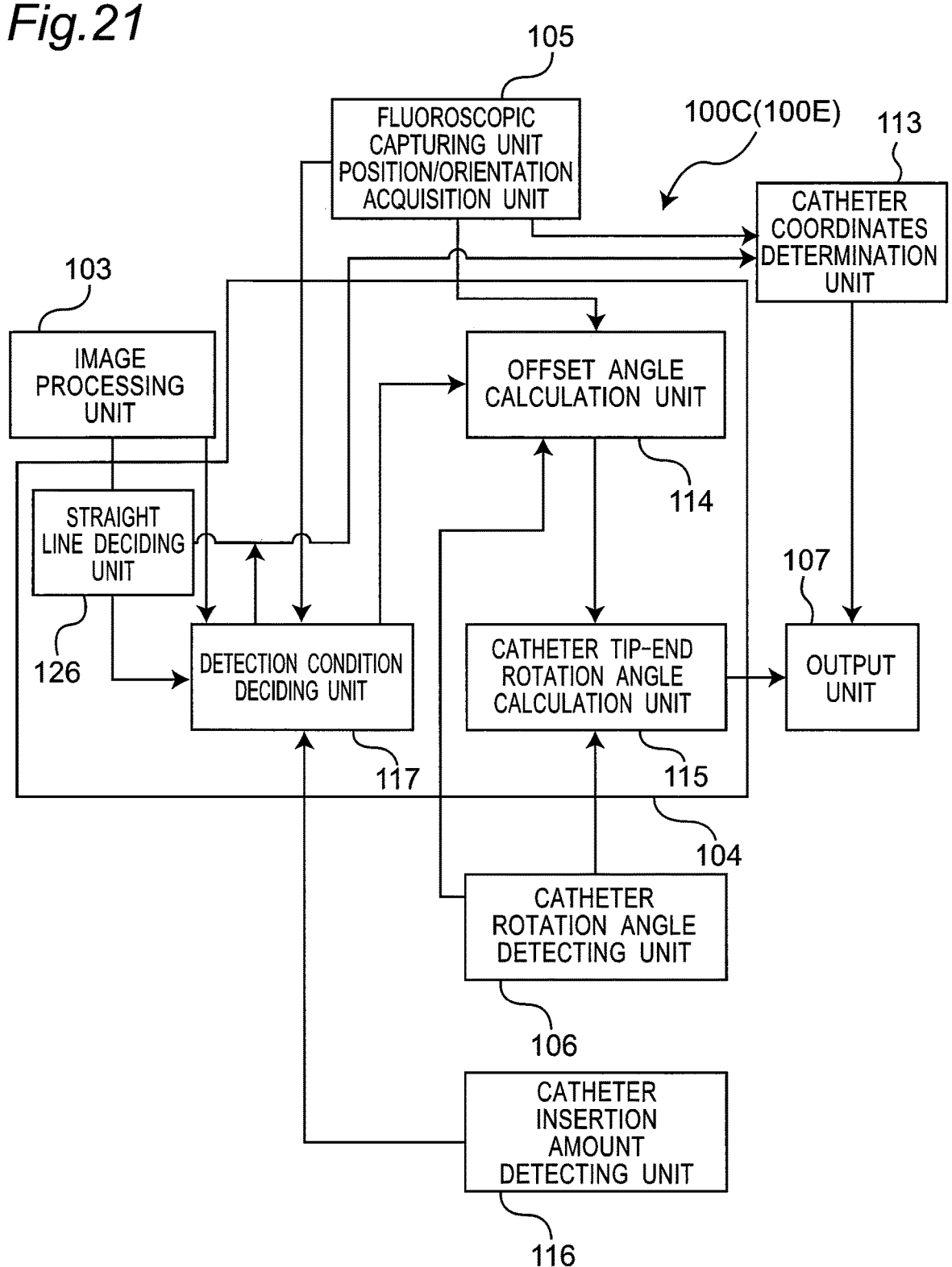
FIG. 21 is a functional block diagram of a catheter tip-end rotation angle calculation unit.

A block of the detection condition deciding unit 117 is described with reference to FIG. 21. FIG. 21 is a functional block diagram of the catheter tip-end rotation angle calculation unit 104 with the block of the detection condition deciding unit 117 added thereto.

The detection condition deciding unit 117 decides whether to perform the catheter tip-end rotation angle calculation process, based on a catheter tip-end region extraction result, a catheter insertion amount, and image capture parameters. The detection condition deciding unit 117 acquires the catheter tip-end region extraction result from the image processing unit 103, acquires the catheter insertion amount from the catheter insertion amount detecting unit 116, and acquires the image capture parameters from the fluoroscopic capturing unit position/orientation acquisition unit 105. Then, the detection condition deciding unit 117 decides whether to perform the catheter tip-end rotation angle calculation process, based on the acquired information. As a result of the decision made by the detection condition deciding unit 117, when the detection condition deciding unit 117 decides to perform the catheter tip-end rotation angle calculation process, the detection condition deciding unit 117 outputs a catheter tip-end region extraction result to the catheter coordinate determination unit 113. When the detection condition deciding unit 117 decides not to perform the catheter tip-end rotation angle calculation process, the detection condition deciding unit 117 does not output a catheter tip-end region extraction result to the catheter coordinate determination unit 113.

(A Process Flow of the Catheter Tip-End Rotation Angle Detection Apparatus (Third Embodiment))

Figure 23:
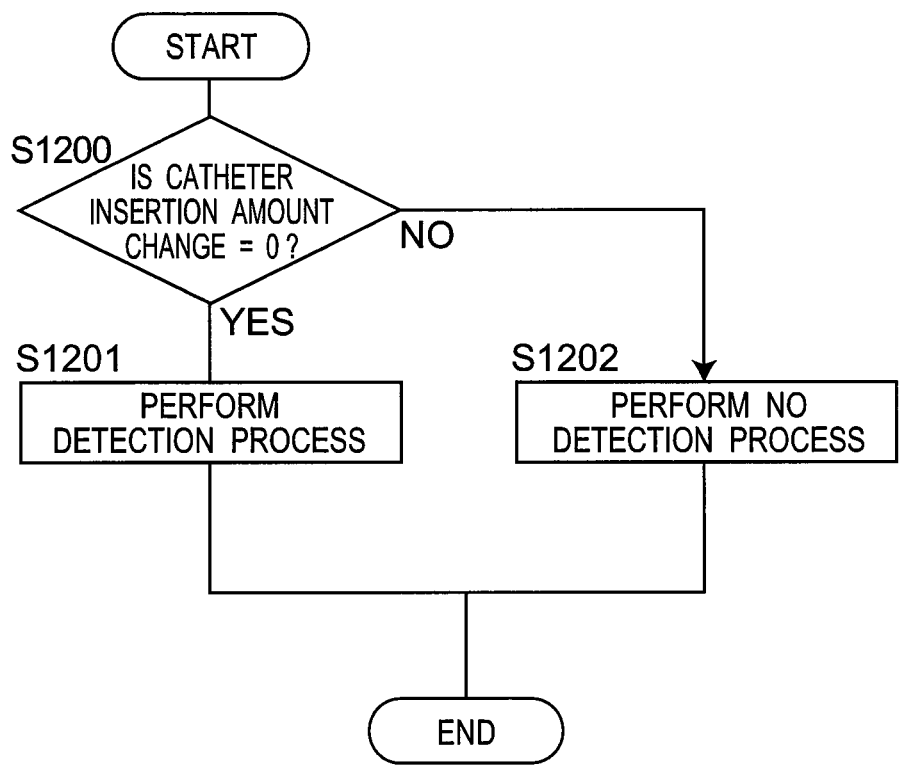
FIG. 23 is a process flowchart of a detection condition deciding unit.

A detection condition decision process flow is described below with reference to a flowchart in FIG. 23.

Step S1200 is a process in which the detection condition deciding unit 117 decides whether there is a change by a predetermined range (error range) or greater in the catheter insertion amount detected by the catheter insertion amount detecting unit 116. When the detection condition deciding unit 117 decides that there is no change in a catheter insertion amount based on a detection value from the catheter insertion amount detecting unit 116, the detection condition decision process proceeds to step S1201. When the detection condition deciding unit 117 decides that there is a change in a catheter insertion amount, the detection condition decision process proceeds to step S1202. In step S1200, even when there is no input by catheter operator 110, the catheter insertion amount detecting unit 116 continues acquiring a catheter insertion amount, and the detection condition deciding unit 117 decides whether there is a change in a catheter insertion amount.

For the decision of a change in the catheter insertion amount, the detection condition deciding unit 117 measures a change in the catheter insertion amount of a time $\Delta t$, based on a detection value from the catheter insertion amount detecting unit 116. The time $\Delta t$ means a time from time t1 when the straight line deciding unit 126 decides a straight line based on an x-ray fluoroscopic image of the first x-ray fluoroscopic capturing unit 101 via the image processing unit 103 to time t2 when the straight line deciding unit 126 next decides a straight line based on an x-ray fluoroscopic image of the second x-ray fluoroscopic capturing unit 102 via the image processing unit 103. When a change amount of the catheter insertion amount during the time $\Delta t$ is less than a change amount $\Delta x$ specified in advance by the catheter operator 110, the detection condition deciding unit 117 decides that there is no change in the catheter insertion amount. When a change amount of the catheter insertion amount during the time $\Delta t$ is equal to or greater than the change amount $\Delta x$, the detection condition deciding unit 117 decides that there is a change in the catheter insertion amount. A length of the catheter insertion change amount $\Delta x$ is a distance by which the rotation axis of the catheter 109 is considered to change.

The catheter insertion change amount $\Delta x$ may be set to 1 cm, 3 cm, 5 cm, 10 cm, for example, that the catheter operator 110 can select. The catheter operator 110 can select the catheter insertion change amount $\Delta x$ based on complexity of the blood vessel of the target portion of catheter surgery, for example (a curvature radius of a brain blood vessel is 1 cm, and a curvature radius of a leg blood vessel is 10 cm, for example). When the blood vessel is near a straight line (when a curvature radius is large), there is small influence even when the catheter insertion change amount $\Delta x$ change to some extent. Therefore, the detection condition deciding unit 117 decides that "there is no change". On the other hand, in the case of a blood vessel that is finely bent such as a brain blood vessel (blood vessel of which a curvature radius is small), the detection condition deciding unit 117 decides that "there is a change", even when the catheter insertion change amount $\Delta x$ is a small change amount.

Figure 22:
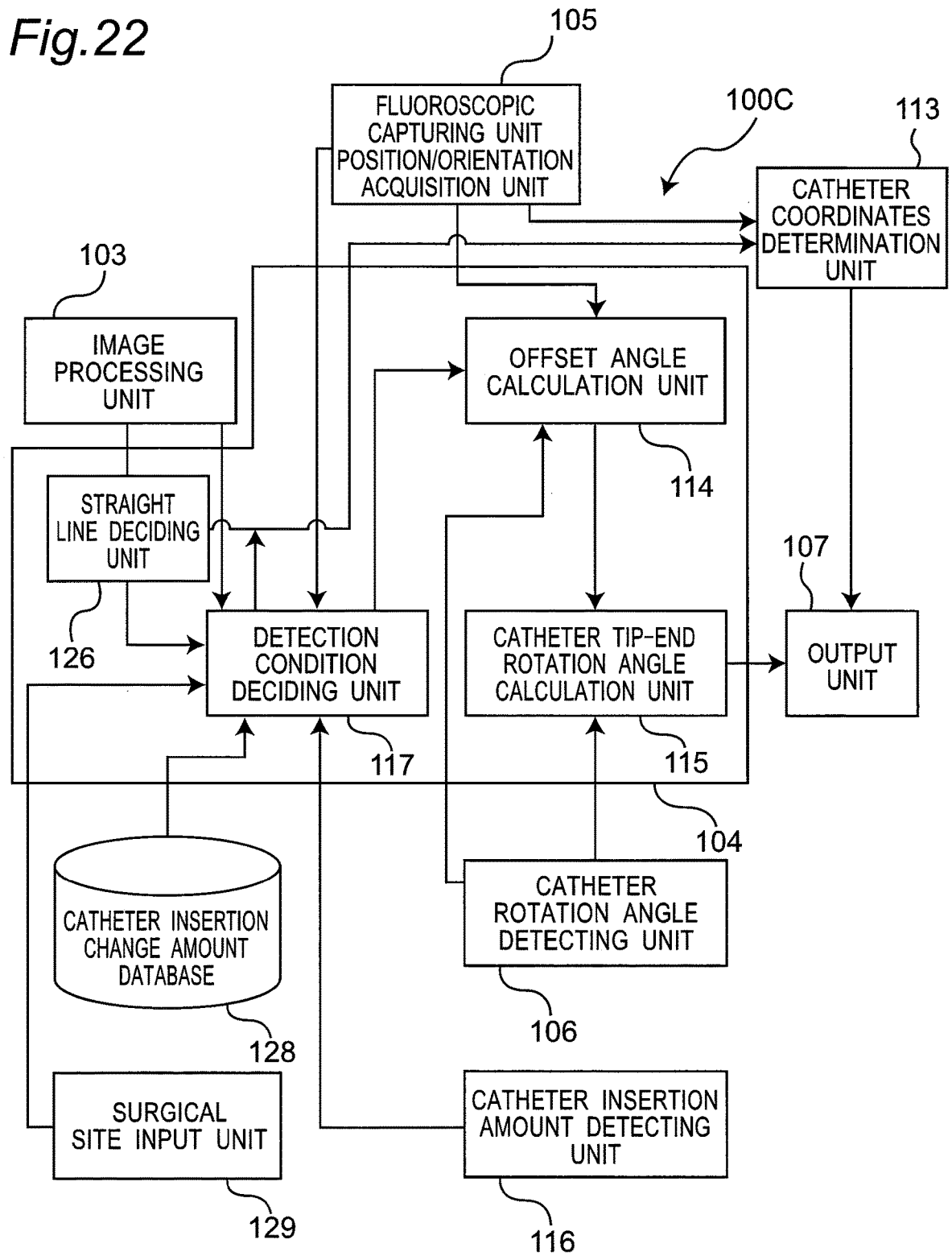
FIG. 22 is a detailed functional block diagram of the catheter tip-end rotation angle calculation unit.

As shown in FIG. 22, the catheter tip-end rotation angle detection apparatus may further include a catheter insertion change amount database 128 that is connected to the detection condition deciding unit 117 and that stores a catheter insertion change amount of each site, and a surgical site input unit 129 that is connected to the detection condition deciding unit 117 and is used when the catheter operator 110 inputs a surgical site. In this case, a catheter insertion change amount of each site may be stored in advance in the catheter insertion change amount database 128. According to the input to the surgical site input unit 129, the detection condition deciding unit 117 may read the catheter insertion change amount of each target surgical site from the catheter insertion change amount database 128 and change the catheter insertion change amount for each target surgical site.

A straight line decision order of the first x-ray fluoroscopic capturing unit 101 and the second x-ray fluoroscopic capturing unit 102 may be opposite.

In step S1201, the detection condition deciding unit 117 decides to perform the catheter tip-end rotation angle calculation process. The detection condition deciding unit 117 outputs the catheter tip-end region extraction result received from the image processing unit 103, to the catheter coordinate determination unit 113.

In step S1202, the detection condition deciding unit 117 decides not to perform the catheter tip-end rotation angle calculation process. The detection condition deciding unit 117 does not output the catheter tip-end region extraction result received from the image processing unit 103, to the catheter coordinate determination unit 113.

(An Effect of the Third Embodiment)

According to the third embodiment, the catheter operator 110 can accurately detect a catheter tip-end rotation angle, by only manipulating the catheter 109, without performing a detection start input to the user input unit 108. Therefore, the user can smoothly perform a catheter manipulation and surgery, by not performing a detection start input to the user input unit 108.

(Fourth Embodiment)

In the first to third embodiments, methods of detecting the catheter tip-end rotation angle are mainly described. However, in the catheter contrast radiography, a guide wire 112 for guiding the catheter 109 to a proper portion is used in a body lumen such as a blood vessel as well as using the catheter 109.

Figure 24A:
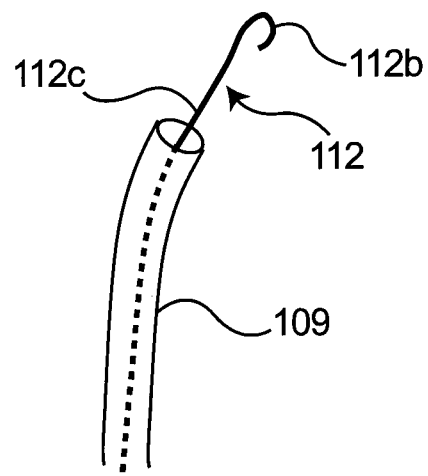
FIG. 24A is a schematic view of a catheter and a guide wire.
Figure 24B:
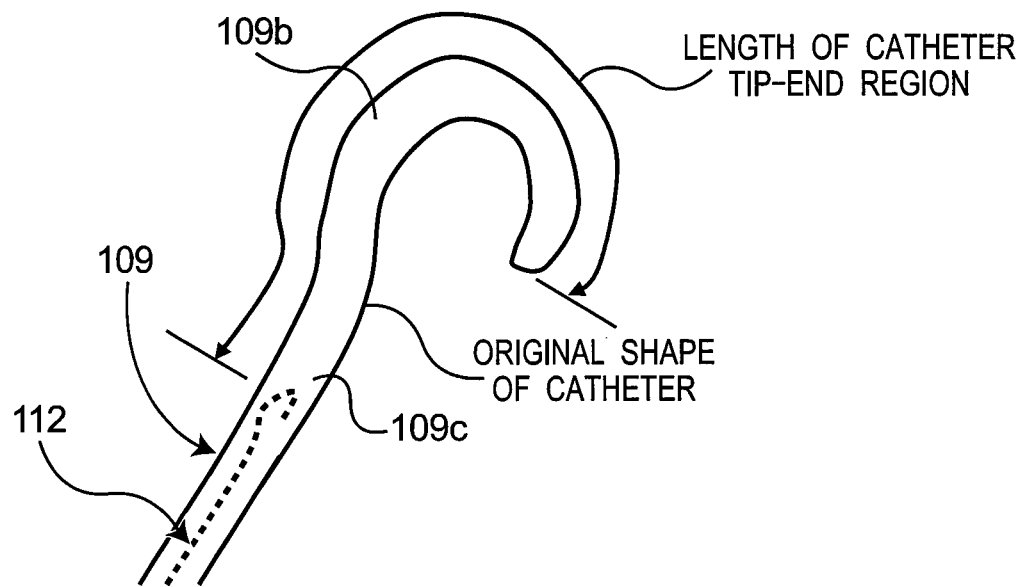
FIG. 24B is a schematic view of the catheter and the guide wire when a catheter insertion amount is equal to or greater than a total of a guide wire insertion amount and a catheter tip-end region length.

FIG. 24A shows a schematic view of the catheter 109 and the guide wire 112. As shown in FIG. 24A, the guide wire 112 is a needle-shaped tool that passes through a center part of the catheter 109. The guide wire 112 has a bent part 112b at a tip-end that is bent in a hook shape relative to a straight-line base 112c, as a guide-wire tip-end region, and the guide wire 112 is inserted into a body lumen 150. First, a method of using the catheter 109 and the guide wire 112 is briefly described. When the catheter 109 and the guide wire 112 are inserted into a blood vessel so that a guide wire insertion amount is larger than a catheter insertion amount, a mode as shown in FIG. 24A and FIG. 24B is acquired. A tip-end of the guide wire 112 protruded from the tip-end of the catheter 109 is made to lead the tip-end of the catheter 109 to blood vessel branch portion, so that the catheter 109 can be made to reach a target blood vessel. At the time of injecting a contrast medium, as shown in FIG. 24B, the guide wire 112 is pulled out of the catheter 109, and the tip-end of the guide wire 112 is inserted into and positioned at the tip-end of the catheter 109 or at a base side from the tip-end. Then, the direction of the catheter tip-end is coincided with a branch direction of the target blood vessel, and thereafter, the contrast medium is injected from the catheter 109. For detecting a catheter tip-end rotation angle, because the catheter 109 and the guide wire 112 can be independently rotated, it is necessary to independently detect a guide-wire tip-end rotation angle as well as to detect a catheter tip-end rotation angle.

Figure 24C:
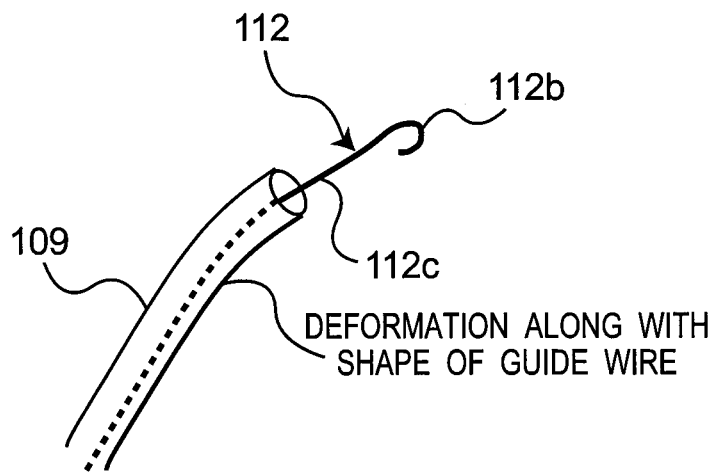
FIG. 24C is a schematic view of the catheter and the guide wire when the catheter insertion amount is smaller than the total of the guide wire insertion amount and the catheter tip-end region length.

It is assumed that the catheter insertion amount and the guide wire insertion amount are lengths based on insertion points of the catheter 109 and the guide wire 112 into the patient 110, and that a length of the portion (section from a catheter tip-end to the base 109c where the catheter body becomes a straight line) 109b of the catheter tip-end (region) is a catheter tip-end region length (see FIG. 24B). At this time, as shown in FIG. 24B, when the catheter insertion amount is equal to or larger than a distance of a sum of the guide wire insertion amount and the catheter tip-end region length, the catheter 109 is image-captured in an original shape, and the guide wire 112 is inside the catheter. Therefore, the guide wire 112 is not confirmed in the fluoroscopic image. On other hand, as shown in FIG. 24C, when the catheter insertion amount is smaller than a distance of a sum of the guide wire insertion amount and the catheter tip-end region length, both the catheter 109 and the guide wire 112 can be detected in the fluoroscopic image. However, because a shape of the catheter 109 is deformed to match the shape of the guide wire 112, a straight line decision result that uses the fluoroscopic image is not reliable. Therefore, it is necessary to change a detection target of a tip-end rotation angle depending on the catheter insertion amount and the guide wire insertion amount, as shown in FIG. 24B and FIG. 24C. In a fourth embodiment, there is described an operation of a catheter tip-end rotation angle detection apparatus 100D that can detect a catheter tip-end rotation angle (direction) and a guide wire tip-end rotation angle (direction) at the time of manipulating the catheter 109 and the guide wire 112.

Figure 25:
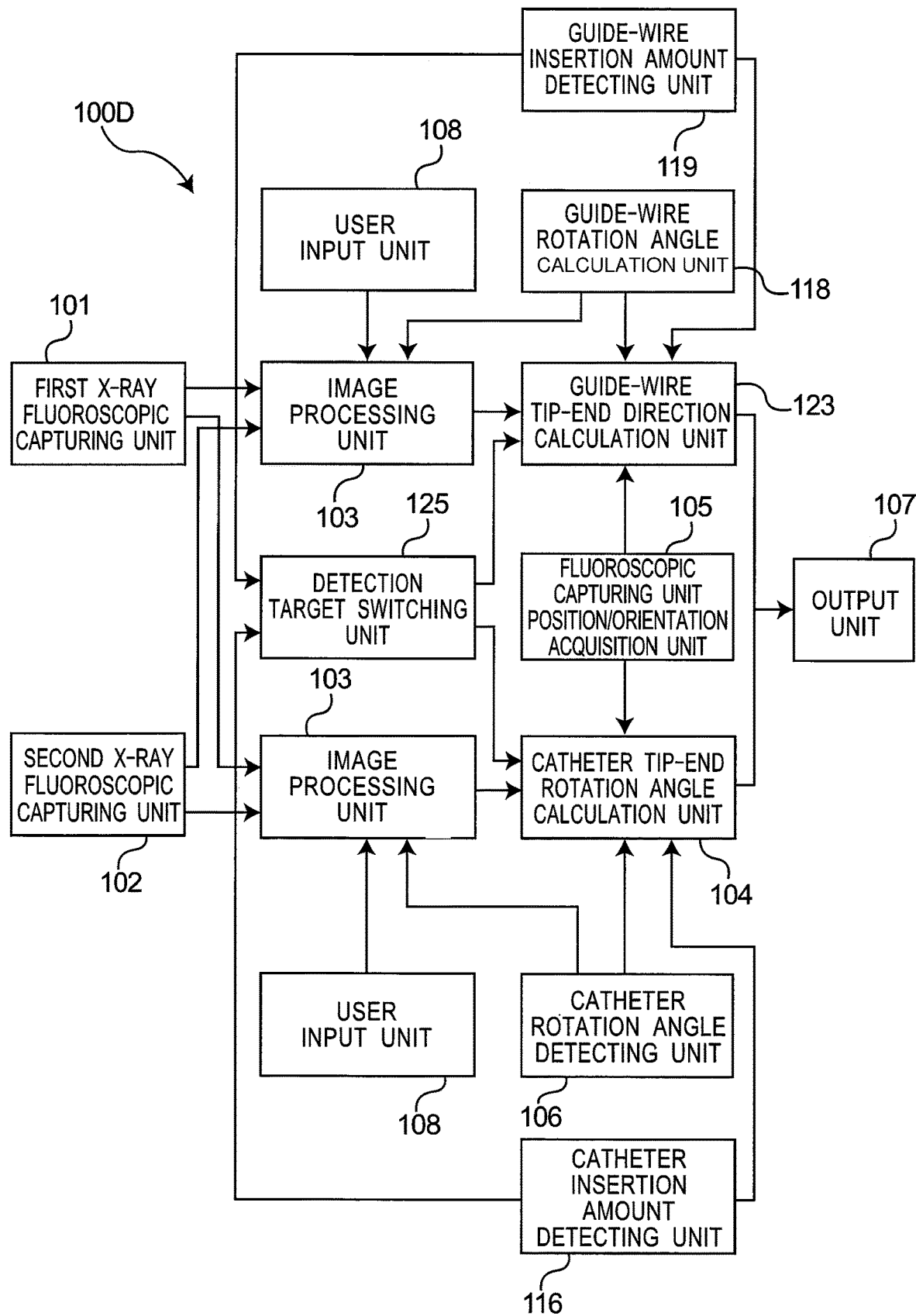
FIG. 25 is a configuration view of functional blocks of a catheter tip-end rotation angle detection apparatus according to a fourth embodiment of the present invention.

FIG. 25 shows a block diagram of the catheter tip-end rotation angle detection apparatus 100D according to the fourth embodiment of the present invention. Descriptions of constituent elements that are the same as those of the first and second embodiments are omitted. Hereinafter, operations of units relating to the fourth embodiment of the present invention are described. In FIG. 25, two user input units 108 and two image processing units 103 are shown. This is just to facilitate the understanding. Actually, the user input unit 108 and the image processing unit 103 are each configured by only one block, respectively.

The catheter tip-end rotation angle detection apparatus 100D according to the fourth embodiment includes a guide-wire rotation angle calculation unit 118, a guide-wire insertion amount detecting unit 119, a guide-wire tip-end rotation angle calculation unit 123, a guide-wire detection condition deciding unit 124, and a detection target switching unit 125, in addition to constituent elements of the first to third embodiments.

The guide-wire rotation angle calculation unit 118 detects a rotation angle of the guide wire 112 in the operator's hand.

The guide-wire insertion amount detecting unit 119 detects an insertion amount of the guide wire 112 into a blood vessel.

At a detection process time, the guide-wire tip-end rotation angle calculation unit 123 calculates an offset angle between the operator's hand-side rotation angle and the guide-wire tip-end rotation angle, from the fluoroscopic image captured when the operator 110 manipulates the guide wire 112 to rotate by one turn, based on an angle at which the guide-wire tip-end becomes a straight line calculated by the image processing unit 103. After ending the detection process, at a guide-wire manipulation time, the guide-wire tip-end rotation angle calculation unit 123 calculates a guide-wire tip-end rotation angle, based on the offset angle and the operator's hand-side rotation angle.

As shown in FIG. 24A, the guide wire 112 has the tip-end bent portion (that is, the guide-wire tip-end region) 112b that is bent in a hook shape relative to a base 112c in a straight line shape. The guide-wire tip-end rotation angle means a rotation angle around the axis of the bent portion (the guide-wire tip-end region) 112b of the tip-end of the guide wire 112. The rotation angle of the guide wire 112 in the operator's hand means a rotation angle around the base in the straight line shape, that is, around the axis of a portion of the guide wire at an operator's hand side. Further, a straight line referred to concerning whether the guide wire tip-end region 112b is a straight line means a state that, from the x-ray fluoroscopic image captured when the catheter operator 110 manipulates the guide wire 112 to rotate by one turn, a superposed state of the bent portion 112b and the base 112c of the wire 112 is in a straight line or in substantially a straight line in the image processing unit 103.

The guide-wire detection condition deciding unit 124 decides whether to perform a catheter detection process, based on the image capture parameters of the fluoroscopic capturing unit position/orientation acquisition unit 105 and a detection value of the guide-wire insertion amount detecting unit 119.

The detection target switching unit 125 switches a detection target of the tip-end rotation angle between the catheter 109 and the guide wire 112, from a detection value of the catheter insertion amount detecting unit 116 and a detection value of the guide-wire insertion amount detecting unit 119.

Each block is described in detail below.

(The Guide-Wire Rotation Angle Calculation Unit 118)

The guide-wire rotation angle calculation unit 118 is a device that detects a rotation angle of the guide wire in a guide-wire operator's hand. The guide-wire rotation angle calculation unit 118 corresponds to a rotation angle sensor such as a rotary encoder, for example.

(The Guide-Wire Insertion Amount Detecting Unit 119)

The guide-wire insertion amount detecting unit 119 is a device that detects an insertion amount of the guide wire in a guide-wire operator's hand. The guide-wire insertion amount detecting unit 119 detects the insertion amount, and outputs the detected insertion amount to the tip-end rotation angle calculation unit 123.

Figure 26:
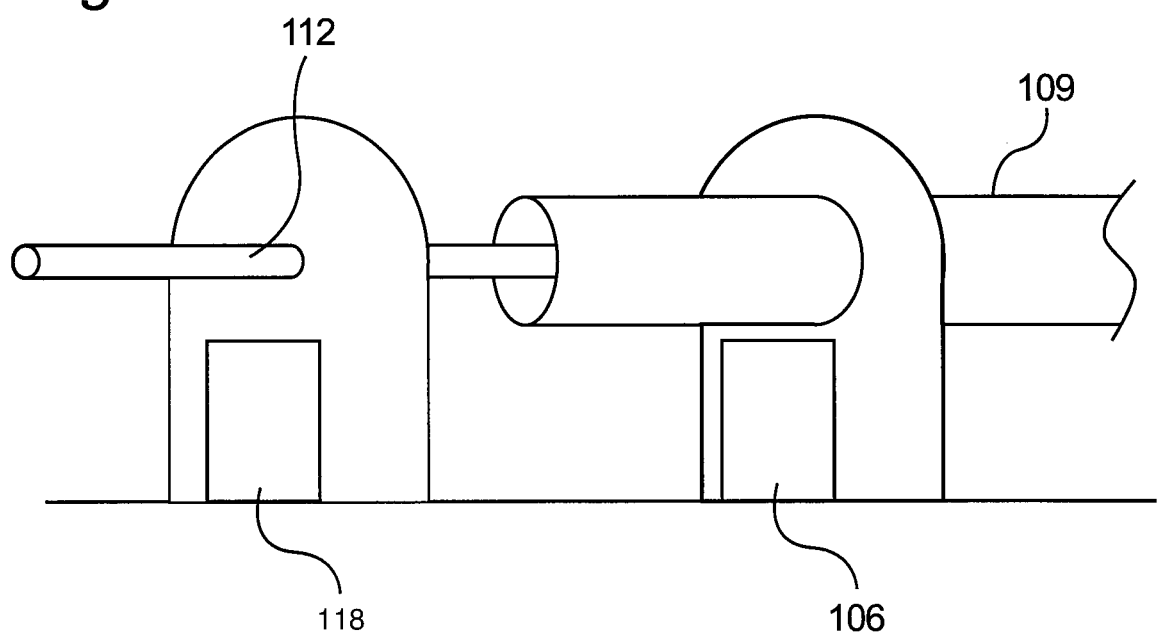
FIG. 26 is an explanatory view of an example arrangement of a catheter rotation angle detecting unit and a catheter insertion amount detecting unit.

As shown in FIGS. 25 and 26, the catheter rotation angle detecting unit 106, the catheter insertion amount detecting unit 116, the guide-wire rotation angle calculation unit 118, and the guide-wire insertion amount detecting unit 119 can independently detect respective angles and lengths. The catheter rotation angle detecting unit 106 and the guide-wire rotation angle calculation unit 118 are respectively provided at different places. For the catheter rotation angle detecting unit 106, as described above, the camera 106a in FIG. 4A or the rotary encoder 106b in FIG. 4B or the like can be used. The guide-wire insertion amount detecting unit 119 is a device similar to the catheter insertion amount detecting unit 116, and can detect an insertion amount.

Standards (positions of an insertion amount zero) of a catheter insertion amount and a guide-wire insertion amount are set as a position of insertion to the patient 111, or a position of the catheter rotation angle detecting unit 106 and a position of the guide-wire insertion amount detecting unit 119. The standards are matched at the time of inserting the catheter 109 and the guide wire 112.

(The Guide-Wire Tip-End Rotation Angle Calculation Unit 123)

The guide-wire tip-end rotation angle calculation unit 123 receives the guide-wire tip-end region from the image processing unit 103, receives the image capture parameters of the first x-ray fluoroscopic capturing unit 101 from the fluoroscopic capturing unit position/orientation acquisition unit 105, and receives the rotation angle of the guide wire in the operator's hand from the guide-wire rotation angle calculation unit 118. The guide-wire tip-end rotation angle calculation unit 123 decides whether a guide-wire tip-end region 109b is a straight line, based on the received information, that is, the guide-wire tip-end region, the image capture parameters, and the operator's hand-side rotation angle. When the guide-wire tip-end rotation angle calculation unit 123 has decided that the guide-wire tip-end region 109b is a straight line, the guide-wire tip-end rotation angle calculation unit 123 calculates a guide-wire rotation axis and a guide-wire coordinate system, from the guide-wire tip-end region 109b and the image capture parameters. At the same time, the guide-wire tip-end rotation angle calculation unit 123 calculates an offset angle between a guide-wire tip-end rotation angle at this time and a guide-wire operator's hand-side rotation angle based on the guide-wire tip-end rotation angle. After calculating the offset angle, the guide-wire tip-end rotation angle calculation unit 123 calculates the guide-wire tip-end rotation angle, from the offset angle and the guide-wire operator's hand-side rotation angle, and outputs a result of the calculation to the output unit 107. When the guide-wire tip-end rotation angle calculation unit 123 has decided that the guide-wire tip-end region 109b is not a straight line, the guide-wire tip-end rotation angle calculation unit 123 outputs to the output unit 107 to urge the user to rotate the guide wire 112.

Figure 27:
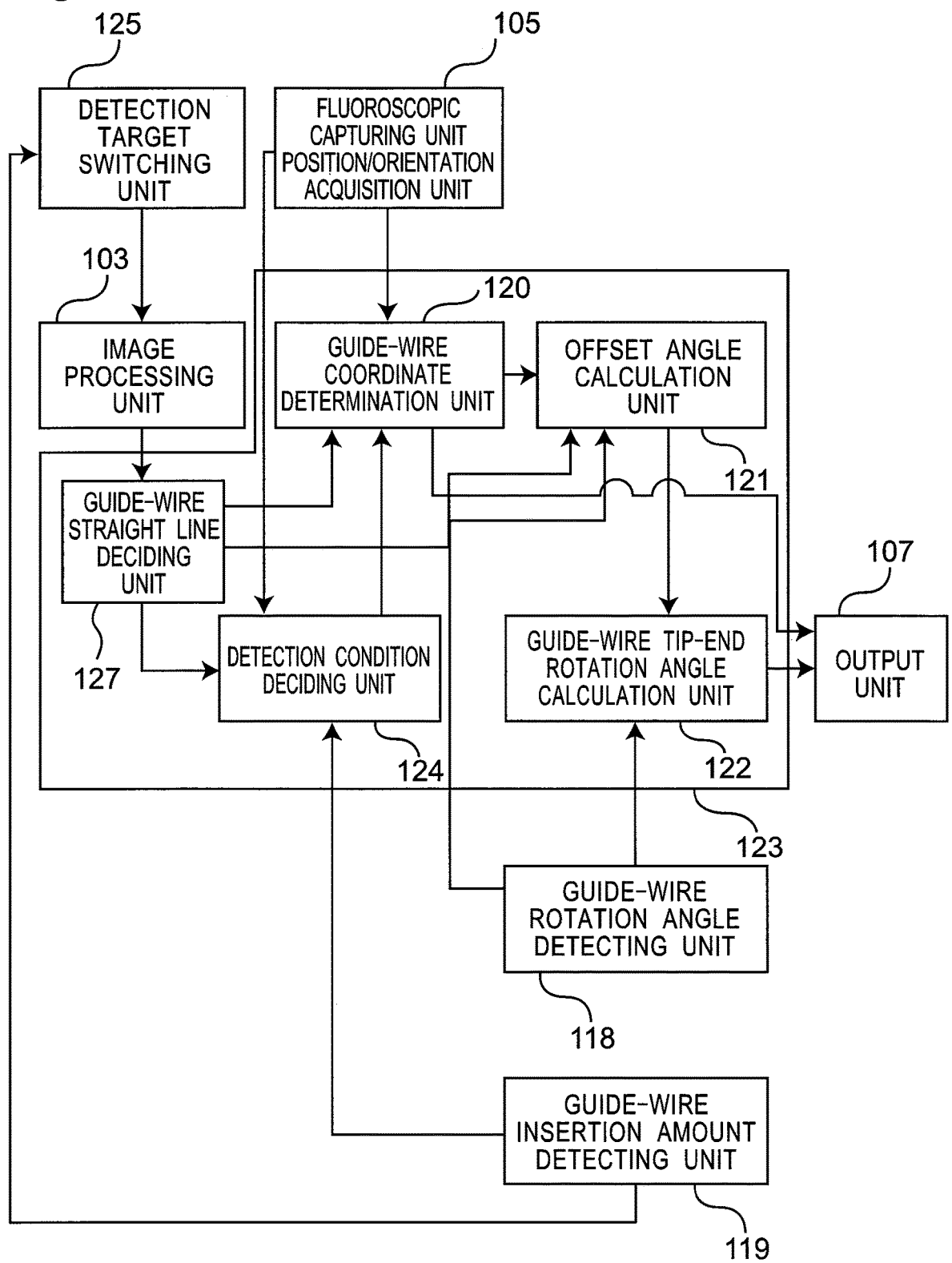
FIG. 27 is a detailed functional block diagram of the guide-wire tip-end rotation angle calculation unit.

A guide-wire tip-end rotation angle calculation process of the guide-wire tip-end rotation angle calculation unit 123 is described in detail below with reference to a block diagram of FIG. 27. The guide-wire tip-end rotation angle calculation unit 123 is configured by a guide-wire straight line deciding unit 127, a guide-wire coordinate determination unit a guide-wire offset angle calculation unit 121, a guide-wire tip-end rotation angle calculation unit 122, and the guide-wire detection condition deciding unit 124.

(The Guide-Wire Straight Line Deciding Unit 127)

The guide-wire straight line deciding unit 127 receives the extraction result of a guide-wire tip-end region from the image processing unit 103, and decides whether the guide-wire tip-end region 109b is a straight line. The guide-wire straight line deciding unit 127 outputs a decision result of the guide-wire straight line deciding unit 127 and the extraction result of a guide-wire tip-end region, to the guide-wire coordinate determination unit 120.

(The Guide-Wire Coordinate Determination Unit 120)

The guide-wire coordinate determination unit 120 calculates a guide-wire coordinate system serving as a standard of a guide-wire tip-end rotation angle, based on a decision result of the guide-wire tip-end region 109b and the image capture parameters. The guide-wire coordinate determination unit 120 receives the decision result of whether the guide-wire tip-end region 109b is a straight line and a result of extracting the guide-wire tip-end region 109b, from the guide-wire straight line deciding unit 127. The guide-wire coordinate determination unit 120 receives the image capture parameters of the first x-ray fluoroscopic capturing unit 101 from the fluoroscopic capturing unit position/orientation acquisition unit 105. When the guide-wire straight line deciding unit 127 decides that the guide-wire tip-end region 109b is a straight line, the guide-wire coordinate determination unit 120 calculates the guide-wire coordinate system from straight line regions in two fluoroscopic images and the image capture parameters.

(The Guide-Wire Offset Angle Calculation Unit 121)

The guide-wire offset angle calculation unit 121 calculates an offset angle between the rotation angle of the guide-wire rotation angle calculation unit 118 and the guide-wire tip-end rotation angle, based on the straight line decision result and the guide-wire operator's hand-side rotation angle. The guide-wire offset angle calculation unit 121 receives the straight line decision result from the guide-wire coordinate determination unit 120. The guide-wire offset angle calculation unit 121 receives the guide-wire operator's hand-side rotation angle from the guide-wire rotation angle calculation unit 118. When a decision result of the guide-wire straight line deciding unit 127 is a straight line, the guide-wire offset angle calculation unit 121 calculates the offset angle by using a value of the guide-wire rotation angle calculation unit as the offset angle, and outputs the offset angle to the guide-wire offset angle calculation unit 121 and the guide-wire tip-end rotation angle calculation unit 122.

(The Guide-Wire Tip-End Rotation Angle Calculation Unit 122)

The guide-wire tip-end rotation angle calculation unit 122 calculates a guide-wire tip-end rotation angle, based on an offset angle and a guide-wire operator's hand-side rotation angle. The guide-wire tip-end rotation angle calculation unit 122 receives the offset angle from the guide-wire offset angle calculation unit 121, and receives the guide-wire operator's hand-side rotation angle from the guide-wire rotation angle calculation unit 118. When the guide-wire operator's hand-side rotation angle acquired from the guide-wire rotation angle calculation unit 118 has changed from the rotation angle at the last measurement time, the guide-wire tip-end rotation angle calculation unit 122 calculates the guide-wire tip-end rotation angle at current time (in detection), from the guide-wire operator's hand-side rotation angle and the offset angle. The guide-wire tip-end rotation angle calculation unit 122 outputs a calculation result to the output unit 107.

(The Guide-Wire Detection Condition Deciding Unit 124)

The guide-wire detection condition deciding unit 124 decides whether to perform a guide-wire detection process, based on a guide-wire tip-end region extraction result, a guide-wire insertion amount, and image capture parameters. The guide-wire detection condition deciding unit 124 receives the guide-wire tip-end region extraction result from the image processing unit 103, receives the guide-wire insertion amount from the guide-wire insertion amount detecting unit 119, and acquires the image capture parameters from the fluoroscopic capturing unit position/orientation acquisition unit 105. The guide-wire detection condition deciding unit 124 decides whether to perform a guide-wire detection process. When the guide-wire detection condition deciding unit 124 decides to perform the guide-wire detection process, the guide-wire detection condition deciding unit 124 outputs a guide-wire tip-end region extraction result to the guide-wire coordinate determination unit 120. When the guide-wire detection condition deciding unit 124 decides not to perform a guide-wire detection process, the guide-wire detection condition deciding unit 124 does not output a guide-wire tip-end region extraction result to the guide-wire coordinate determination unit 120.

(The Detection Target Switching Unit 125)

The detection target switching unit 125 determines a detection target, that is, which one of tip-end rotation angles of the catheter 109 and the guide wire 112 is to be detected, based on a catheter insertion amount and a guide-wire insertion amount. The detection target switching unit 125 receives the catheter insertion amount from the catheter insertion amount detecting unit 116, and receives the guide-wire insertion amount from the guide-wire insertion amount detecting unit 119. The detection target switching unit 125 determines a detection target, from a relation between these two insertion amounts. When the detection target switching unit 125 decides to perform the catheter detection process, the detection target switching unit 125 permits to output the catheter tip-end region extraction result from the image processing unit 103 to the catheter tip-end rotation angle calculation unit 104. On the other hand, when the detection target switching unit 125 decides to perform the guide-wire detection process, the detection target switching unit 125 permits to output the guide-wire tip-end region extraction result from the image processing unit 103 to the guide-wire tip-end rotation angle calculation unit 123.

(A Process Flow of the Catheter Tip-End Rotation Angle Detection Apparatus (Fourth Embodiment))

Figure 28:
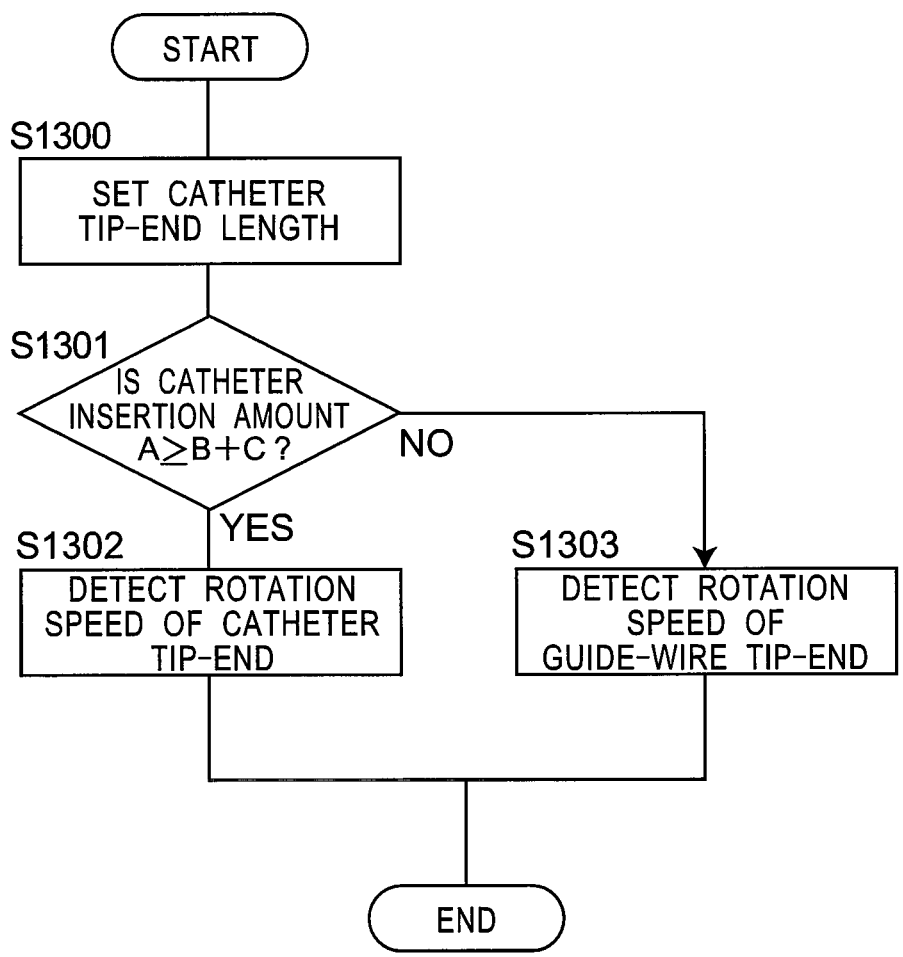
FIG. 28 is a flowchart of a processing of a detection target switching unit.

A flow of a detection-target switch process by the detection target switching unit 125 is described below with reference to a flowchart in FIG. 28.

In step S1300, the detection target switching unit 125 sets a length of the catheter tip-end regions 109b.

Step S1301 is a step in which the detection target switching unit 125 decides a catheter insertion amount A, a guide-wire insertion amount B, and a length C of the catheter tip-end regions 109b. When the detection target switching unit 125 decides that a catheter insertion amount A is equal to or larger than a sum of the guide-wire insertion amount B and the length C of the catheter tip-end regions 109b, a detection target switch process proceeds to step S1302. When the detection target switching unit 125 decides that the catheter insertion amount A is not equal to or larger than the sum of the guide-wire insertion amount B and the length C of the catheter tip-end regions 109b, the detection target switch process proceeds to step S1303.

In step S1302, the detection target switching unit 125 decides that the catheter tip-end rotation angle calculation unit 104 performs the catheter tip-end rotation angle calculation process. The detection target switching unit 125 permits to output the catheter tip-end region extraction result from the image processing unit 103 to the catheter tip-end rotation angle calculation unit 104.

In step S1303, the detection target switching unit 125 decides that the guide-wire rotation angle calculation unit 118 performs the guide-wire rotation angle detection process. The detection target switching unit 125 permits to output the guide-wire tip-end region extraction result from the image processing unit 103 to the guide-wire tip-end rotation angle calculation unit 123.

Figure 29:
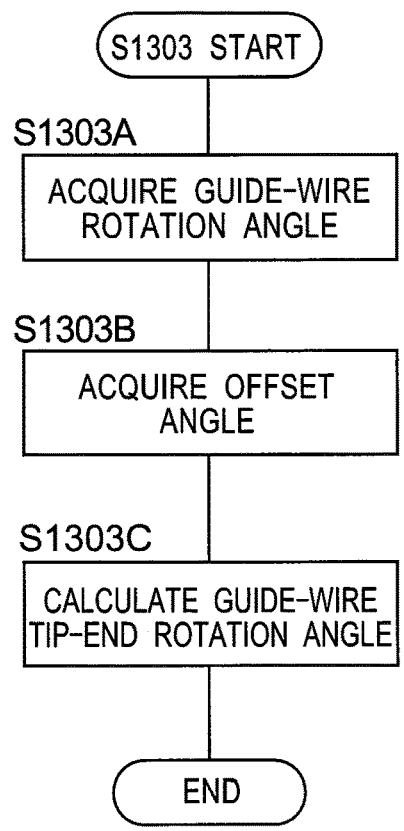
FIG. 29 is a flowchart of a guide-wire tip-end rotation angle calculation process of the guide-wire tip-end rotation angle calculation unit.

A guide-wire tip-end rotation angle calculation process flow S1303 of the guide-wire tip-end rotation angle calculation unit 123 shown in FIG. 29 is similar to a catheter tip-end rotation angle calculation process flow S400 of the catheter tip-end rotation angle calculation unit 104 in FIG. 11. Therefore, a description of FIG. 29 is omitted. Steps S1303A to S1303C correspond to steps S401 to S403, respectively. In the setting of a catheter tip-end length in step S1300, an internal storage of the detection target switching unit 125 may have data of the catheter tip-end length. The kind of the catheter 109 may be input to the user input unit 108. The detection target switching unit 125 may read a catheter length corresponding to the input information, from the internal storage unit, based on the input information to the user input unit 108. For the catheter tip-end length, a fixed value that is stored in advance in the internal storage of the detection target switching unit 125 may be used.

(An Effect of the Fourth Embodiment)

According to the fourth embodiment, tip-end rotation angles of the catheter 109 and the guide wire 112 can be detected. Therefore, the user can smoothly perform a manipulation and surgery, during a manipulation of the guide wire 112 to make the catheter 109 reach the affected part, or during a catheter manipulation of directing a contrast medium to the target blood vessel.

(Fifth Embodiment)

In a fifth embodiment, a method of detecting a catheter tip-end rotation angle in a catheter specific state other than that in the first to the third embodiments is described with reference to FIGS. 30A and 30B.

Figure 30A:
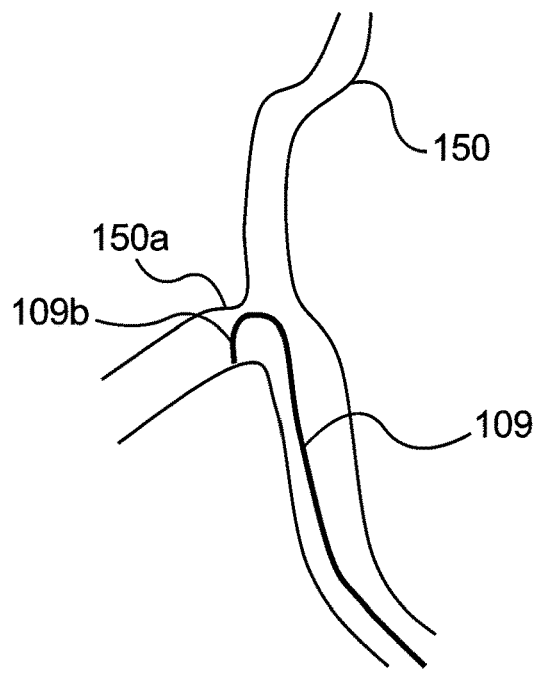
FIG. 30A is a schematic view of a catheter fluoroscopic image showing a behavior of the catheter at a blood vessel branch portion before a pull manipulation.
Figure 30B:
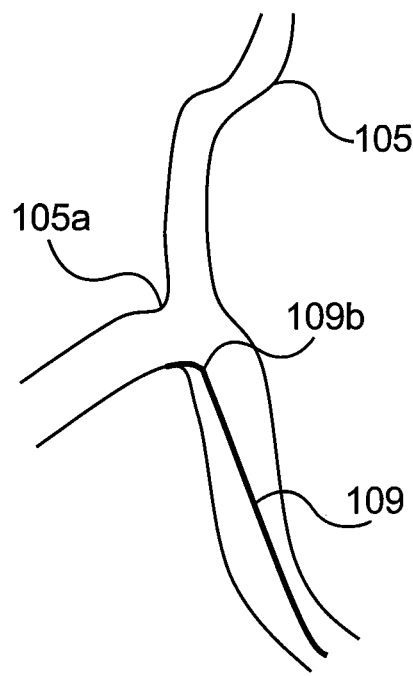
FIG. 30B is a schematic view of a catheter fluoroscopic image showing a behavior of the catheter at the blood vessel branch portion after the pull manipulation.

FIG. 30A shows a catheter fluoroscopic image (schematic view) at a blood vessel branch portion 150a of a blood vessel 150. FIG. 30B shows a fluoroscopic image (schematic view) at the time of extracting the catheter 109 at the blood vessel branch portion 150a. As shown in the drawings, at the time of catheter radiography, the manipulation of pulling the catheter 109 by hooking a catheter tip-end to the blood vessel branch portion 150a is frequently performed (hereinafter, "pulling manipulation"). The catheter operator 110 directs the catheter tip-end to the target blood vessel by performing this pulling manipulation. At this time, as shown in FIG. 30B, because the catheter tip-end is hooked to the blood vessel branch portion 150a during the pulling manipulation, and in some cases, the catheter 109 is deformed from the original catheter shape, and appears to be a straight line in the fluoroscopic image.

In the fifth embodiment, there is described an operation of a catheter tip-end rotation angle detection apparatus 100E when the catheter 109 appears to be a straight line in the fluoroscopic image in other than the rotation manipulation of the catheter 109. In the fifth embodiment, a straight line immediately after the pulling manipulation is not used for a detection operation.

A block diagram of the catheter tip-end rotation angle detection apparatus 100E in the fifth embodiment is common to the block diagram of FIG. 21 for the third embodiment. Therefore, a relevant description is omitted.

(A Process Flow of the Catheter Tip-End Rotation Angle Detection Apparatus (Fifth Embodiment))

Figure 31:
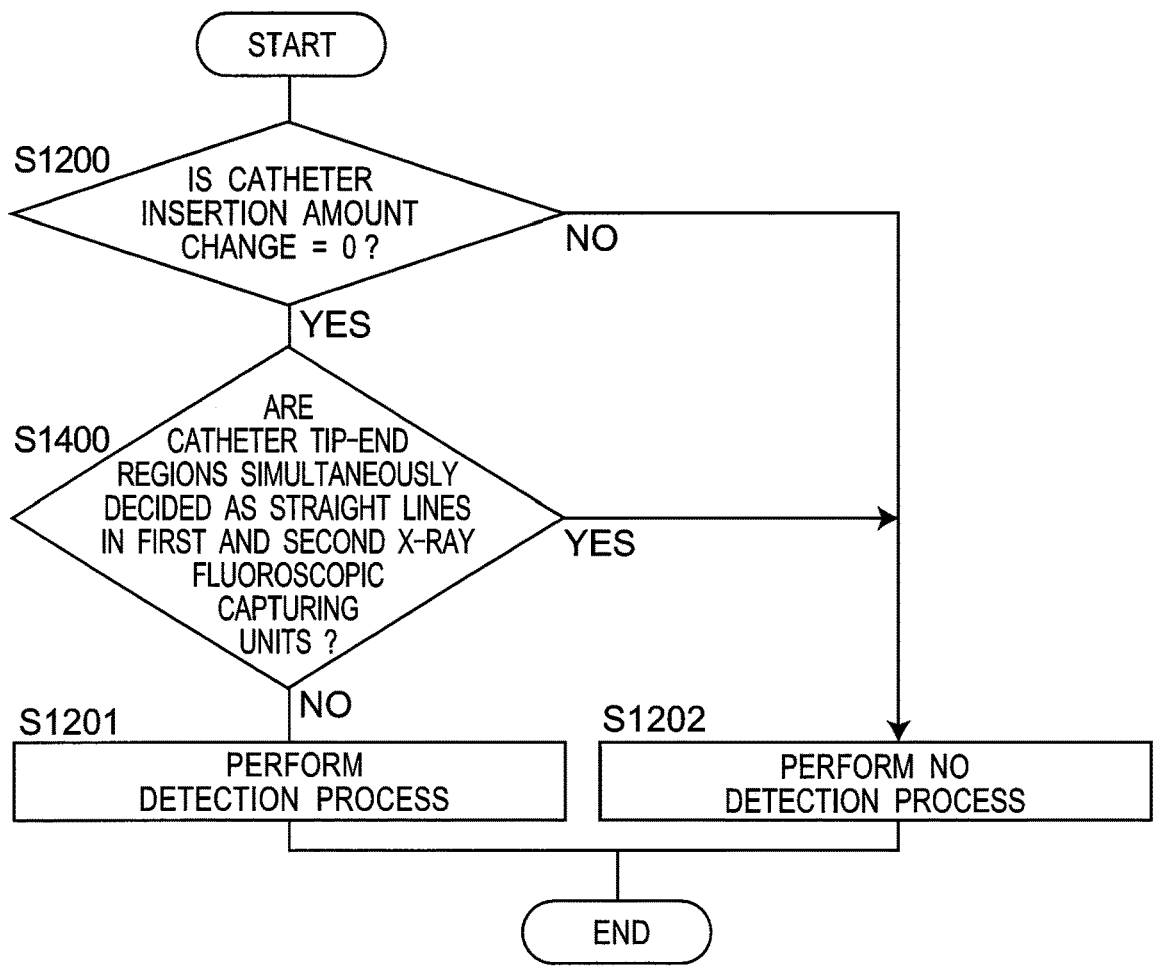
FIG. 31 is an additional process flowchart of the detection condition deciding unit.

An additional process flow of the detection condition deciding unit 117 when the catheter 109 appears to be a straight line in the fluoroscopic image in other than a catheter rotation manipulation is described with reference to a flowchart of FIG. 31.

Step S1200 is a process in which the detection condition deciding unit 117 decides whether there is a change by a predetermined range (error range) or greater in a catheter insertion amount detected by the catheter insertion amount detecting unit 116. When the detection condition deciding unit 117 decides that there is no change in a catheter insertion amount based on a detection value by the catheter insertion amount detecting unit 116, the detection condition decision process proceeds to step S1400. When the detection condition deciding unit 117 decides that there is a change in a catheter insertion amount, the detection condition decision process proceeds to step S1202.

Step S1400 is a step in which the detection condition deciding unit 117 decides whether the catheter tip-end regions 109b have been simultaneously decided as straight lines in two fluoroscopic images of the first x-ray fluoroscopic capturing unit 101 and the second x-ray fluoroscopic capturing unit 102. When the detection condition deciding unit 117 decides that the catheter tip-end regions 109b have not been simultaneously decided as straight lines in two fluoroscopic images, the detection condition decision process proceeds to step S1201. When the detection condition deciding unit 117 decides that the catheter tip-end regions 109b have been simultaneously decided as straight lines in two fluoroscopic images, the catheter is a straight line. Therefore, the detection condition decision process proceeds to step S1202.

In step S1201, the detection condition deciding unit 117 decides to perform the catheter tip-end rotation angle calculation process. Therefore, the detection condition deciding unit 117 permits to output the catheter tip-end region extraction result received from the image processing unit 103, to the catheter coordinate determination unit 113.

In step S1202, the detection condition deciding unit 117 decides not to perform the catheter tip-end rotation angle calculation process. Therefore, the detection condition deciding unit 117 does not output the catheter tip-end region extraction result received from the image processing unit 103, to the catheter coordinate determination unit 113.

(An Effect of the Fifth Embodiment)

According to the fifth embodiment, an erroneous detection is not performed during an operation that frequently occurs at the time of a catheter contrast radiography. Therefore, the user can smoothly perform a catheter manipulation and surgery, at the time of directing a contrast medium to a target blood vessel.

The present invention is not limited to the above embodiments, and can be implemented in various modes.

Figures 9, 10A:
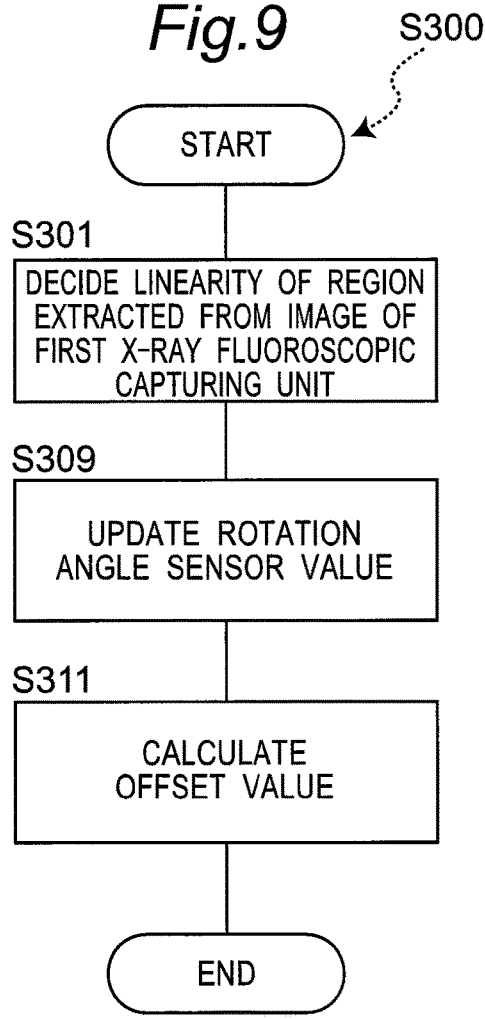
FIG. 9 is a view showing a process flow of an offset angle calculation unit.
FIG. 10A is an explanatory view showing an example of a correspondence table between an image and an operator's hand-side rotation angle at an offset value calculation time.
Figures 10B, 11:
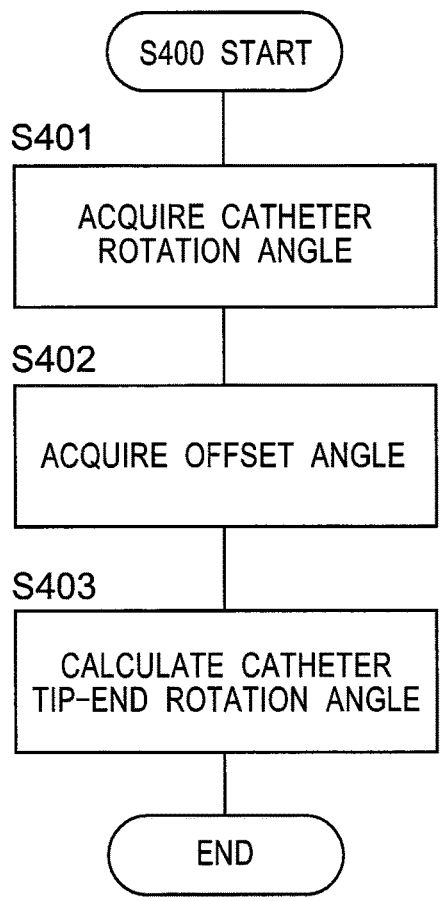
FIG. 10B is an explanatory view showing an example of a correspondence table between an image and an operator's hand-side rotation angle obtained when a catheter is rotated by one turn at an offset value calculation time.
FIG. 11 is a view showing a process flow of the catheter tip-end rotation angle calculation unit.

For example, an evaluation value that indicates linearity may be calculated in steps S301 and S302 of FIG. 9, and the catheter tip-end region 109b in which the evaluation value becomes maximum may be acquired in steps S303 and S304.

Further, in the second embodiment, when the output unit 107 does not perform a three-dimensional display, only an offset angle calculation may be performed, without performing the process of the catheter coordinate determination unit 113 in the catheter tip-end rotation angle calculation unit 104.

The output unit 107 may display a catheter tip-end rotation angle that is received from the catheter tip-end rotation angle calculation unit 104, as a character string.

Though the present disclosure has been described above based on the above first to fifth embodiments and modification examples, the present disclosure should not be limited to the above-described first to fifth embodiments and modification examples. For example, the present disclosure also includes the following cases.

Part or entirety of each of the above-described apparatuses is actually a computer system that includes, for example, a microprocessor, ROM, RAM, hard disk unit, display unit, keyboard, mouse, and the like. A computer program is stored on the RAM or the hard disk unit. Functions of each of the apparatuses can be achieved by the microprocessor operating according to the computer program. The computer program mentioned here is a combination of a plurality of instruction codes that indicate commands to a computer for achieving predetermined functions.

For example, each component can be implemented as a result that a program executing section (part/unit) such as a CPU reads and executes software programs recorded in a recording medium such as a hard disk or semiconductor memory. Here, software that implements a part or entirety of the apparatus according to each of the above-mentioned embodiments or modifications is a following program. That is to say, this program has a computer execute the sections (parts/units) defined in claims. The program has a computer execute the units/steps defined in claims. That is, such a program is a catheter tip-end rotation angle detection program for detecting a rotation angle around an axis of a bent portion of a catheter, the catheter having the bent portion at a tip-end that is bent in a hook shape relative to a straight-line shaped base, as a catheter tip-end region, and being inserted into a body lumen, the catheter tip-end rotation angle detection program makes a computer function as:

a catheter rotation angle detecting unit that detects an operator's hand-side rotation angle of the catheter in a hand of an operator;

an image processing unit that extracts the catheter tip-end region from an x-ray fluoroscopic image of a first x-ray fluoroscopic capturing unit that captures an x-ray fluoroscopic image by irradiating a radioactive ray to an image-capture target portion of a subject;

a catheter tip-end rotation angle calculation unit that performs a catheter tip-end rotation angle calculation process in which an offset angle between the operator's hand-side rotation angle detected by the catheter rotation angle detecting unit and a rotation angle of the catheter tip-end is calculated from an x-ray fluoroscopic image captured at a time of an action of rotating the catheter by one turn by the operator, based on respective angles of the bent portion and the base of the catheter in a state that the bent portion and the base are superposed and in a state that the bent portion and the base are deviated in the image processing unit and, during a catheter manipulation after ending the action of rotating the catheter by the one turn, the catheter tip-end rotation angle is calculated based on the offset angle and the operator's hand-side rotation angle; and an output unit that outputs the catheter tip-end rotation angle calculated by the catheter tip-end rotation angle calculation unit.

In addition, it may be possible to execute the program by downloading it from a server or reading it from a predetermined storage medium (an optical disc such as a CD-ROM, a magnetic disc, a semiconductor memory, or the like)

Further, one or more computers can be used to execute the program. That is, centralized processing or distributed processing can be performed.

By properly combining the arbitrary embodiment (s) or modification(s) of the aforementioned various embodiments and modifications, the effects possessed by the embodiment (s) or modification(s) can be produced.

The entire disclosure of Japanese Patent Application No. 2012-173859 filed on Aug. 6, 2012, including specification, claims, drawings, and summary are incorporated herein by reference in its entirety.

INDUSTRIAL APPLICABILITY

The catheter tip-end rotation angle detection apparatus, the catheter tip-end rotation angle detection method, and the catheter tip-end rotation angle detection program according to the present invention have a function of detecting a catheter tip-end direction, and are useful at the time of catheter contrast radiography. The catheter tip-end rotation angle detection apparatus, the catheter tip-end rotation angle detection method, and the catheter tip-end rotation angle detection program according to the present invention can be also applied to catheter manipulation education for trainee doctors.

Although the present disclosure has been fully described in connection with the embodiments thereof with reference to the accompanying drawings, it is to be noted that various changes and modifications are apparent to those skilled in the art. Such changes and modifications are to be understood as included within the scope of the present disclosure as defined by the appended claims unless they depart therefrom.

What is claimed is:

1. A catheter tip-end rotation angle detection apparatus that detects a rotation angle around an axis of a bent portion of a catheter, the catheter having the bent portion at a tip-end that is bent in a hook shape relative to a straight-line shaped base, as a catheter tip-end region, and being inserted into a body lumen of a patient, the catheter tip-end rotation angle detection apparatus comprising:
a catheter rotation angle detector configured to detect an operator's hand-side rotation angle of the catheter held by an operator by detecting a pattern applied to the catheter on an operator's hand-side outside of a body of the patient;
a rotation angle detection processor; and
a non-transitory memory configured to store a program, which is executed by the rotation angle detection processor and causes the catheter tip-end rotation angle detection apparatus to:
extract the catheter tip-end region from an x-ray fluoroscopic image of an x-ray fluoroscopic image captured by irradiating an image-capture target portion of the patient;
execute a catheter tip-end rotation angle calculation process in which: 1) an offset angle between the operator's hand-side rotation angle detected and a rotation angle of the catheter tip-end is calculated using an x-ray fluoroscopic image captured at a time of an action of rotating the catheter by one turn, based on respective angles of the bent portion and the base of the catheter when the bent portion and the base are superposed and the bent portion and the base are deviated, and 2) during a catheter manipulation after ending the action of rotating the catheter by the one turn a catheter tip-end rotation angle is calculated based on the offset angle and the operator's hand-side rotation angle; and
a display configured to output and display an image of the catheter tip-end rotation angle superposed with a fluoroscopic image based on the catheter tip-end rotation angle calculated,
wherein the rotation angle detection processor is configured to execute the program to further: determine whether the catheter tip-end region is oriented in a straight line, based on an extraction result of the catheter tip-end region,
calculate the offset angle between the operator's hand-side rotation angle and the catheter tip-end rotation angle, based on a straight line decision result and the operator's hand-side rotation angle, and
calculate the catheter tip-end rotation angle, based on the offset angle and the operator's hand-side rotation angle.

2. The catheter tip-end rotation angle detection apparatus according to claim 1, further comprising:
a user interface configured to receive an instruction input by the operator and start the catheter tip-end rotation angle calculation process, wherein
after the operator inputs the instruction to start the catheter tip-end rotation angle calculation process using the user interface, the rotation angle detection processor is configured to start the catheter tip-end rotation angle calculation process.

3. The catheter tip-end rotation angle detection apparatus according to claim 1, wherein the rotation angle detection processor is configured to execute the program and cause the catheter tip-end rotation angle detection apparatus to:
acquire position/orientation of a first x-ray fluoroscopic capturing unit and a second x-ray fluoroscopic capturing unit configured to capture an x-ray fluoroscopic image at a position different from a position of the first x-ray fluoroscopic capturing unit, when the first x-ray fluoroscopic capturing unit and the second x-ray fluoroscopic capturing unit capture x-ray fluoroscopic images,
wherein the rotation angle detection processor is configured to extract the catheter tip-end region from the respective x-ray fluoroscopic images of the first x-ray fluoroscopic capturing unit and the second x-ray fluoroscopic capturing unit.

4. The catheter tip-end rotation angle detection apparatus according to claim 1, wherein the rotation angle detection processor is configured to execute the program and cause the catheter tip-end rotation angle detection apparatus to:
detect an insertion amount of the catheter into the body lumen; and
by determining whether the insertion amount of the catheter detected changes, determine that the catheter tip-end rotation angle calculation process is performed when it is decided that the insertion amount of the catheter does not change, and determine that the catheter tip-end rotation angle calculation process is not performed when it is decided that the insertion amount of the catheter changes.

5. The catheter tip-end rotation angle detection apparatus according to claim 1, wherein the rotation angle detection processor is configured to execute the program and cause the catheter tip-end rotation angle detection apparatus to:
   detect an insertion amount of a guide wire inserted into the body lumen, the guide wire having a bent portion at a tip-end which is bent in a hook shape relative to a straight-line shaped base, as a guide-wire tip-end region, movable in the catheter and inserted into the body lumen;
   detect a wire operator's hand-side rotation angle of the guide wire held by an operator; and
   perform a guide-wire tip-end rotation angle calculation process in which: 1) an offset angle between the wire operator's hand-side rotation angle detected and a rotation angle of the guide-wire tip-end is calculated from an x-ray fluoroscopic image captured at a time of an action of rotating the guide wire by one turn by the operator, based on respective angles of the bent portion and the base of the guide wire when the bent portion and the base are superposed and the bent portion and the base of the guide wire are deviated, and 2) during a guide-wire manipulation after ending the action of rotating the guide wire by the one turn, a guide wire tip-end rotation angle is calculated based on the offset angle and the operator's hand-side rotation angle,
   wherein the rotation angle detection processor is configured to extract a guide-wire tip-end region from the x-ray fluoroscopic image, and
   the rotation angle detection processor is configured to execute the program and cause the catheter tip-end rotation angle detection apparatus to:
   by comparing the insertion amount of the guide wire detected, the insertion amount of the catheter detected, and a length of the catheter tip-end region, output a result by setting the catheter as a detection target when the insertion amount of the catheter is larger than a sum of the insertion amount of the guide wire and the length of the catheter tip-end region, and output a result by setting the guide wire as a detection target when the insertion amount of the catheter is smaller than a sum of the insertion amount of the guide wire and the length of the catheter tip-end region.

6. The catheter tip-end rotation angle detection apparatus according to claim 3, wherein the rotation angle detection processor is configured to execute the program and cause the catheter tip-end rotation angle detection apparatus to:
   decide that the bent portion of the catheter is extended in a straight-line shape when it is decided that the catheter tip-end region acquired from the respective x-ray fluoroscopic images of the first x-ray fluoroscopic capturing unit and the second x-ray fluoroscopic capturing unit is simultaneously in the superposed state, and decide that the catheter tip-end rotation angle calculation process is not performed.

7. The catheter tip-end rotation angle detection apparatus according to claim 1, wherein the display displays in a plane by a two-dimensional vector the catheter tip-end rotation angle calculated.

8. The catheter tip-end rotation angle detection apparatus according to claim 1, wherein the rotation angle detection processor is configured to execute the program and cause the catheter tip-end rotation angle detection apparatus to:
   calculate a catheter coordinate system, and a catheter tip-end rotation angle in a three-dimensional space from a catheter tip-end rotation angle calculated,
   wherein the display has a three-dimensional shape model of the catheter, orientation-converts the three-dimensional shape model into the catheter tip-end rotation angle calculated by the catheter coordinate determination unit, and three-dimensionally displays an orientation-converted result.

9. The catheter tip-end rotation angle detection apparatus according to claim 8, wherein the display re-projects a catheter tip-end rotation angle in a vector viewed from an image-capture viewpoint, based on a catheter tip-end rotation angle in a three-dimensional space acquired and image capture parameters acquired, and that superposes and displays a catheter tip-end rotation angle at the image-capture viewpoint on a fluoroscopic image.

10. The catheter tip-end rotation angle detection apparatus according to claim 1, wherein the catheter rotation angle detector is located outside of the patient when detecting the operator's hand-side rotation angle of the catheter.

11. A catheter tip-end rotation angle detection apparatus that detects a rotation angle around an axis of a bent portion of a catheter, the catheter having the bent portion at a tip-end that is bent in a hook shape relative to a straight-line shaped base, as a catheter tip-end region, and being inserted into a body lumen of a patient, the catheter tip-end rotation angle detection apparatus comprising:
   a catheter rotation angle detector configured to detect an operator's hand-side rotation angle of the catheter by detecting a pattern applied to the catheter on an operator's hand-side outside of a body of the patient;
   a rotation angle detection processor;
   a non-transitory memory configured to store a program; and
   a display,
   wherein the rotation angle detection processor is configured to execute the program to cause the catheter tip-end rotation angle detection apparatus to:
   extract the catheter tip-end region from an x-ray fluoroscopic image of an x-ray fluoroscopic image captured by irradiating an image-capture target portion of the patient,
   determine whether the catheter tip-end region is oriented in a straight line, based on an extraction result of the catheter tip-end region,
   calculate an offset angle between the operator's hand-side rotation angle and a catheter tip-end rotation angle, based on a straight line decision result and the operator's hand-side rotation angle, and
   calculate the catheter tip-end rotation angle, based on the offset angle and the operator's hand-side rotation angle, and
   the display outputs and displays an image of the catheter tip-end rotation angle.

12. A catheter tip-end rotation angle detection apparatus that detects a rotation angle around an axis of a bent portion of a catheter, the catheter having the bent portion at a tip-end that is bent in a hook shape relative to a straight-line shaped base, as a catheter tip-end region, and being inserted into a body lumen of a patient, the catheter tip-end rotation angle detection apparatus comprising:
   a catheter rotation angle detector configured to detect an angle of a proximal end of the catheter by detecting a pattern applied to the catheter on an operator's hand-side outside of a body of the patient;
   a rotation angle detection processor;
   a non-transitory memory configured to store a program; and
   a display, wherein the rotation angle detection processor is configured to execute the program to cause the catheter tip-end rotation angle detection apparatus to:

extract the catheter tip-end region from an x-ray fluoroscopic image of an x-ray fluoroscopic image captured by irradiating an image-capture target portion of the patient, determine whether the catheter tip-end region is oriented in a straight line, based on an extraction result of the catheter tip-end region, calculate an offset angle between the angle of the proximal end of the catheter and a catheter tip-end rotation angle, based on a straight line decision result and the angle of the proximal end of the catheter, and calculate the catheter tip-end, based on the offset angle and the angle of the proximal end of the catheter, and the display outputs and displays an image of the catheter tip-end rotation angle.

* * * * *